(12) United States Patent
Cottenden et al.

(10) Patent No.: US 12,357,776 B2
(45) Date of Patent: Jul. 15, 2025

(54) MEDICINAL INHALERS

(71) Applicant: KINDEVA DRUG DELIVERY L.P., St. Paul, MN (US)

(72) Inventors: David J. Cottenden, Melbourn (GB); Christopher G. Blatchford, Loughborough (GB); William T. Richardson, Royston (GB); Romain U. G. Guion, Cambridge (GB); Iain G. McDerment, Melbourn (GB); Christopher B. J. Groombridge, Stevenage (GB); Simon L. Calcutt, Cambridge (GB)

(73) Assignee: Kindeva Drug Delivery L.P., St. Paul, MN (US)

( * ) Notice: Subject to any disclaimer, the term of this patent is extended or adjusted under 35 U.S.C. 154(b) by 1132 days.

(21) Appl. No.: 16/064,433

(22) PCT Filed: Dec. 6, 2016

(86) PCT No.: PCT/US2016/065113
§ 371 (c)(1),
(2) Date: Jun. 20, 2018

(87) PCT Pub. No.: WO2017/112400
PCT Pub. Date: Jun. 29, 2017

(65) Prior Publication Data
US 2019/0001085 A1 Jan. 3, 2019

Related U.S. Application Data

(60) Provisional application No. 62/270,081, filed on Dec. 21, 2015, provisional application No. 62/289,676, filed on Feb. 1, 2016.

(51) Int. Cl.
*A61H 15/00* (2006.01)
*A61M 15/00* (2006.01)
*A61M 16/00* (2006.01)

(52) U.S. Cl.
CPC ...... *A61M 15/0091* (2013.01); *A61M 15/002* (2014.02); *A61M 15/009* (2013.01);
(Continued)

(58) Field of Classification Search
CPC ............... A61M 15/00; A61M 15/002; A61M 15/0001; A61M 15/0065; A61M 15/0068;
(Continued)

(56) References Cited

U.S. PATENT DOCUMENTS

| 4,414,972 A | 11/1983 | Young et al. |
| 5,161,524 A | 11/1992 | Evans |

(Continued)

FOREIGN PATENT DOCUMENTS

| CN | 102686261 A | 9/2012 |
| DE | 199 12 461 | 9/2000 |

(Continued)

OTHER PUBLICATIONS

Levy, M.L. et al.; "Asthma patients' inability to use a pressurised metered-dose inhaler (pMDI) correctly correlates with poor asthma control as defined by the Global Initiative for Asthma (GINA) strategy: a retrospective analysis"; Primary Care Respiratory Journal; vol. 22, No. 4; 2013; pp. 406-411.
(Continued)

*Primary Examiner* — LaToya M Louis
(74) *Attorney, Agent, or Firm* — Mueting Raasch Group

(57) ABSTRACT

A medicinal inhaler. The inhaler can include a housing, and an air flow path defined by at least partially the housing and including an air inlet and an air outlet. The inhaler can further include a flow governor and a breath-actuated dose
(Continued)

release firing system. The flow governor can be positioned in the air flow path between the air inlet and the air outlet to govern air flow in the air flow path to a governing volumetric flow rate. The breath-actuated dose release firing system can be located in the housing and can be configured to release a dose of medicament at a firing volumetric flow rate less than the governing volumetric flow rate.

13 Claims, 28 Drawing Sheets

(52) U.S. Cl.
CPC ............... *A61M 2016/0018* (2013.01); *A61M 2016/0027* (2013.01); *A61M 2205/0266* (2013.01); *A61M 2205/3331* (2013.01); *A61M 2205/3334* (2013.01); *A61M 2205/3341* (2013.01); *A61M 2205/3358* (2013.01); *A61M 2205/50* (2013.01); *A61M 2205/8206* (2013.01); *A61M 2205/8281* (2013.01)

(58) Field of Classification Search
CPC ............ A61M 15/0071; A61M 15/008; A61M 15/0081; A61M 15/0083; A61M 15/009; A61M 15/0091; A61M 2205/332; A61M 2205/3334
See application file for complete search history.

(56) References Cited

U.S. PATENT DOCUMENTS

| | | | |
|---|---|---|---|
| 5,217,004 A | 6/1993 | Blasnik et al. | |
| 5,347,998 A | 9/1994 | Hodson et al. | |
| 5,392,768 A * | 2/1995 | Johansson | A61M 15/00 128/200.14 |
| 5,437,271 A | 8/1995 | Hodson et al. | |
| 5,450,336 A * | 9/1995 | Rubsamen | A61M 15/0091 341/120 |
| 5,617,844 A | 4/1997 | King | |
| 5,655,520 A | 8/1997 | Howe et al. | |
| 5,692,492 A | 12/1997 | Bruna et al. | |
| 5,896,853 A | 4/1999 | Howlett | |
| 5,941,240 A | 8/1999 | Gonda et al. | |
| 5,954,047 A | 9/1999 | Armer et al. | |
| 6,070,573 A * | 6/2000 | Howe | A61M 15/0086 128/200.14 |
| 6,109,261 A | 8/2000 | Clarke et al. | |
| 6,176,237 B1 | 1/2001 | Wunderlich et al. | |
| 6,240,918 B1 | 6/2001 | Ambrosio et al. | |
| 6,260,549 B1 | 7/2001 | Sosiak | |
| 6,328,035 B1 | 12/2001 | Wakefield et al. | |
| 6,357,442 B1 | 3/2002 | Casper et al. | |
| 6,581,590 B1 | 6/2003 | Genova et al. | |
| 6,637,432 B2 | 10/2003 | Wakefield et al. | |
| 6,655,379 B2 | 12/2003 | Clark et al. | |
| 6,668,826 B1 | 12/2003 | Myrman | |
| 6,681,762 B1 | 1/2004 | Scheuch | |
| 6,904,907 B2 | 6/2005 | Speldrich et al. | |
| 7,073,499 B1 | 7/2006 | Reinhold et al. | |
| 7,296,567 B2 | 11/2007 | Mahon et al. | |
| 7,299,800 B2 | 11/2007 | Stradella | |
| 7,363,924 B2 | 4/2008 | Stradella | |
| 7,891,358 B2 | 2/2011 | Kolb et al. | |
| 8,286,837 B1 | 10/2012 | Blake | |
| 8,684,002 B2 | 4/2014 | Huber et al. | |
| 8,944,050 B2 | 2/2015 | Hyun et al. | |
| 2002/0000225 A1 | 1/2002 | Schuler et al. | |
| 2002/0189612 A1 | 12/2002 | Rand | |
| 2003/0005926 A1 | 1/2003 | Jones et al. | |
| 2003/0079744 A1 | 5/2003 | Bonney et al. | |
| 2004/0050385 A1 | 3/2004 | Bonney et al. | |
| 2005/0022806 A1 | 2/2005 | Beaumont et al. | |
| 2006/0137681 A1 | 6/2006 | Von Hollen et al. | |
| 2006/0231093 A1 | 10/2006 | Burge et al. | |
| 2008/0178872 A1* | 7/2008 | Genova | A61M 15/0026 128/200.23 |
| 2009/0314372 A1* | 12/2009 | Ruskewicz | A61M 15/0086 138/46 |
| 2012/0010575 A1 | 1/2012 | Jones et al. | |
| 2012/0103329 A1 | 5/2012 | Smith | |
| 2013/0298907 A1 | 11/2013 | Zuyderhoudt | |
| 2013/0033172 A1 | 12/2013 | Claude | |
| 2014/0352690 A1 | 12/2014 | Kolb et al. | |

FOREIGN PATENT DOCUMENTS

| | | |
|---|---|---|
| DE | 101 26 807 | 12/2002 |
| EP | 0 050 654 | 5/1982 |
| EP | 0 147 028 | 7/1985 |
| EP | 0 490 797 | 6/1992 |
| EP | 0 808 635 | 11/1997 |
| EP | 0 895 788 | 2/1999 |
| EP | 0 965 355 | 12/1999 |
| EP | 1 036 569 | 9/2000 |
| EP | 1 163 921 | 12/2001 |
| EP | 1 399 210 | 3/2004 |
| GB | 2 104 393 | 3/1983 |
| GB | 2 266 466 | 11/1993 |
| GB | 2 398 254 | 8/2004 |
| JP | 2007-505644 A | 3/2007 |
| KR | 10-2015-0118195 | 10/2015 |
| WO | WO 1992/07600 | 5/1992 |
| WO | WO 1992/09323 | 6/1992 |
| WO | WO 1992/12799 | 8/1992 |
| WO | WO 1995/05208 | 2/1995 |
| WO | WO 98/21419 A1 | 5/1998 |
| WO | WO 1998/41253 | 9/1998 |
| WO | WO 1999/06091 | 2/1999 |
| WO | WO 1999/47196 | 9/1999 |
| WO | WO 2000/16838 | 3/2000 |
| WO | WO 2000/78378 | 12/2000 |
| WO | WO 2001/00263 | 1/2001 |
| WO | WO 2001/34231 | 5/2001 |
| WO | WO 2001/41845 | 6/2001 |
| WO | WO 2001/41847 | 6/2001 |
| WO | WO 2001/41849 | 6/2001 |
| WO | WO 2001/41851 | 6/2001 |
| WO | WO 2001/70313 | 9/2001 |
| WO | WO 2001/70316 | 9/2001 |
| WO | WO 2001/70319 | 9/2001 |
| WO | WO 2001/85245 | 11/2001 |
| WO | WO 2002/24267 | 3/2002 |
| WO | WO 2002/100469 | 12/2002 |
| WO | WO 2003/000329 | 1/2003 |
| WO | WO 2003/035155 | 5/2003 |
| WO | WO 2003/055548 | 7/2003 |
| WO | WO 2005/025654 A1 | 3/2005 |
| WO | WO 2006/106367 | 10/2006 |
| WO | WO 2008/016698 | 2/2008 |
| WO | WO 2008/070516 | 6/2008 |
| WO | WO 2009/128491 | 10/2009 |
| WO | WO 2011/079310 A1 | 6/2011 |
| WO | WO 2015/034709 | 3/2015 |
| WO | WO 2017/112451 | 6/2017 |
| WO | WO 2017/112452 | 6/2017 |
| WO | WO 2017/112476 | 6/2017 |
| WO | WO 2017/112748 | 6/2017 |

OTHER PUBLICATIONS

Chinese Office Action issued by the Chinese Patent Office for CN Application No. 201680082007.X dated May 28, 2020; 15 pgs.
Japanese Office Action issued by the Japanese Patent Office for JP Application No. 2018-551755 dated Dec. 8, 2020; 7 pgs. including English Translation.
Japanese Final Office Action for JP Application No. 2018-551755 issued by the Japanese Patent Office; dated Nov. 9, 2021: 5 pgs. including English translation.

(56) References Cited

OTHER PUBLICATIONS

Chinese Office Action for CN Application No. 202111110732.2 issued by the Chinese Patent Office on Oct. 31, 2022; 17 pgs. including English translation.

* cited by examiner

MEDICINAL INHALERS

CROSS REFERENCE TO RELATED APPLICATIONS

This application is a national stage filing under 35 U.S.C. 371 of PCT/US2016/065113, filed Dec. 6, 2016, which claims the benefit of U.S. Provisional Patent Application No. 62/270,081, filed Dec. 21, 2015 and U.S. Provisional Patent Application No. 62/289,676, filed Feb. 1, 2016, the disclosures of which are incorporated by reference in their entirety herein.

FIELD

The present disclosure generally relates to medicinal inhalers, and particularly, to medicinal inhalers comprising a flow governor and a breath-actuated dose release firing system.

BACKGROUND

Delivery of aerosolized medicament to the respiratory tract for the treatment of respiratory and other diseases is conventionally done using inhalers of either the pressurised metered dose inhaler (pMDI), the dry powder inhaler (DPI) or the nebulizer type. pMDI inhalers in particular have become an industry standard, and are familiar to many patients who suffer from either asthma or from chronic obstructive pulmonary disease (COPD). Conventional pMDI devices comprise an aluminum canister, sealed with a metering valve, which contains the medicament formulation. Generally, the medicament formulation is a pressurized formulation containing either fine particles of one or more medicinal compounds suspended in a liquefied hydrofluoroalkane (HFA) propellant, or a solution of one or more medicinal compounds dissolved in a propellant/co-solvent system. Formulations incorporating one drug in solution and another one in suspension form are also known.

In a conventional pulmonary pMDI, the sealed canister is provided to the patient in an actuator. The actuator is conventionally a generally L-shaped plastic molding comprising a generally cylindrical vertical tube that surrounds the canister plus a generally horizontal tube that forms a patient portion (e.g., a mouthpiece or nosepiece) that defines an inspiration (or inhalation) orifice. To use such an inhaler, the patient exhales, places the patient port into a body cavity (e.g., a mouth or nose) and then inhales to draw air through the inspiration orifice. The majority of such inhalers are of the pulmonary "press-and-breathe" type, where the patient must press down on the protruding end of the canister in order to operate the metering valve to release a metered dose of medicament from the canister into the inhaled air stream and thence through the mouthpiece into their lungs. This requires a significant degree of coordination of timing of inhalation and dose release if the emerging cloud of aerosolized medicament is to be taken far enough into the lungs to provide maximum therapeutic benefit. If the patient releases the dose before inspiratory flow has been established, then a proportion of the drug is likely to be lost in the mouthpiece or the patient's mouth. Conversely, if released much after the start of inhalation, then the deeper regions of the lungs might already be full of air and not penetrated by the following bolus of released medicament aerosol.

Spacer devices have previously been devised which fit onto the mouthpiece of a pMDI in order to reduce the velocity of the emergent plume of medicament aerosol and to provide a volume in which it can expand and its propellant can evaporate more completely. This serves to avoid some of the problems of coordination and also avoids the tendency for high throat deposition caused by excessively fast drug particle inhalation. However, spacer devices are very bulky, and they can retain an excessive proportion of the drug on their walls, thereby reducing the dose that reaches the patient. Spacer devices can also be highly sensitive to electrostatic charge, which can often be strongly affected by the way in which they are washed or dried.

To overcome what can be quite a challenge for some patients, pMDI device designs have been created that employ automatic breath-actuated triggering, releasing a dose only in response to the patient's inhaled breath. The AUTOHALER™ metered dose inhaler, available from 3M Company, St. Paul, MN, and the EASIBREATHE™ inhaler, available from Teva Pharmaceutical Industries Ltd., Israel, are two such pMDI devices that use breath-actuation to attempt to better coordinate dose release with inhalation.

US20050022806 A1 discloses medicament dispensers. One embodiment shows a wire-assisting means comprising a rotatable cylinder comprising a downwardly spiraling guide track and a clutch at the centre thereof. A number of coupling wires are radially attached to the top of the cylinder, the other end of the coupling wires being attached to a fixed point of the dispenser (not shown). A guide arm is connected to a cap, the cap fitting over a medicament container which sits in a collar. Located between the bottom of the cylinder and the top of the cap is a spring. The guide arm is locatable within the guide track. As the device is activated, the coupling wires contract, causing cylinder to rotate. As it rotates, the spiraling guide track causes the guide arm to move downwards in a vertical manner, the cap causing the medicament container to move to a dispensing position.

US2002189612 A1 and US2003005926 A1 disclose medicament dispensers. As the patient inhales, a breath sensor (not shown) registers the patient's breath, completes an electrical circuit (not shown), the current from which heats a trigger coupling or in this case, a firing shape memory alloy (SMA) wire which is linked to the firing cam lock. As the SMA wire increases in temperature it contracts, and in doing so removes the firing cam lock from the firing lever. The tension spring now releases its energy and recoils upwards and pivots the firing lever downwards thus pulling the canister down relative to the valve to release a dose of medicament through the mouthpiece of the inhaler.

SUMMARY

Even though breath-actuated inhalers can be a useful aid in achieving coordination between inhalation and medicament dose release, some of the existing devices employ mechanical breath-actuation systems that typically need to be tightly toleranced in order to be both stable and yet also sensitive. The nature of stored energy mechanical breath-actuation systems is such that typically a large load of several tens of Newtons (e.g., held in a compression spring) needs to be held back (i.e., prevented from release) by a latching mechanism that has to be unlatched using only the force of the patient's breath (e.g., 1 Newton, from a reasonably sized vane). That requires a large 'mechanical advantage', whereby a small force can release a much larger one. For example, typical pMDI metering valves can require over 40 N to fire them, meaning that a compression spring to drive them needs to provide in excess of that force even after it has moved the valve by around 2-3 mm or so: i.e., it needs to provide >40 N even at the point where it has already unloaded by 2-3 mm from its compressed state at which the firing mechanism was primed (or 'cocked'). Fully mechanical systems providing such a degree of 'mechanical advantage' are typically both complex and finely tuned, which can include needing to have carefully controlled dimensions.

In order to overcome some of the above-described issues relating to inhaler "firing" mechanisms, and particularly, breath-actuated firing mechanisms, the present inventors developed the dose release firing systems of the present disclosure. These systems can provide reliable operation of an inhaler (and, e.g., a pMDI canister) to dispense a predetermined dose of medicament (e.g., in some embodiments, a metered dose of medicament in response to an electrical signal created when a patient's inspiratory breath is detected through the inhaler).

In some embodiments of the present disclosure, firing systems can be employed in combination with an electronically-triggered breath-actuation system, which can function to release (or unlatch) the firing system, allowing it to change to its fired state. In such embodiments, the addition of electronics to an inhaler can allow other functionality to be "piggy-backed" onto the triggering system electronics. For example, an electronic dose counter can be added, as can electronic timing, generation of usage reminders, etc. If electronic pressure sensors are used to detect the presence of air flow, the magnitude and potentially also the direction of inspiratory air flow through the inhaler, with logic circuit algorithms used to actuate the firing system, then there is also the possibility of recording the inspiratory flow profiles of patients, e.g. for storage and/or analysis as a means of providing the patient and/or their physician with information or advice.

Furthermore, even if patients can achieve good timing of dose release, whether via breath-actuation or simply via good press-and-breathe coordination, they can have a tendency to inhale at sub-optimal flow rates. For example, very high inspiratory flow rates (i.e., volumetric flow rates) can give rise to excessive and problematic drug deposition on the back of the throat, while very low inspiratory flow rates can lead to poor entrainment of the aerosolized medicament spray. A related additional potential problem is that very high inspiratory flow rates can lead to more rapid filling of the lungs and consequently an even greater need for good coordination.

As a result of poor inhalation and dose release coordination, many patients do not get the full therapeutic benefit of their medicinal inhalers. For example, many patients with uncontrolled asthma are unable to (i) achieve a flow rate between 10 to 50 liters/minute (L/min.); (ii) maintain the flow rate for at least 1.5 seconds; and (iii) hold their breath for at least 5 seconds after inspiration. Poor inhaler use technique has been found to correlate to poor control of asthma. Similar considerations probably apply to other respiratory diseases treated using inhaled medication, e.g. to COPD.

The general view in the guidance provided by pharmaceutical companies is that pMDI medications should be taken with patients taking a slow and deep inhalation, normally interpreted as being less than 50-60 L/min.

For conventional pMDIs and other inhalers, however, the inhalation flow rate can be poorly controlled from one user to another and even from one breath to another for the same patient. Some patients can sometimes achieve flow rates as high as 250 L/min., while others can sometimes achieve an order of magnitude less Inhaling the medicament at a lower flow rate tends to reduce drug impaction in the upper airways and increases drug deposition deeper in the lung. If a patient is unable to control their asthma, or any other respiratory disease requiring use of an inhaler, this will impact their quality of life and may lead to the requirement for further medical intervention.

Because the manner in which patients inhale through their pMDIs is an important determinant of the delivery of drug to their lungs and therefore of the benefits they obtain from their medication, the present inventors sought to control the inhalation profile.

A further difficulty arises in getting all patients to inhale in a similar and consistent manner. Inhaler designs each have their own inherent resistance (R) to air flow. This is often expressed in the units $(Pa)^{0.5}$ (min./L), and is related to inhalation air flow rate (FR) and patient-created pressure drop (PD) by the equation:

$$R = PD^{0.5}/FR.$$

Existing pMDI inhalers usually have low inherent resistances to air flow, for example below $0.5\ Pa^{0.5}$ min./L, which makes it difficult for patients to control their inhalation flowrate. Breathing profiles can be too rapid. Breath-dosing coordination can be difficult under such circumstances, and both the inter-patient and intra-patient variability can be high. With resistances of this order it can also be difficult for patients to achieve a steady flow rate of a duration of more than perhaps 2 to 2.5 seconds. Flow rate consistency during an inspiratory maneuver, and between inhalations, can be difficult to obtain. For example, flow rate 'spikes' can occur, whereby patients achieve fairly high but very transient flow rates. This can lead to poor spatial distributions of drug in their airways.

However, adding a significant fixed ('static') resistance to the design of a pMDI device also poses problems. By restricting the geometry of the air flow path in an inhaler, much higher resistances could be created, for example 1.6 $Pa^{0.5}$ min./L or more. Such resistances are typical of some DPI devices, where a high resistance is required to generate the energy needed to disperse and/or de-agglomerate a dose of medicament powder from a system without the energy content of a liquefied propellant. Unfortunately, though, while high resistances make it much easier for many patients to inhale more slowly and steadily through an inhaler, and for a longer period (e.g. 5 seconds or more), they pose an obstacle to some weaker patients who struggle to inhale adequate amounts of air against such a resistance. COPD patients, in particular, often find it difficult to inhale through such high resistances because of their impaired lung function.

In order to overcome some of the above-described issues related to either a low or a high inhaler resistance, while also avoiding the need for a spacer device, the present inventors developed the flow governors of the present disclosure, which have the ability to change their geometry and resistance to air flow as a function of pressure drop experienced, i.e., between an inlet and outlet of the flow governor. Flow governors of the present disclosure (which can also be referred to as "flow rate limiters," "flow limiters," "flow regulators," "flow limitation devices," or derivations thereof) allow appreciable air flow rates at low differential pressures, while increasing air flow resistance at higher differential pressures in order to limit the air flow rates to values more consistent with those obtained at lower differential pressures to reduce inter-patient and intra-patient inhalation variability.

Some aspects of the present disclosure provide a medicinal inhaler. The inhaler can include a housing, and an air flow path defined by at least partially the housing and including an air inlet and an air outlet. The inhaler can further include a flow governor and a breath-actuated dose release firing system. The flow governor can be positioned in the air flow path between the air inlet and the air outlet to govern air flow in the air flow path to a governing volumetric flow rate. The breath-actuated dose release firing system can be located in the housing and can be configured to release a dose of medicament at a firing volumetric flow rate less than the governing volumetric flow rate.

Other features and aspects of the present disclosure will become apparent by consideration of the detailed description and accompanying drawings.

DETAILED DESCRIPTION

Figure 1:
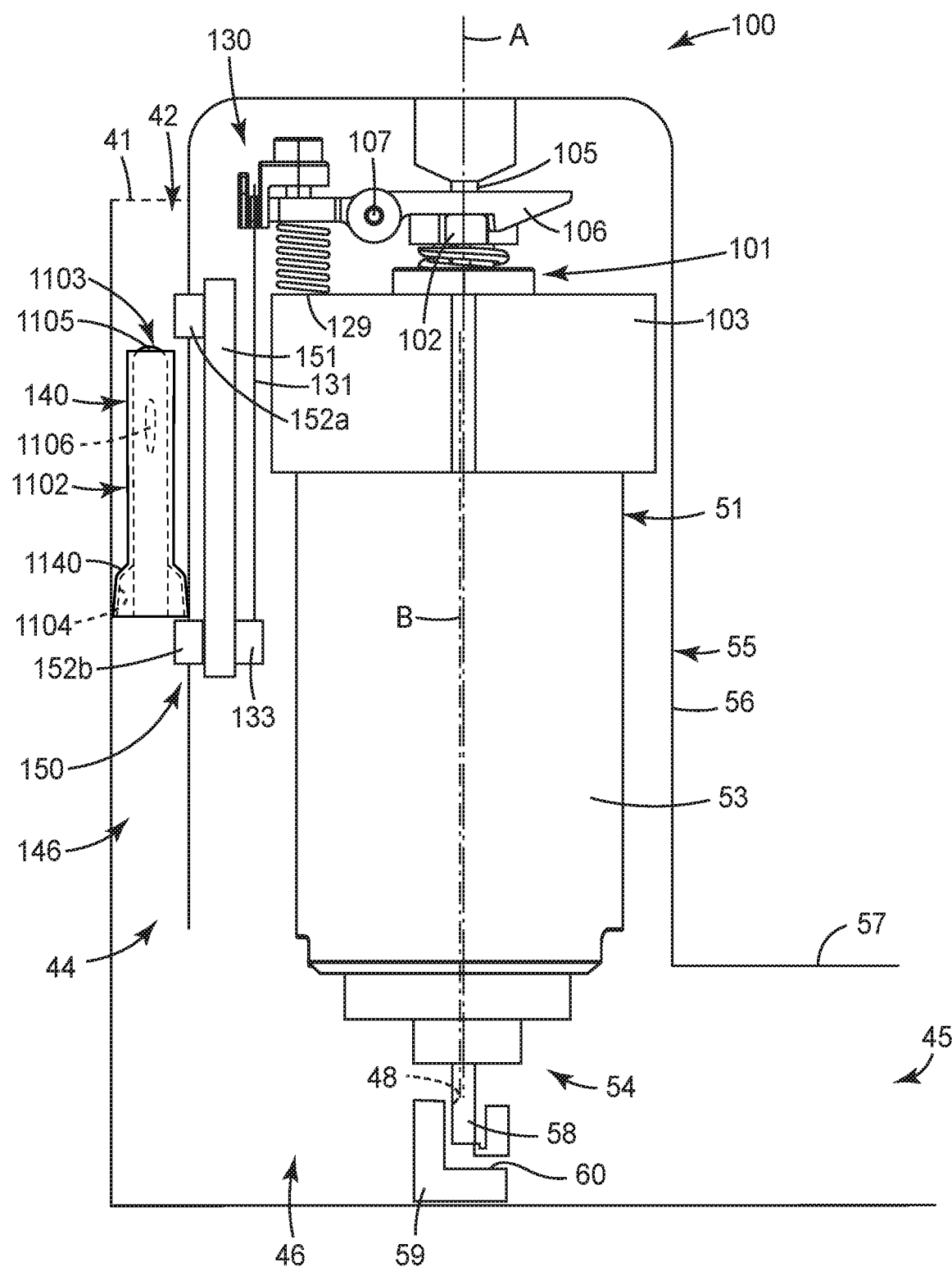
FIG. 1 is a cutaway side elevational view of a medicinal inhaler according to one embodiment of the present disclosure (with a portion of an outer housing removed so that internal components are visible), the inhaler comprising a flow governor according to one embodiment of the present disclosure, an inspiratory air flow detection system according to one embodiment of the present disclosure, and a dose release firing system according to one embodiment of the present disclosure, the firing system comprising a trigger according to one embodiment of the present disclosure that includes a shape memory material.

The present disclosure generally relates to medicinal inhalers comprising a flow governor (e.g., as part of a flow governor assembly) and a dose release firing system. Firing systems of the present disclosure can be suitable for use in various types of inhalers for the delivery of doses of medicament in the form of aerosols to the respiratory tract, including oral pulmonary inhalers and nasal inhalers. In some embodiments, the dose release firing systems of the present disclosure can be breath-actuated, responding to a patient's inhalation. For example, in some embodiments, the dose release firing system can be electronically breath-actuated, mechanically breath-actuated, or a combination thereof.

Firing systems of the present disclosure can provide the means of releasing a force sufficient to dispense a dose of medicament (e.g., a force sufficient to actuate a pMDI valve) with minimal input force. Such systems can be described as providing a mechanical advantage. As described in greater detail below, some embodiments of the present disclosure accomplish this by employing an angled bayonet mechanism to provide the mechanical advantage.

In some embodiments, dose release firing systems of the present disclosure can include:
(i) an axis (e.g., a longitudinal axis) that defines an axial/longitudinal direction that extends along or substantially parallel to the axis;
(ii) a plunger (or "canister holder" or "canister adapter") movable in the axial direction (i.e., in the inhaler, aligned with or parallel to a longitudinal direction of a canister) between a first (longitudinal) position and a second (longitudinal) position;
(iii) a stored energy device configured (and positioned relative to the plunger) to drive the plunger from the first position to the second position when stored energy in the stored energy device is released, wherein the firing system is in a primed state when the stored energy is not released (i.e., stored), and particularly, is inhibited from being released, and wherein the firing system is in a fired state when the stored energy is released;
(iv) a guideway (which can also be referred to as a "recess," a "cam path", or a "camming guide"), wherein at least a portion of the guideway has a helical shape, the guideway having a first (e.g., upper) portion having a first helix angle with respect to the axis that is greater than zero (i.e., the first portion is a helical portion of the guideway), and a second (e.g., lower) portion having a second helix angle with respect to the axis, wherein the second helix angle is less than the first helix angle; and
(v) a projection dimensioned to be received in the guideway, the projection being movable in the guideway between a first position corresponding to the first position of the plunger and a second position corresponding to the second position of the plunger, such that the projection is configured to be cammed along the guideway when the stored energy device (i.e., by stored energy being released from the stored energy device) drives the plunger to move (i.e., in the axial direction) between the first position and the second position (i.e., at least partially as the projection travels in the second portion of the guideway);
(vi) where the guideway or the projection is fixedly coupled to the plunger. (In some embodiments, the guideway or the projection can be integrally formed with the plunger.)

The guideway and the projection of such embodiments can together provide a bayonet interaction or mechanism, and particularly, in view of the first portion of the guideway, can provide an angled bayonet mechanism. The guideway can particularly be configured to transfer or convert rotary motion about an axis to more axial (e.g., linear) motion (i.e., in a direction oriented along or parallel to the axis, or at least more along or more parallel to the axis).

In some embodiments, firing systems of the present disclosure can further include a latch movable between:
(i) a first (i.e., latched) position in which the latch is coupled to at least one of the guideway and the projection to inhibit the guideway and the projection from moving relative to one another, the stored energy of the stored energy device is not released, and the firing system is in the primed state, and
(ii) a second (i.e., unlatched) position in which the latch is decoupled (i.e., released) from the guideway and the projection, such that the guideway and the projection are free to move relative to one another, the stored energy of the stored energy device is released, and the firing system is free to change to the fired state.

In some embodiments, firing systems of the present disclosure can further include a trigger (or "triggering system," or "actuation mechanism") operatively coupled to the latch and configured to change between a first state and a second state to move the latch between the first position and the second position, respectively (i.e., to allow the firing system to be fired). Various types of triggers can be employed in systems of the present disclosure, as described in greater detail below.

Firing systems of the present disclosure are particularly suitable for use in an electronically triggered, breath-actuated pMDI but could also be incorporated into a dry powder inhaler or nebulizer.

Firing systems and flow governors of the present disclosure are suitable for use in a variety of inhalers, including but not limited to, one or more of a pressurized metered dose inhaler (pMDI) (e.g., a press-and-breathe pMDI, a mechanical (i.e., mechanically triggered) breath-actuated pMDI, an electronic (i.e., an electronically triggered) breath-actuated pMDI, or a combination thereof); a dry powder inhaler (e.g., a single dose (e.g., capsule) DPI, a multi-dose (e.g., tape based, or reservoir based) DPI, or a combination thereof); a nebulizer (e.g., a pocket nebulizer); or a combination thereof.

GB Patent No. 2266466 discloses an exemplary electronically triggered breath-actuated pMDI that could be modified to incorporate a firing system and flow governor of the present disclosure. PCT Publication No. WO 2015/34709 discloses an exemplary DPI that could be modified to incorporate a firing system and flow governor of the present disclosure. PCT Publication No. WO 92/12799 discloses an exemplary pocket nebulizer that could be modified to incorporate a firing system and flow governor of the present disclosure. A firing system and a flow governor of the present disclosure can be used in any of the inhalers disclosed in GB Patent No. 2266466, PCT Publication No. WO 2015/34709, PCT Publication No. WO 92/12799 (each of which is incorporated herein by reference in its entirety), or a combination thereof.

Some embodiments of firing systems of the present disclosure can provide a means of releasing a significant amount of stored energy (e.g., stored in a stored energy device, such as a spring) to operate a pMDI canister aerosol dose dispensing mechanism in response to detection of patient inhalation through a pMDI inhaler.

Firing systems of the present disclosure can avoid the need for bulky spacer devices that are intended to reduce the need for the coordination of inhalation and manual dose actuation. When used in conjunction with data recording of flow rates and other inhaler-use events and data, firing systems of the present disclosure can also improve physician monitoring of chronically ill patients.

In some embodiments, medicinal inhalers of the present disclosure can include a flow governor assembly comprising a static air flow resistance and a dynamic air flow resistance (e.g., that varies as a function of the pressure drop experienced). In some embodiments, the flow governor assemblies of the present disclosure can include a flow governor to provide the dynamic air flow resistance, and one or more constrictions to provide the static air flow resistance.

A flow governor of the present disclosure can be adapted to change its geometry, and thereby its resistance to air flow, as a function of pressure drop between its inlet and its outlet. The flow governors of the present disclosure therefore provide a means of governing the air flow rate (i.e., volumetric flow rate) through a medicinal inhaler to reduce inter-patient and intra-patient inhalation variability and provide a more reproducible level of drug deposition in the lung. Such flow governors can provide a variable (dynamic) resistance to air flow in an air flow path of a flow governor assembly and/or medicinal inhaler.

Use of an inhaler incorporating one or more flow governors of the present disclosure could provide significant benefits to a sufferer of respiratory or other inhalation-treated disease. Apart from consistency of use and results, flow governors of the present disclosure can avoid the need for bulky spacer devices that are intended to reduce the need for such coordination. When used in conjunction with data recording of flow rates and other inhaler-use events and data, it can also improve physician monitoring of chronically ill patients. When two or more flow governors of the present disclosure are employed in a flow governor assembly and/or a medicinal inhaler, the flow governors can be arranged in parallel or in series.

In some embodiments, flow governors of the present disclosure can include (i) a tubular element that defines at least a portion of an air flow path therewithin, the tubular element comprising one or more flexible walls configured to flex (or collapse) inwardly in response to an air flow in the air flow path, and (ii) an internal support structure located within the tubular element and configured (e.g., shaped, dimensioned, positioned and having desired material properties) to preserve at least a predetermined cross-sectional area of the air flow path within the tubular element when the one or more flexible walls of the tubular element are flexed (or collapsed) inwardly. As a result, part of the air flow path cross-sectional area remains open even when the tubular element has collapsed, in order to allow the continued inhalation of air and emitted medicament. A "predetermined cross-sectional area of the air flow path within the tubular element" can include a portion of the air flow path that passes through the internal support structure, e.g., when the internal support structure includes one or more hollow portions or components, as well as a cross-sectional area of space between the tubular element and the internal support structure. The material makeup of the tubular element flexible walls can also be chosen to achieve the desired cross-sectional area between the tubular element and the internal support structure.

In some embodiments, calculation of the predetermined cross sectional area can be based on the flow resistance required to meet the governing requirements, for example, rearranging the following equation to find 'A':

$$R = \mathrm{sqrt}[0.5 * \rho * (f * 1/d + k)]/A$$

where:
  A=cross-sectional area (e.g., m$^2$)
  $\rho$=air density (e.g., kg/m$^3$)
  f=friction coefficient (dimensionless)
  l=length of wall in in the flow direction (e.g., m)
  d=tube diameter (e.g., m)
  k=singular losses coefficient (dimensionless)
  R=flow resistance (e.g., Pa$^{0.5}$*min./L)

Ensuring that the predetermined cross sectional area is maintained can be achieved through use of the internal support structure which physically inhibits the tubular element from collapsing to a point where the cross sectional area is less than the predetermined cross sectional area, and may also include a suitable selection of the material makeup of the flexible walls of the tubular element.

At low inhalation flow rates, the patient experiences a low or moderate static resistance to air flow, but when the inhalation flow rate through the flow governor exceeds a certain flow rate, the tubular element partially collapses and thus imposes an additional resistance to air flow: the inhaler changes from being a low or medium resistance inhaler to a high resistance inhaler. That is, the flow governor provides variable resistance to the assembly comprising the flow governor and/or the inhaler comprising the flow governor (or flow governor assembly).

The present inventors discovered that it can be desirable to have a combination of a static medium resistance and a large variable resistance to make it easier for the patient to inhale with a specific (e.g., target) flow rate. There can be several contributors to the static resistance of a flow governor assembly (or inhaler), such as inlets, outlets, one or more constrictions, the flow governor, other geometrical features of the air flow path, or combinations thereof. As described in greater detail below with respect to FIGS. 20-23, such a constriction can include a venturi section, a narrow passageway, a tortuous path, or a combination thereof. The constriction can be used to add a desired amount of static resistance to the assembly (or inhaler), and can be separate and independent from the flow governor. For example, the constriction can be positioned (i) at a location in the housing upstream of the flow governor, and/or (ii) at a location in the housing downstream of the flow governor, such that the constriction is outside of and separate from the flow governor, i.e., to provide a known static resistance in addition to the flow governor.

The present inventors have recognized that a critical consideration is the balance of the static and variable resistances of a flow governor assembly (or inhaler) comprising a flow governor of the present disclosure, so that the flow governor assembly (or an inhaler comprising the flow governor assembly or the flow governor) can be used by a large proportion of weaker (e.g., COPD) patients with a minimum of inter-patient and intra-patient variability in inhalation flow rate. For example, as mentioned in the 'Summary' above, air flow resistance can be calculated according to the following equation:

$$R = PD^{0.5}/FR$$

where:
- $R$ = air flow resistance (e.g., $Pa^{0.5}*(\text{min.}/L)$)
- $PD$ = pressure drop (e.g., Pa)
- $FR$ = volumetric air flow rate (e.g., L/min.)

Particularly, the present inventors discovered that at low pressure drops (e.g., 0.5 kPa), a flow governor assembly (or inhaler) having a properly balanced static and dynamic air flow resistance can exhibit a first overall air flow resistance $R_1$, based on the static resistance of the assembly (or inhaler) comprising the flow governor. At higher pressure drops (e.g., 4 kPa), the flow governor assembly (or inhaler) can exhibit a second air flow resistance $R_2$, predominantly based on the relatively large dynamic resistance provided by the flow governor. As a result, the balance of static and dynamic resistances can exhibit appropriate overall air flow resistances at both low pressure drops and high pressure drops to achieve a target governing flow rate over a range of pressure drops.

In some embodiments, the ratio of $R_2/R_1$ (e.g., at a given volumetric flow rate, or to achieve a target governing volumetric flow rate) of a flow governor assembly (or inhaler) comprising the flow governor (and optionally, further comprising a constriction to introduce a desired level of static resistance) can be at least 1.2; in some embodiments, at least 1.3; in some embodiments, at least 1.5; and in some embodiments, at least 2. In some embodiments, the ratio of $R_2/R_1$ (e.g., at a given volumetric flow rate, or to achieve a target governing volumetric flow rate) can be no greater than 3; in some embodiments, no greater than 2.9; in some embodiments, no greater than 2.8; in some embodiments, no greater than 2.7; in some embodiments, no greater than 2.5; and in some embodiments, no greater than 2.

In some embodiments, a flow governor assembly (or inhaler) comprising the flow governor can provide an overall resistance (e.g., $R_1$) to air flow of at least 0.4 $Pa^{0.5}*\text{min.}/L$ at a pressure drop (i.e., between an air inlet and an air outlet of the air flow path of the assembly (or inhaler)) of 0.5 kPa.

In some embodiments, the overall resistance to air flow can be at least 0.5 $Pa^{0.5}*\text{min.}/L$ at 0.5 kPa; and in some embodiments, at least 0.6 $Pa^{0.5}*\text{min.}/L$ at 0.5 kPa. In some embodiments, the overall resistance can be no greater than 1.2 $Pa^{0.5}*\text{min.}/L$ at 0.5 kPa; in some embodiments, no greater than 1.1 $Pa^{0.5}*\text{min.}/L$ at 0.5 kPa; in some embodiments, no greater than 1.0 $Pa^{0.5}*\text{min.}/L$ at 0.5 kPa; in some embodiments, no greater than 0.8 $Pa^{0.5}*\text{min.}/L$ at 0.5 kPa; and in some embodiments, no greater than 0.7 $Pa^{0.5}*\text{min.}/L$ at 0.5 kPa.

In some embodiments, the overall resistance (e.g., $R_2$) can be at least 1 $Pa^{0.5}*\text{min.}/L$ at 4 kPa; in some embodiments, at least 1.1 $Pa^{0.5}*\text{min.}/L$ at 4 kPa; in some embodiments, at least 1.2 $Pa^{0.5}*\text{min.}/L$ at 4 kPa; and in some embodiments, at least 1.5 $Pa^{0.5}*\text{min.}/L$ at 4 kPa. In some embodiments, the overall resistance can be no greater than 3.2 $Pa^{0.5}*\text{min.}/L$ at 4 kPa; in some embodiments, no greater than 3 $Pa^{0.5}*\text{min.}/L$ at 4 kPa; in some embodiments, no greater than 2.5 $Pa^{0.5}*\text{min.}/L$ at 4 kPa; in some embodiments, no greater than 2.2 $Pa^{0.5}*\text{min.}/L$ at 4 kPa; in some embodiments, no greater than 2.0 $Pa^{0.5}*\text{min.}/L$ at 4 kPa; and in some embodiments, no greater than 1.8 $Pa^{0.5}*\text{min.}/L$ at 4 kPa.

In some embodiments, the overall resistance to air flow at low pressure drops (e.g., 0.5 kPa), $R_1$, can range from about 1.1 to about 0.4 $Pa^{0.5}*\text{min.}/L$ (e.g., to achieve a governing flow rate ranging from about 20 L/min. to about 60 L/min.); and in some embodiments, can range from about 0.8 to about 0.6 $Pa^{0.5}*\text{min.}/L$; and in some embodiments, can range from about 0.7 to about 0.5 $Pa^{0.5}*\text{min.}/L$.

In some embodiments, the overall resistance to air flow at high pressure drops (e.g., 4 kPa), $R_2$, can range from about 3.2 to about 1.0 $Pa^{0.5}*\text{min.}/L$ (e.g., to achieve a governing flow rate ranging from about 20 L/min. to about 60 L/min.); and in some embodiments, can range from about 2.5 to about 1.5 $Pa^{0.5}*\text{min.}/L$; and in some embodiments, can range from about 2.3 to about 1.8 $Pa^{0.5}*\text{min.}/L$.

In some embodiments, medicinal inhalers of the present disclosure can include an inspiratory air flow detection (or "inspiratory flow rate detection system," or "air flow detection system," or "flow rate detection system," or derivations thereof) and/or measurement system. In some embodiments, such a detection system can include at least one pressure sensor located in the inhaler and configured to allow the inspiratory air flow rate to be sensed. For example, at least one pressure sensor can be located upstream of the flow governor in an air flow path of the medicinal inhaler. In some embodiments, such a detection system can include (i) a pressure sensor located in fluid communication with the air flow path, upstream of the flow governor, and (ii) a venturi constriction in the air flow path located adjacent where the pressure sensor is in fluid communication with the air flow path. Such a venturi constriction can speed up the local air velocity to enhance the sensitivity of the pressure sensor, allowing for less sensitive, and less costly, sensors to be employed. Such a detection system can further include a second pressure sensor located in fluid communication with the air flow path, downstream of the flow governor, such that air flow direction can be determined, i.e., in order to distinguish between inhalation and exhalation.

Some embodiments of the present disclosure provide a medicinal inhaler comprising a flow governor, a breath actuation mechanism, and an inspiratory air flow detection system.

In some embodiments of the present disclosure, the breath-actuation system can be an electronically triggered breath-actuation system. For example, the one or more pressure sensors can provide an electrical signal which is used to trigger dose release according to a defined algorithm. The dose release system may be a mechanical system, triggered by the electronic system's algorithm. Optionally, the electronic system may be housed in a reusable module, in order to reduce the overall cost of a prolonged period of treatment.

Some firing systems (e.g., which can be used in combination with flow governors of the present disclosure) can produce a small time delay between the start of inhalation and the time when the medication is released. Desirably, medication release occurs within 0.5 sec of the start of inhalation. A typical COPD patient has a tidal lung capacity of about 1.5 L. If the inhalation flow rate is limited by the flow governor to about 30 L/min., then the time of inhalation could be expected to extend to about 3-4 seconds. In reality, COPD patients may not be able to inhale for this long, due to their poor lung function, but it is anticipated that there will be sufficient time for drug to be transferred to the lung.

Some embodiments of the present disclosure provide a method of treatment of a pulmonary condition in a human patient, the method comprising: (i) providing a medicinal inhaler incorporating a flow governor comprising the tubular element and internal support structure described above; (ii) inserting a patient port of the medicinal inhaler into a body cavity (e.g., a mouth or nose); and (iii) actuating the medicinal inhaler while inhaling.

In some embodiments, the present disclosure can provide a method of using a medicinal inhaler, or of treating a pulmonary condition, which can include providing a flow governor of the present disclosure in an air flow path of the medicinal inhaler, and varying an air flow resistance of the inhaler in response to air flow in the air flow path of the flow governor. The method can further include inserting a patient port into a body cavity; and inhaling through the patient port to cause air flow in the air flow path of the flow governor. Varying the air flow resistance of the inhaler can include flexing one or more tubular walls of a tubular element of the flow governor inwardly toward an internal support structure located within the tubular element, the internal support structure configured to preserve at least a predetermined cross-sectional area of the air flow path within the tubular element when the one or more tubular walls flexes inwardly.

Definitions

The terms "a", "an", and "the" are used interchangeably with "at least one" to mean one or more of the elements being described.

The term "and/or" means either or both. For example "A and/or B" means only A, only B, or both A and B.

The terms "including," "comprising," or "having," and variations thereof, are meant to encompass the items listed thereafter and equivalents thereof as well as additional items.

Unless specified or limited otherwise, the terms "connected" and "coupled" and variations thereof are used broadly and encompass both direct and indirect connections and couplings. Further, "connected" and "coupled" are not restricted to physical or mechanical connections or couplings.

The term "flexible" is used to refer to a material and/or structure that collapses or significantly deforms in response to an air pressure differential existing across the material and/or structure in its typical mode of operation. The term 'rigid' is used to refer to a material and/or structure that does not collapse or significantly deform under the forces it experiences in its typical mode of operation. For example, the tubular element of flow governors that can be used in combination with firing systems of the present disclosure is generally flexible and deformable in its normal operation, whereas the internal support structure of such flow governors is generally rigid or non-deformable in its normal operation.

The term "tubular" is used to refer to a hollow structure having one or more walls that define an open passageway therein. In some embodiments, the term "tubular" can more specifically refer to elongated hollow structures. Tubular structures of the present disclosure can have any cross-sectional shape desired (i.e., transverse cross-sectional shape—taken substantially orthogonally with respect to a longitudinal axis of the tubular structure), including, but not limited to, one or more of circular, elliptical or oblong (i.e., having a longer major axis and a shorter minor axis), triangular, rectangular, square, trapezoidal, polygonal, star-shaped, D-shaped, other suitable cross-sectional shapes, or a combination thereof. In some embodiments, tubular structures of the present disclosure can have a circular cross-sectional shape.

The term "non-mechanical energy" generally refers to any energy type that is not mechanical energy, and in some embodiments, can include, but is not limited to, at least one of heat energy, electrical current energy, electrical field energy, magnetic field energy, and a combination thereof.

As used herein, the term "annular" or derivations thereof can refer to a structure having an outer edge and an inner edge, such that the inner edge defines an opening. For example, an annular structure can have a circular or round shape (e.g., a circular ring) or any other suitable shape, including, but not limited to, triangular, rectangular, square, trapezoidal, polygonal, etc., or combinations thereof. Furthermore, an "annulus" of the present invention need not necessarily be symmetrical, but rather can be an asymmetrical or irregular shape; however, certain advantages may be possible with symmetrical and/or circular shapes.

The present disclosure will be described with respect to particular embodiments and with reference to certain drawings, but the invention is not limited thereto. The drawings described are only schematic and are non-limiting. In the drawings, the size of some of the elements may for illustrative purposes be exaggerated and not drawn to scale. Where possible, analogous features in different embodiments have generally been denoted by similar numerals (e.g., 130, 230, 330, or 1100, 1200, etc.).

FIG. 1 illustrates an inhaler 100 according to one embodiment of the present disclosure. The inhaler 100 includes a dose release firing system 101 according to one embodiment of the present disclosure, comprising a trigger (or triggering system) 130 according to one embodiment of the present disclosure. The inhaler 100 is further illustrated by way of example only as including a flow governor 140 according to one embodiment of the present disclosure, and an inspiratory air flow detection system 150 (or "inspiratory flow rate detection system," or "air flow detection system," or "flow rate detection system," or derivations thereof) according to one embodiment of the present disclosure. However, it should be understood that inhalers or the present disclosure need not include a flow governor or inhalation air flow detection system.

FIGS. 2-15 illustrate various details of the firing system 101. FIGS. 16-19 illustrate other embodiments of triggers that can be employed with firing systems of the present disclosure. FIG. 20 illustrates another embodiment of a medicinal inhaler of the present disclosure, comprising an adapter positioned between a firing system and a medicament canister.

The overall function and various components of the inhaler 100 of FIG. 1 will now be described before turning to the details of the firing system 101.

As shown in FIG. 1, the inhaler 100 is shown by way of example only as being a pressurized metered dose inhaler (pMDI) comprising a canister 51 containing a medicament formulation, the canister comprising a can 53 sealed with a metering valve 54. The canister 51 sits within a housing (or "actuator") 55 comprising a tubular sleeve portion 56 dimensioned to receive the canister 51, and a portion in the form of an open tubular patient port 57 in the form of a mouthpiece that defines an inspiration orifice (or an air outlet) 45. Such a patient port of an inhaler is sometimes referred to herein as a "mouthpiece" for simplicity. However, it should be understood that such mouthpieces can instead be configured to be nosepieces of nasal inhalers and that the present disclosure can equally apply to nasal inhalers even where not specifically mentioned herein.

A stem portion 58 protrudes from the metering valve 54 and is located and retained by friction in a stem socket 59 formed as an integral part of the housing 55 by way of example only. As shown in FIG. 1, a spray orifice 60 can be formed in the stem socket 59, and can provide a passage for fluid communication between the valve stem portion 58 and the inspiration orifice 45. In use, a patient can place the patient port (e.g., mouthpiece) 57 into a body cavity (e.g., mouth) and then inhales through it. However, in the case of nasal pMDIs, it is not always necessary to inhale.

In some embodiments employing a press-and-breathe pMDI, the patient can inhale through the patient port 57 while at the same time pressing downwards on a protruding base of the canister 51. In such embodiments, the pressing force serves to move the canister 51 downwards relative to the valve's stem portion 58. That relative movement between the canister 51 and the valve's stem portion 58 serves to actuate the canister valve 54 to isolate a metered dose of medicament formulation from the bulk formulation in the canister 51 and then to discharge it via a hollow bore 48 formed in the stem portion 58. The discharged dose then passes along the fluid passageway through the stem socket 59 and the spray orifice 60 and emerges in the form of a fine respirable spray that passes through the patient port 57 into the patient's body cavity (e.g., oral cavity and/or nasal cavity) and thence into their respiratory passages, thereby treating their disease.

As the patient inhales on the patient port 57, i.e. as they reduce the air pressure in their own respiratory passages and oral cavity and in the patient port 57 via outward movement of their chest wall and downwards movement of their diaphragm, an air flow is set up through the inhaler 100. Air from the atmosphere external to the inhaler, i.e., ambience, is drawn into the inhaler 100 via an air flow path 46 of the inhaler 100.

In some embodiments, as shown in FIG. 1, employing a breath-actuated pMDI, and particularly, an electronic (or electronically triggered) breath-actuated pMDI, the inhaler 100 can further include the firing system 101 (e.g., the breath-actuated firing system 101) in combination with the inspiratory air flow detection system 150. In such embodiments, the firing system 101 can provide sufficient force to actuate the canister valve 54, i.e., to move the canister 51 downwards relative to the valve's stem portion 58 to release (i.e., dispense) a dose of medicament.

In some embodiments, the inspiratory air flow detection system 150 can include a controller 151 and one or more pressure sensors 152a, 152b that provide an electrical signal that is used to activate the trigger 130 to trigger the dose release firing system 101 to release a dose of medicament according to a defined algorithm. Optionally, the inspiratory air flow detection system 150 and/or the electrical signal generation system may be housed in a reusable module, in order to reduce the overall cost of a prolonged period of treatment.

Generally, the controller 151 can be a suitable electronic device, such as, for example, a programmable logic controller ("PLC"), a programmable circuit board ("PCB"), a microprocessor, and/or other suitable devices or structures. As such, the controller 151 may include both hardware and software components, and the term "controller" is meant to broadly encompass the combination of such components.

In some embodiments, it can be important that the inspiratory flow rate (i.e., volumetric flow rate) at which the firing system 101 triggers is not set too low, to avoid the risk that the breath-actuated inhaler device might operate accidentally or that it will deliver the medicament at too low an inhalation rate for adequate therapeutic effect. It can also be important that the triggering flow rate for the firing system 101 is not set so high that a poorly inhaling patient (e.g., a weak COPD patient) is not able to reach the triggering flow rate.

Furthermore, as shown by way of example only, in some embodiments, the inhaler 100 can further include the flow governor 140 in combination with the firing system 101. The flow governor 140 can allow appreciable air flow rates at low differential pressures, while increasing air flow resistance at higher differential pressures in order to limit the air flow rates to values more consistent with those obtained at lower differential pressures, in order to reduce inter-patient and intra-patient inhalation variability for the inhaler 100.

In some embodiments, the dose release firing system 101 can be controlled by the inspiratory air flow detection system 150, such that the firing system 101 is triggered to release a dose of medicament at a triggering flow rate, i.e., an inspiratory air flow rate, that is less than a governing flow rate of the flow governor 140. That is, the flow governor 140 can be configured to govern air flow rate in the inhaler 100 to a desired air flow rate (i.e., the flow governor 140 can change its geometry in response to the pressure drop it experiences), and the triggering flow rate for the firing system 101 can be set to be lower than the governing flow rate. As a result, when the flow governor 140 and the firing system 101 are used in combination in the same inhaler 100, the firing system 101 can be appropriately triggered at an air flow rate that is not prohibited by the flow governor 140.

Said another way, the triggering flow rate of the firing system 101 needs to be below the governing air flow rate, in order that the latter does not prevent the triggering flow rate from being achieved. For example, in some embodiments, the target triggering flow rate of the inhaler 100 (e.g., of the firing system 101) can be 15 liters/minute (L/min.), and the target governing flow rate can be 30 L/min. Manufacturing tolerances can be maintained such that the inhaler 100 has an actual triggering flow rate of significantly less than its governing flow rate. In reality, a "target governing flow rate" may actually include a range of flow rates, as described in the Examples section with reference to FIGS. 39 and 40, such that the target governing flow rate may actually be a target range of flow rates. Environmental factors such as temperature and atmospheric pressure will tend to broaden the range of values actually obtained, but nevertheless actual triggering flow rates might for example vary between 10 L/min. and 20 L/min., and actual governing flow rates might for example vary between 25 L/min. and 35 L/min.

By way of example only, the flow governor 140 is shown as including an outer flexible tubular element (or "tube") 1102 comprising at least one flexible wall 1140, and an internal support structure 1103 that is dimensioned to be received within the tubular element 1102 (i.e., within the at least one flexible wall 1140). In some embodiments, the internal support structure 1103 can include a hollow base 1104, two hollow (e.g., tubular) pillars 1105 (only one of which is visible in FIG. 1) and a cross member 1106 connecting the pillars 1105. Due to the collapsible tubular element 1102 and internal support structure 1103 at least partially positioned within the tubular element 1102, the flow governor 140 is configured to govern air flow by changing its geometry, and thereby its resistance to air flow, as a function of pressure drop between its inlet and its outlet.

Additional details regarding flow governors that can be employed in combination with firing systems of the present disclosure, in inhalers of the present disclosure, can be found in PCT Publication Nos. WO2017/112748 and WO2017/112452, each of which is incorporated herein by reference in its entirety. The specific flow governor 140 shown in FIG. 1 is shown by way of example only and is described in greater detail below with respect to FIGS. 22-27, and it should be understood that other flow governors can be employed in combination with firing systems of the present disclosure, in inhalers of the present disclosure, without departing from the spirit and scope of the present disclosure.

The flow governor 140 can be positioned in fluid communication with the air flow path 46 of the inhaler 100, and particularly is shown in FIG. 1 by way of example only as being positioned in a dedicated flow governor air flow path 146 positioned in fluid communication with (and thus forming a portion of) the air flow path 46, and thus, in fluid communication with the inspiration orifice 45 of the inhaler 100. Particularly, the inhaler 100 is configured such that inspiratory air necessarily flows through the dedicated air flow path 146 to be governed by the flow governor 140. As shown in FIG. 1, the inhaler 100 can include an air inlet 42, which can define an aspiration orifice, through which air can be drawn into the dedicated air flow path 146, past and/or through the flow governor 140, toward and out of the inspiration orifice 45. In some embodiments, the air inlet 42 can include a grill, screen or grate 41 positioned to inhibit debris from entering the air inlet 42. The dedicated air flow path 146 can further include an air outlet 44 positioned to connect the dedicated air flow path 146 with the rest of the inhaler 100, and particularly, with the inspiration orifice 45.

As shown in FIG. 1, the one or more pressure sensors 152a, 152b can be located in fluid communication with the dedicated air flow path 146. The first pressure sensor 152a can be located upstream of the flow governor 140. The pressure sensors 152a, 152b can be connected to the controller 151, all of which can be powered by a suitable power source with an appropriate switch to provide a power on/off function. When the power is switched on, the pressure sensor 152a can determine the atmospheric pressure. When the patient inhales air through the inhaler 100, causing air to flow out of the air outlet 44, air flows into the air flow path 146 via the air inlet 42, and the pressure sensor 152a detects and/or measures the dynamically changing air pressure brought about by the patient's inspiratory effort in conjunction with the functionality of the flow governor 140.

Detection of pressure changes, relative to the initial atmospheric pressure, via cooperation between the pressure sensor 152a and the controller 151, can be used to calculate the air flow rate past the pressure sensor 152a. (The air flow rate causes a reduction in local air pressure, via the Bernoulli Effect.) When a desired pre-determined flow rate is reached, an electronic signal can be used to enable the firing system 101 to automatically actuate the inhaler 100. Alternatively, the electrical signal can be sent to a suitable component, such as a Light Emitting Diode (LED) or Liquid Crystal Display (LCD) or audio speaker, to provide a cue for the user to actuate the inhaler 100 (e.g., in a mechanically triggered firing system).

Furthermore, in some embodiments, the second pressure sensor 152b can be included in the air flow path 146 towards the air outlet 44 (i.e., downstream of the flow governor 140). The presence of this second pressure sensor 152b can be used to determine air flow direction via comparison of the relative local air pressures at the two pressure sensors 152a, 152b (e.g., performed by the controller 151), which can be used to distinguish inspiration from exhalation (e.g., if a patient blows into the inhaler 100 instead of sucking air through the inhaler 100). This can allow a linked breath-actuation mechanism (e.g., the firing system 101) to be arranged not to operate if the patient breathes out into the inhaler, rather than in through it, the two breathing modes being easily differentiated by the different relative pressure drop relationships detected by the first and second sensors 152a and 152b.

Inclusion of two pressure sensors 152a, 152b in fluid communication with the air flow path 146 enables measurement (in conjunction with the appropriate electrical components, e.g., the controller 151, power source, etc.) of pressure changes, which can be correlated with air flow rates. When a predetermined flow rate is achieved, this can prompt a signal to trigger the firing system 101 to actuate the inhaler canister valve 54. Such a mechanism can negate the requirement for the patient to coordinate inhaling and actuating the inhalation device. In addition, the triggering flow rate can be programmed differently for different products. In each case, though, use of an integral flowmeter (which the pressure sensors 152a, 152b can effectively be) and electronic actuation can ensure that the inhaler 100 can be actuated at an appropriate time in the patient's inspiratory maneuver. The electronic circuitry involved can also be configured to allow each triggering event to be counted and recorded, and can be used to also provide a dose count, e.g. for display to the patient of the theoretical number of doses thus still remaining.

As well as using the pressure measurements and the calculated flow rate data to trigger canister actuation (i.e., dose release firing), such a system can optionally be configured to provide feedback to the patient and to their physician.

The air flow path 146 containing the flow governor 140 can be incorporated, in a similar fashion as already described, into any of the variety of inhalers mentioned above. It should also be understood that the dedicated air flow path 146 is shown by way of example only, and that in some embodiments, an air inlet can be formed in an upper portion of the housing 55, and the flow governor 140 can be positioned in fluid communication with such an air inlet to govern air flow rates through the inhaler 100. For example, in some embodiments, the flow governor 140 can be positioned in a cap that is coupled to an open upper end of the housing 55.

In some embodiments, no matter which type of inhaler is employed, the air flow path 146 including the flow governor 140 and one or more of the pressure sensors 152a, 152b, the controller 151, and any other relevant electrical components, can be manufactured as a separate part or component, or as a portion of the inhaler 100. Exemplary flow governor assemblies comprising flow governors that can be separately formed and put in fluid communication with or otherwise incorporated into an inhaler, or that can form a portion of an inhaler of the present disclosure, are described in greater detail in PCT Publication No. WO2017/112748.

Dose Release Firing System

Figure 11:
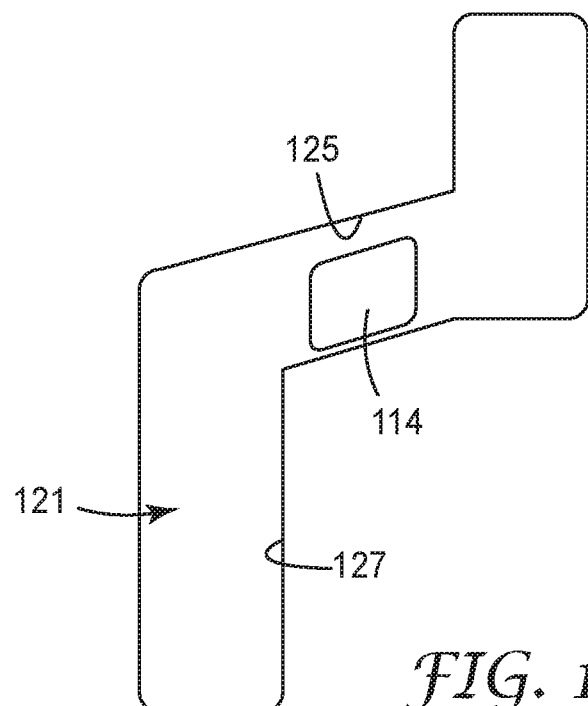
FIG. 11 is a schematic side 'un-rolled' flat view of the guideway of FIGS. 4, 5, and 8-10, the projection of FIGS. 3 and 6-10 shown positioned in the guideway in a first position, when the firing system of FIGS. 1-3 and 10 is in its primed state.
Figure 12:
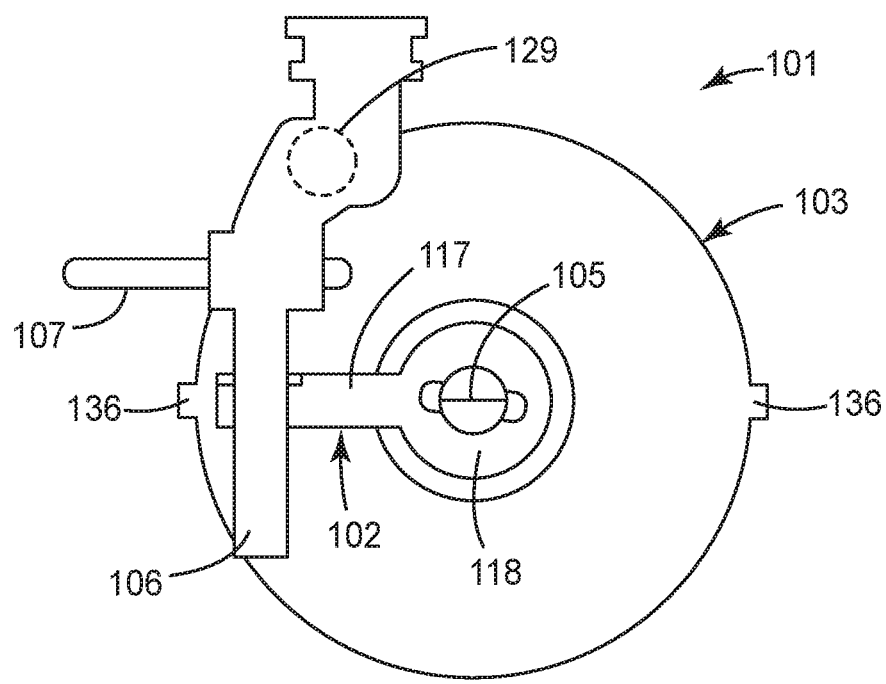
FIG. 12 is a top plan view of the firing system of FIGS. 1-3 and 10 when in its primed state.
Figure 13:
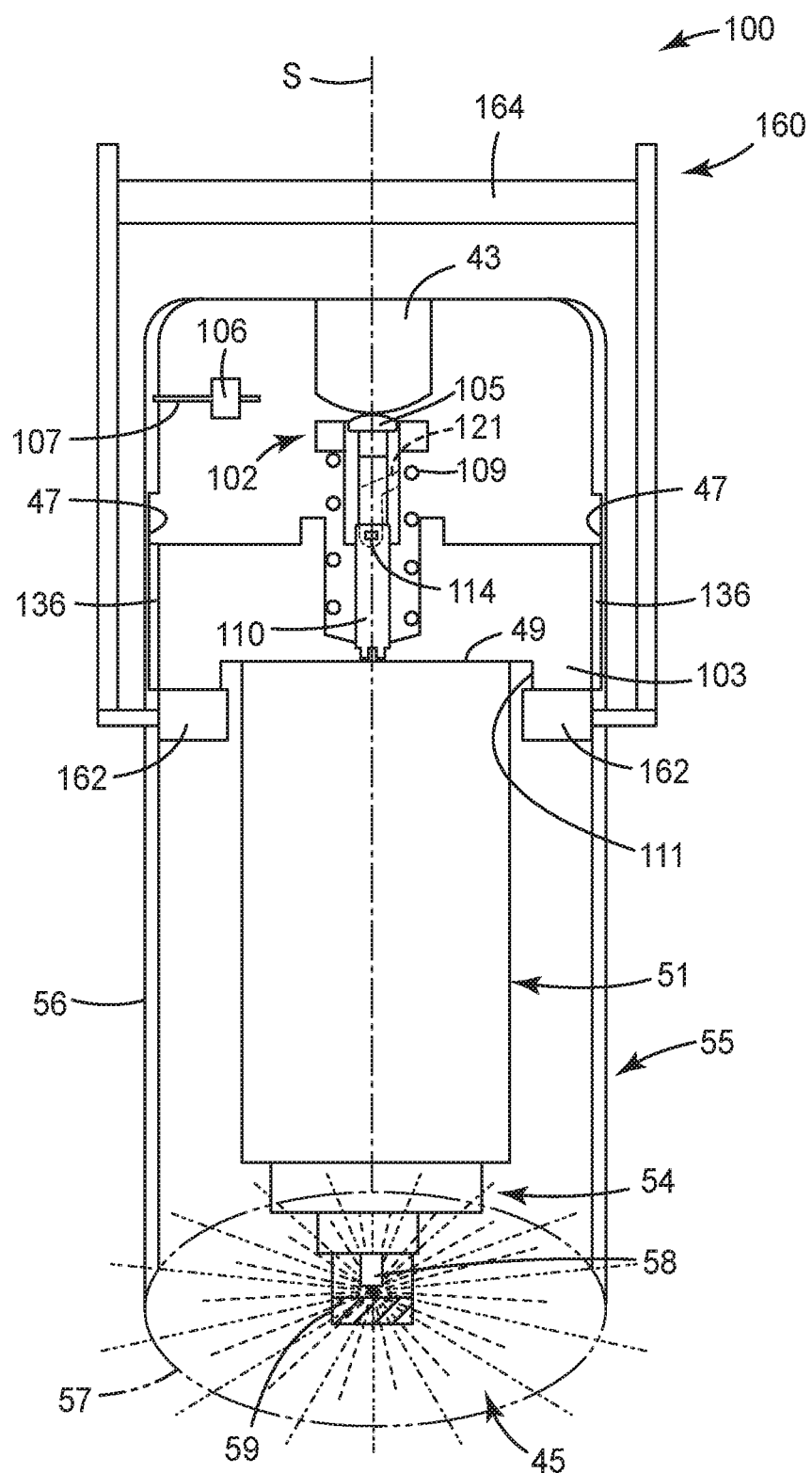
FIG. 13 is a partial schematic side cross-sectional view of the medicinal inhaler of FIGS. 1 and 10, shown in the same orientation as FIG. 10, the firing system being shown in its fired state.
Figure 14:
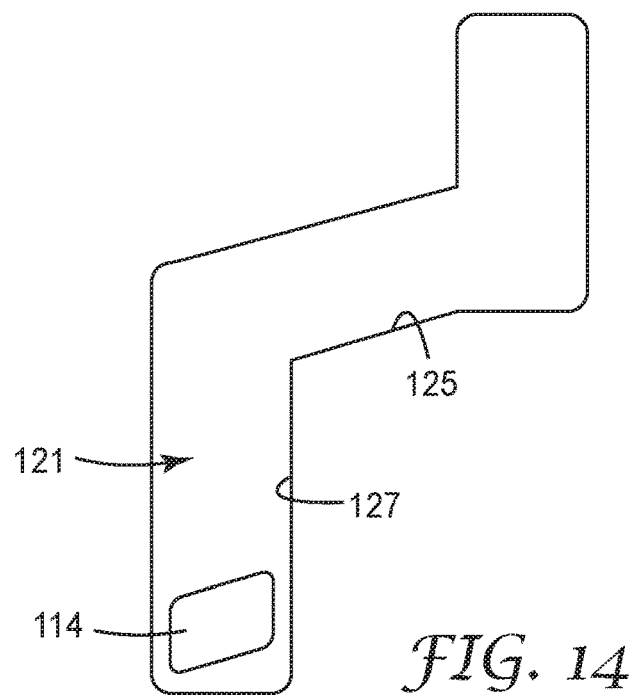
FIG. 14 is a schematic side 'un-rolled' flat view of the guideway of FIGS. 4, 5, 8-11 and 13, the projection of FIGS. 3, 6-11, and 13 being shown positioned in the guideway in a second position, when the firing system of FIGS. 1-3 and 12-13 is in its fired state.
Figure 15:
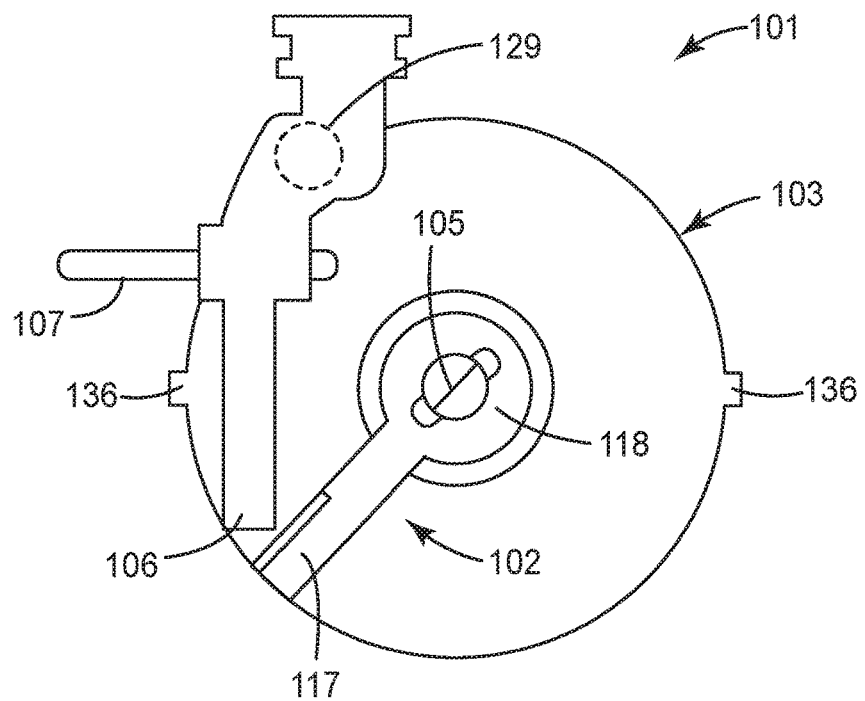
FIG. 15 is a top plan view of the firing system of FIGS. 1-3, 10 and 12-13 when in its fired state.

As mentioned above, FIGS. 2-15 illustrate various details of the firing system 101. FIGS. 1-3, 8 and 10-12 show aspects of the firing system 101 in a primed state, and FIGS. 13-15 show aspects of the firing system 101 in a fired state.

Additional details regarding dose release firing systems that can be employed in medicinal inhalers of the present disclosure are described in PCT Publication No. WO2017/112476, which is incorporated herein by reference in its entirety. Some embodiments of the firing systems of the present disclosure can further include an auto-reset mechanism, such as those described in PCT Publication No. WO2017/112451, which is incorporated herein by reference in its entirety.

The firing system 101 includes an axis (e.g., a longitudinal axis) A (see FIGS. 1-3); a rotary arm module 102 rotatable about the axis A; a plunger (or "canister holder") 103, configured to be operatively coupled to the medicament canister 51, which is movable in the axial direction between a first (e.g., primed) position and a second (e.g., fired) position; a convex circular spacer 105; a latch 106 pivotal about a pin 107, which can be connected to the inhaler housing 55 (see, e.g., FIG. 10); a firing pin 110; and a stored energy device 109 configured (and positioned relative to the plunger 103) to drive the plunger 103 from the first position to the second position when stored energy in the stored energy device is released. The firing system 101 can be referred to as being primed (or cocked) or in a primed (or cocked) state when stored energy in the stored energy device 109 is not released and as being fired or in a fired state when the stored energy is released.

It should be noted that the inhaler 100 of FIG. 1 is a pressurized metered dose inhaler (pMDI), and that the firing system 101 operates to release a dose from the inhaler 100 by actuating the valve 54 of the canister 51. Particularly, the stem portion 58 of the valve 54 is held stationary relative to the housing 55 by the stem socket 59, and the can 53 is movable with respect to the valve 54, such that the canister 51 can be described as being movable along the axis A, or in the axial direction, in response to the movement of the plunger 103 to cause a dose to be released from the inhaler 100. However, as mentioned above, the firing system 101 can be employed in a variety of inhalers, and need not be employed in a pMDI. As a result, in embodiments in which the firing system 101 is employed in a different type of inhaler that does not employ the canister 51, the plunger 103 need not be configured to be operatively coupled to the canister 51.

In some embodiments, the first stored energy device 109 can include a biasing element (e.g., a spring), which is shown as a coil spring, and particularly, a compression spring, by way of example only in the illustrated embodiment. However, stored energy devices of the present disclosure can include, but are not limited to, one or more of biasing elements (e.g., springs), propellants, chemicals, motors, electrical devices, and combinations thereof. In embodiments in which the stored energy device 109 includes a biasing element, the firing system 101 can be held under load, e.g., against the bias of the biasing element, when in its primed state.

The stored energy device 109 is configured such that the force provided by the energy released from the stored energy device 109 is sufficient to overcome any force necessary to actuate the canister valve 54, e.g., the spring force in the pMDI canister valve 54 of FIG. 1. For example, in some embodiments, the stored energy device 109 can provide 40 N in its unreleased (e.g., compressed state), i.e., with the device 'cocked' ready to trigger, in order to provide adequate force to operate the valve 54 (i.e., to move it to its firing position). That is, in some embodiments, the stored energy device 109 can provide at least 40 N of force when the stored energy is released; in some embodiments, at least 50 N; and in some embodiments, at least 60 N.

Figure 2:
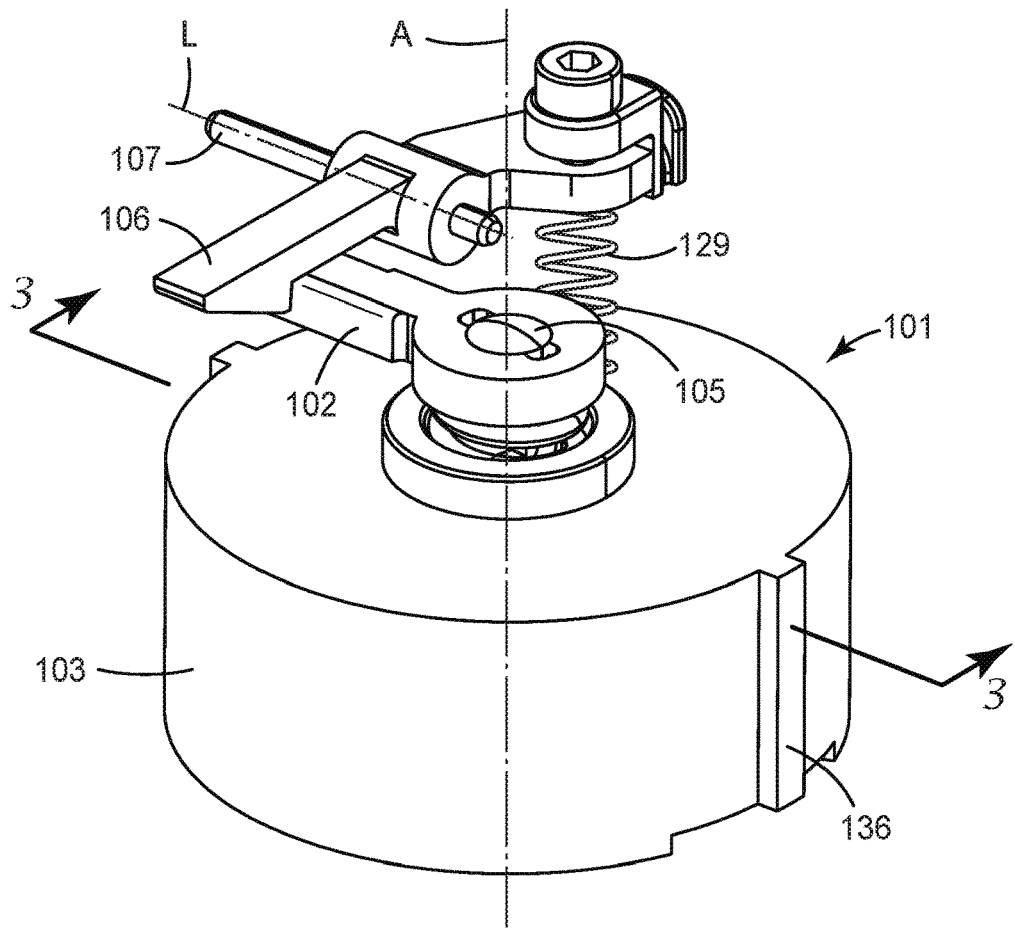
FIG. 2 is an isometric view of the firing system of FIG. 1.

As shown, the plunger 103 is movable in the axial direction (e.g., along the axis A) with respect to the housing 55 and the canister 51 (i.e., in the inhaler 100, aligned with or parallel to a longitudinal direction of the canister 51) between a first (longitudinal or axial) position (e.g., a primed position) and a second (longitudinal or axial) position (e.g., a fired position) to actuate the dose release valve 54 of the canister 51. That is, the plunger 103 can be configured to move the medicament canister 51 along its longitudinal axis B (see FIG. 1) between a first position in which a medicament dose is not released and a second position in which a medicament dose is released, respectively. In addition, the plunger 103 can be rotationally fixed (e.g., with respect to the housing 55) about the axis A. For example, in some embodiments, the plunger 103 and the housing 55 can include inter-engaging features that inhibit the plunger 103 and the housing 55 from rotating relative to one another about the axis A. By way of example, as shown in FIG. 2, in some embodiments, the plunger 103 can include one or more ribs 136 (see FIGS. 2-3, 10, 12, 13 and 15), e.g., a set of diametrically opposed ribs 136, each dimensioned to be received in a mating recess 47 (see FIGS. 10 and 13) formed in an inner surface of the housing 55, or vice versa. That is, in some embodiments, the plunger 103 can alternatively or additionally include one or more recesses dimensioned to receive one or more ribs or projections from the housing 55.

Figure 3:
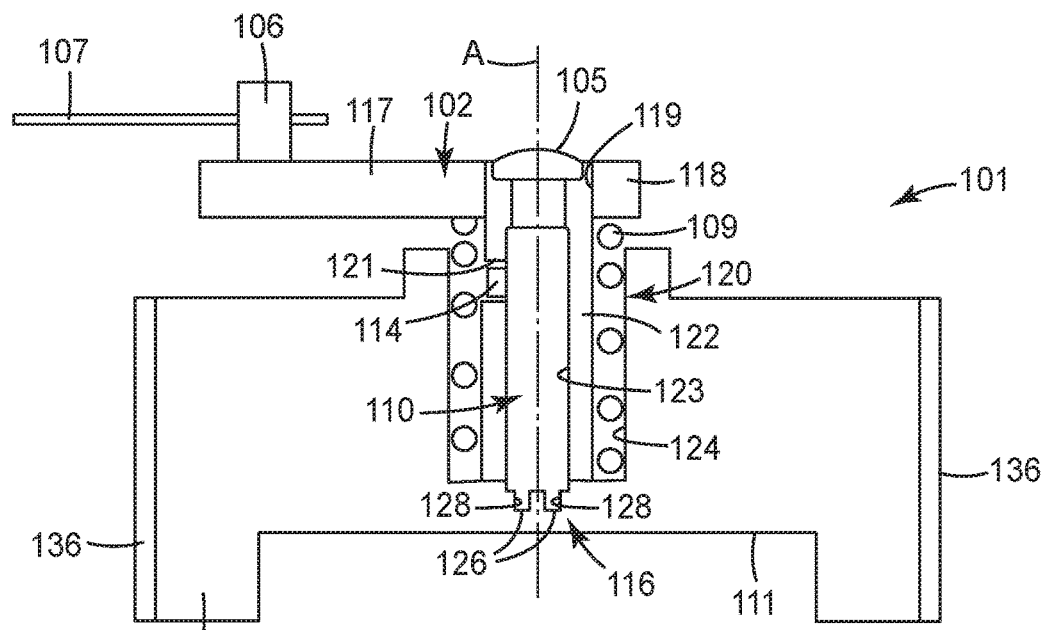
FIG. 3 is a schematic side cross-sectional view of the firing system of FIGS. 1 and 2, taken along line 3-3 of FIG. 2, shown rotated 90 degrees about a longitudinal axis relative to the side cross-sectional view shown in FIG. 1, the firing system comprising a firing pin and a rotary arm module.
Figure 10:
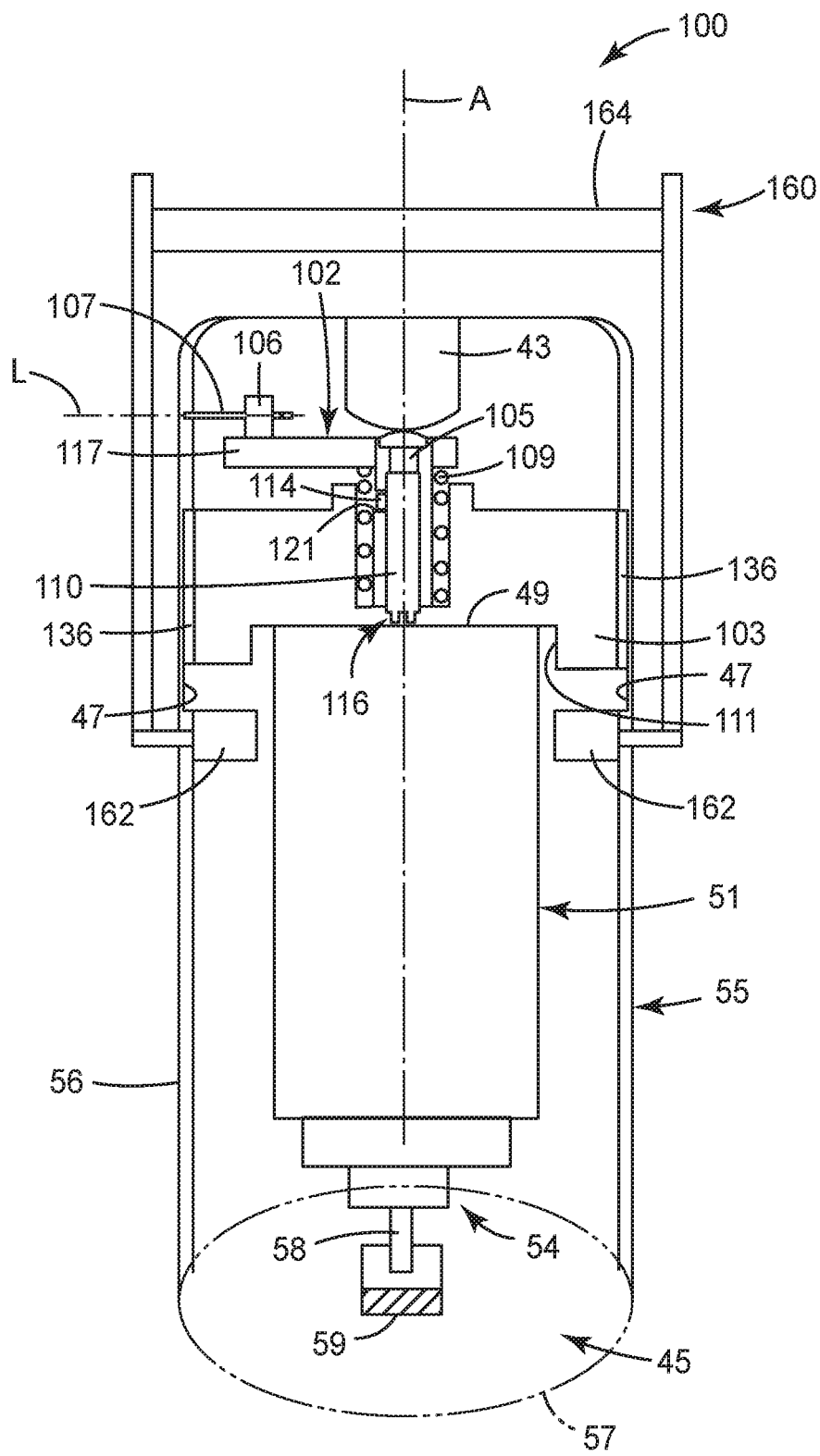
FIG. 10 is a partial schematic side cross-sectional view of the medicinal inhaler of FIG. 1, shown rotated 90 degrees about a longitudinal axis with respect to the side view shown in FIG. 1, the firing system shown in its primed state.

As shown in FIG. 3, in some embodiments, the plunger 103 can include a first (e.g., lower) recess 111 dimensioned to receive at least a portion of the canister 51 (e.g., at least a portion of a base 49 of the canister 51, opposite the end comprising the dose release valve 54), as shown in FIGS. 10 and 13. As such, in some embodiments, the plunger 103 can be directly coupled to the canister 51.

As further shown in FIG. 3, in some embodiments, the plunger 103 can include a second (e.g., upper) recess 124 dimensioned to receive at least a portion of the rotary arm module 102, the firing pin 110, and the stored energy device 109. In some embodiments, as shown, the second recess 124 can have a cylindrical shape in the absence of the firing pin 110 and can have a tubular shape in the presence of the firing pin 110.

Figure 4:
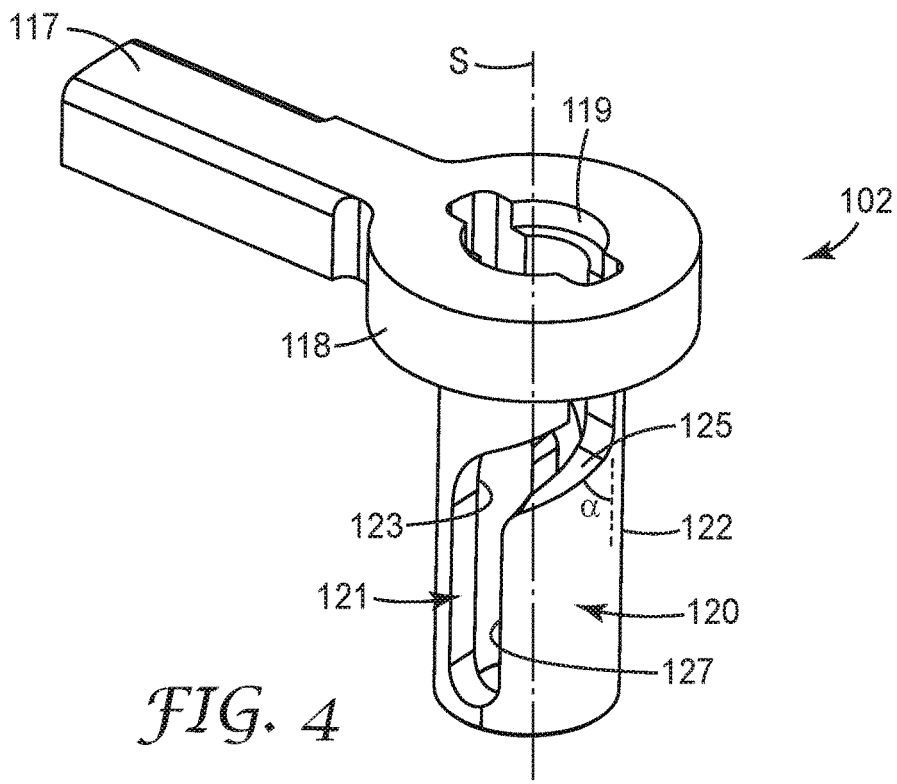
FIG. 4 is a top isometric view of the rotary arm module of the firing system of FIGS. 1-3, the rotary arm module comprising a guideway.
Figure 5:
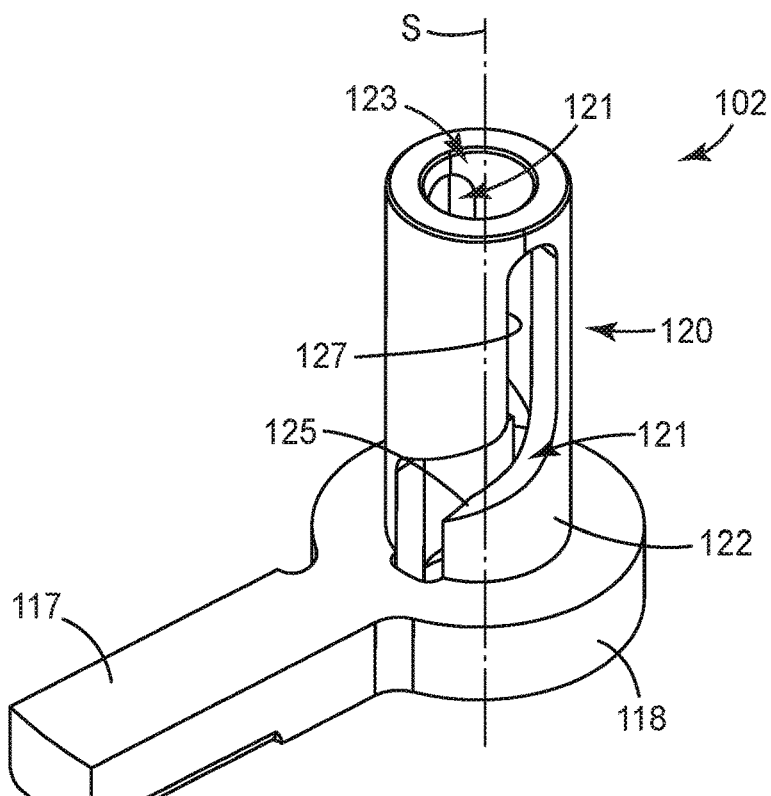
FIG. 5 is a bottom isometric view of the rotary arm module of FIG. 4.
Figure 6:
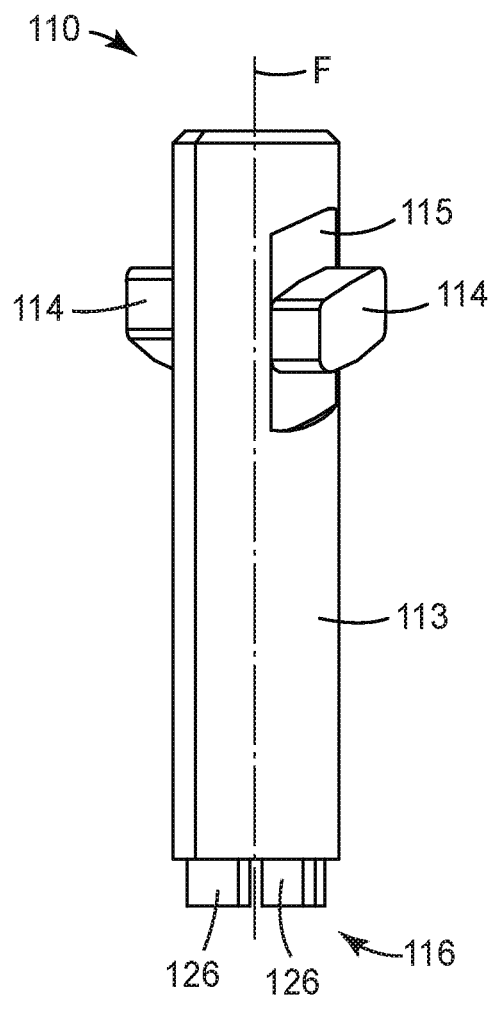
FIG. 6 is an isometric view of the firing pin of the firing system of FIGS. 1-3, the firing pin comprising a projection dimensioned to be received in the guideway of the rotary arm module.
Figure 7:
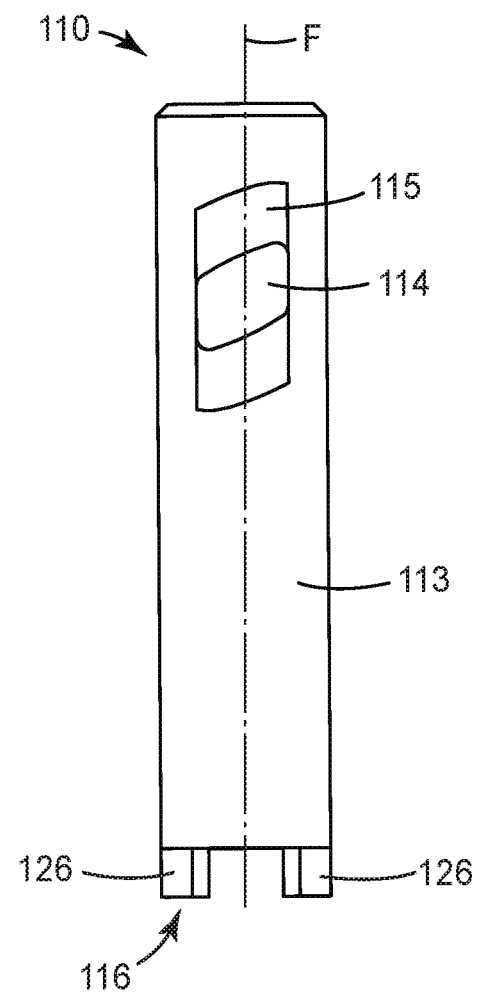
FIG. 7 is a side elevational view of the firing pin of FIG. 6.
Figure 8:
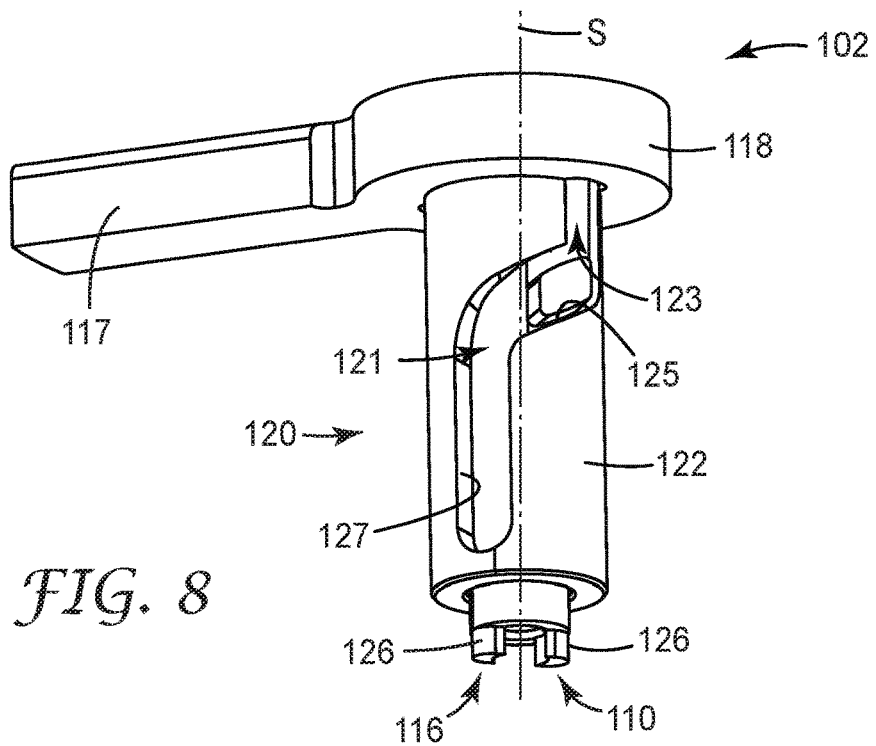
FIG. 8 is an isometric view of the rotary arm module of FIGS. 4 and 5 and the firing pin of FIGS. 6 and 7, assembled, the firing pin shown in a first position with respect to the rotary arm module, such that the projection is shown in a first position with respect to the guideway.
Figure 9:
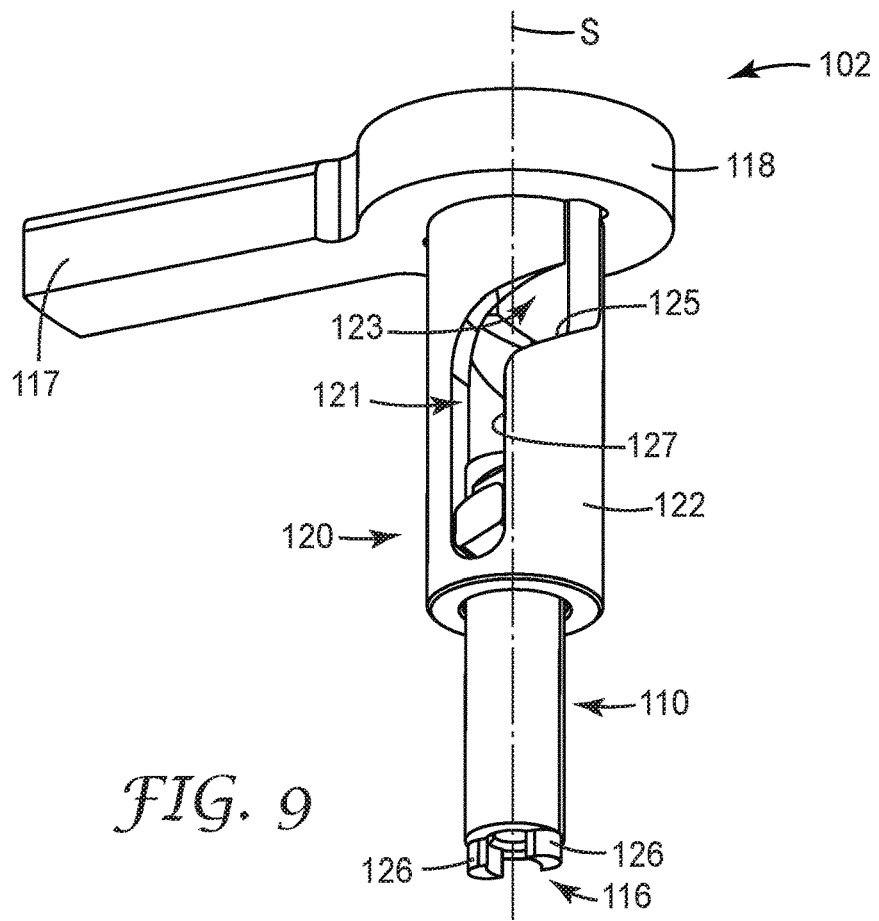
FIG. 9 is an isometric view of the rotary arm module of FIGS. 4, 5 and 8 and the firing pin of FIGS. 6-8, assembled, the firing pin shown in a second position with respect to the rotary arm module, such that the projection is shown in a second position with respect to the guideway.

FIGS. 4-5 illustrate the rotary arm module 102 in greater detail; FIGS. 6-7 illustrate the firing pin 110 in greater detail; and FIGS. 8-9 illustrate in greater detail how the rotary arm module 102 and the firing pin 110 interact.

The rotary arm module 102 is shown and described herein as one example for providing a guideway 121 of the present disclosure. The firing pin 110, at least a portion of which is dimensioned to be received within the rotary arm module 102, is shown and described herein as one example for providing a projection 114 of the present disclosure dimensioned to be received in and movable in the guideway 121. However, it should be understood that other suitable structures can be employed for providing the guideway 121 and the projection 114 of the present disclosure. As mentioned above, either the guideway 121 or the projection 114 can be fixedly coupled to the plunger 103, and in some embodiments, can be integrally formed with the plunger 103. The guideway 121 and the projection 114 can be rotatable with respect to one another about the axis A, and can be further translatable with respect to one another along, or substantially parallel to, the axis A. In the embodiment illustrated in FIGS. 2-15, the firing pin 110 includes the projection 114 and is fixedly coupled to the plunger 103, and the rotary arm module 102 (and accordingly, the guideway 121) is rotatable about the axis A relative to the plunger 103 (and relative to the firing pin 110, and accordingly, the projection 114). In addition, the rotary arm module 102 and the plunger 103 (along with the firing pin 110, and therefore, the projection 114) are movable (i.e., translatable) with respect to one another in the axial direction (e.g., parallel with the axis A), at least when the projection 114 is in the second portion 127 of the guideway 121.

In some embodiments, as shown, the guideway 121 can include a two-sided channel or groove, e.g., with walls spaced a distance apart to be dimensioned to receive the projection 114 therebetween.

However, it should be understood that this need not be the case. For example, in some embodiments, the guideway 121 can be fixedly coupled to the plunger 103 (e.g., via the firing pin 110, another suitable structure, or by being integrally formed therewith), and the projection 114 can be provided by (e.g., coupled to or integrally formed with) the rotary arm module 102 or another suitable structure. In such embodiments, the guideway 121 and the projection 114 would still be rotatable and translatable with respect to one another in order to move the plunger 103 from its first position to its second position to actuate dose release, e.g., to actuate the canister valve 54 in embodiments employing a pMDI canister, such as the embodiment shown in FIG. 1.

As shown in FIGS. 4-5, the rotary arm module 102 of the illustrated embodiment includes a shaft 120 having a shaft axis (e.g., a longitudinal axis) S configured to be oriented along or parallel to the axis A when the firing system 101 is assembled, and comprising a wall 122. The guideway 121 can be formed in the wall 122, and particularly, can be formed at least partially through the thickness of the wall 122, or can be formed all the way through the thickness of the wall 122 (i.e., as shown in FIGS. 4-5 and 8-9).

In some embodiments, more than one guideway 121 can be provided. For example, as shown, the shaft 120 of the rotary arm module 102 includes two guideways 121, and particularly, two diametrically opposed guideways 121. As few as one guideway 121 and as many as structurally possible and/or necessary for balanced, coordinated, and/or reliable operation of the firing system 101 can be employed. One guideway 121 will be described in greater detail for simplicity, but it should be understood that the description of the guideway 121 can be applied to as many guideways 121 as employed.

As shown in FIGS. 4-5 and 8-9, at least a portion of the guideway 121 can have a helical shape. That is, the guideway 121 can include a portion of a helix, but need not extend fully about 360 degrees of the shaft 120. For example, in some embodiments, the guideway 121 may only extend about the shaft 120 for less than 90 degrees; in some embodiments, less than 60 degrees; in some embodiments, less than 45 degrees; and in some embodiments, less than 40 degrees.

Particularly, as shown, the guideway 121 can have a first (e.g., upper) portion 125 having a first helix angle α (see FIG. 4) with respect to the axis A (or with respect to the shaft axis S) that is greater than zero. As a result, at least the first portion 125 is a helical portion of the guideway 121. Furthermore, the guideway 121 can have a second (e.g., lower) portion 127 having a second helix angle with respect to the shaft axis S (or the axis A when the firing system 101 is assembled) that is less than the first helix angle α. In the illustrated embodiment, the second helix angle is substantially zero and is therefore not indicated with a reference symbol or numeral. Because the second helix angle is substantially zero, the second portion 127 of the illustrated guideway 121 is substantially aligned with, or is oriented substantially parallel with respect to, the shaft axis S (and the axis A when the firing system 101 is assembled), and is not helical. As a result, in some embodiments, the guideway 121 can be described as including a first helical portion 125, and a second axial (or straight, or linear) portion 127.

Particularly, the second helix angle is less than the first helix angle α (i.e., the second portion 127 of the guideway 121 is oriented at a smaller angle with respect to the axis A than the first portion 125), such that the second portion 127 of the guideway 121 is steeper than the first portion 125 of the guideway 121. Said another way, the second portion 127 of the guideway 121 can be described as being more aligned with, or more parallel to, the axis A, or oriented more axially with respect to the axis A, than the first portion 125 of the guideway 121.

By employing a unique two-portion guideway 121 where the first portion 125 has a greater helix angle than the second portion 127, the guideway 121 can assist the latch 106 in holding back the relatively large firing force of the stored energy device 109 (e.g., the load of a spring), which can allow the use of a sensitive latch 106 where the entire force of the stored energy is not all placed directly on the latch 106 but still provides sufficient axial firing force (e.g., after the projection 114 has transitioned from the first portion 125 to the second portion 127 of the guideway 121). The guideway 121 can particularly be configured to allow rotary motion about the axis A to be transferred or converted to more axial (e.g., linear) motion (i.e., in a direction oriented along or parallel to the axis A, or at least more along or more parallel to the axis A).

In some embodiments, the first helix angle α can be at least 45 degrees, in some embodiments, at least 50 degrees, in some embodiments, at least 60 degrees, and in some embodiments, at least 65 degrees. In some embodiments, the first helix angle α can be less than 90 degrees, in some embodiments, less than 80 degrees, in some embodiments, less than 60 degrees, in some embodiments, less than 50 degrees, and in some embodiments, less than 45 degrees.

In some embodiments, the second helix angle can be less than 45 degrees, in some embodiments, less than 30 degrees, in some embodiments, less than 25 degrees, in some embodiments, less than 20 degrees, in some embodiments, less than 15 degrees, in some embodiments, less than 10 degrees, in some embodiments, less than 5 degrees, and in some embodiments, is about 0 degrees (i.e., such that the second portion is substantially axial and oriented substantially along or parallel to the axis).

In some embodiments, as shown, at least a portion of the guideway 121 (e.g., the first portion 125) can be curved. As a result, the first portion 125 of the guideway 121 may not have a constant first helix angle, but in such embodiments, any helix angle along the first portion 125 (as measured relative to the vertical, i.e., as measured relative to the axis A or the shaft axis S) is greater than the second helix angle. Alternatively, in such curved embodiments, the "first helix angle" can refer to an average helix angle over the curved first portion 125 of the guideway 121.

The shaft 120 can further include a flanged (upper) end 118, which can be in the form of an annular cylindrical flange and can include or define an orifice 119. In some embodiments, the shaft 120 can be hollow and can define a tubular channel 123 that extends along the shaft axis S. As such, the shaft 120, and particularly, the tubular channel 123 can be dimensioned to receive the firing pin 110. In such embodiments, the orifice 119 can be generally aligned with, and connected to, the tubular channel 123 of the shaft. The flanged end 118 of the shaft 120, and particularly the bottom surface thereof, can be configured to provide a surface against which the stored energy device 109 can press, e.g., when the stored energy device 109 is in the form of a biasing element. In such embodiments, the second recess 124 of the plunger 103 (e.g., a base of the second recess 124) can provide the opposing surface against which the stored energy device 109 can press. The shaft 120 can be dimensioned to be received in the second recess 124 of the plunger 103, along with the stored energy device 109 and the firing pin 110, and the shaft 120 can be rotatable about the shaft axis S (and about the axis A of the firing system 101 when assembled). As such, the shaft 120 can be rotatable relative to the plunger 103.

As shown in FIGS. 4-5 and 8-9, the rotary arm module 102 can further include an arm (e.g., a chamfered arm) 117 extending radially outwardly from the flanged end 118 of the shaft 120 (i.e., radially outwardly, relative to the shaft axis S). As such, the arm 117 also resides outside (e.g., above) the second recess 124 of the plunger 103. The arm 117 can be integrally formed with the shaft 120, as shown, or can be coupled thereto, to provide a moment arm for rotation of the shaft 120 about the shaft axis S and the axis A. The arm 117 and the latch 106 can be configured to inter-engage, such that the latch 106 can maintain the firing system 101 in its primed state and can be released to allow the stored energy of the stored energy device 109 to be released to cause the firing system 101 to fire, i.e., to change to its fired state.

As shown in FIGS. 3 and 6-9, the firing pin 110 can include a shaft (or cylindrical or tubular body) 113 having a shaft axis (e.g., a longitudinal axis) F (see FIGS. 6 and 7) configured to be oriented substantially in the axial direction (e.g., along the axis A) of the firing system 101 when the firing system 101 is assembled. The shaft 113 can be dimensioned to be received in the tubular channel 123 of the shaft 120 of the rotary arm module 102. In addition, in some embodiments, the firing pin 110 (and hence the projection 114) and the plunger 103 can be configured to be fixedly coupled to one another, and particularly, to inhibit relative rotation between the firing pin 110 (and hence the projection 114) and the plunger 103. In some embodiments, the firing pin 110 and the plunger 103 can include one or more inter-engaging features 116 to accomplish this.

As shown, in some embodiments, the inter-engaging features 116 can include one or more (two are shown by way of example) axial projections 126 on the firing pin 110 dimensioned to be received in a corresponding number of correspondingly shaped recesses 128 formed in the plunger 103 (see FIG. 3), and particularly, formed in a base of the second recess 124, to fixedly couple (e.g., rotationally fix) the firing pin 110 and the plunger 103. Such inter-engaging features 116 are shown by way of example only, however, it should be understood that other inter-engaging features can be used, such as one or more of a bolt, a rivet, an interference fit, a snap-fit, thermal and/or ultrasonic welding, an adhesive, a cohesive, a magnet, other suitable coupling means, or a combination thereof.

As described above, the projection 114 can be provided by the firing pin 110. In some embodiments, more than one projection 114 can be provided. For example, as shown, the firing pin 110 includes two projections 114, and particularly, two diametrically opposed projections 114, each dimensioned to be received in and movable along a guideway 121. As few as one projection 114 and as many as structurally possible and/or necessary for balanced, coordinated, and/or reliable operation of the firing system 101 can be employed. One projection 114 will be described in greater detail for simplicity, but it should be understood that the description of the projection 114 can be applied to as many projections 114 as employed.

As shown in FIGS. 6 and 7, the projection 114 can extend radially outwardly from the shaft 113 of the firing pin 110. In some embodiments, as further shown in FIGS. 6 and 7, the projection 114 can project or protrude from (and reside in) a flat, recessed area or region 115 formed in an outer surface of the shaft 113 of the firing pin 110. Furthermore, in some embodiments, the projection 114 can be chamfered on one or more of its edges, e.g., to facilitate relative movement with respect to the guideway 121. In addition, as shown in FIGS. 6 and 7, in some embodiments, the projection 114 can have a parallelogrammatic cross-sectional shape (e.g., taken along a direction oriented substantially perpendicularly with respect to the shaft axis F, or the axis A when the firing system 101 is assembled).

As further shown in FIGS. 7-9, in some embodiments, the projection 114 can be angled or tilted, such that the projection 114 is oriented at a non-zero and non-right angle with respect to the shaft axis F (and with respect to the axis A of the firing system 101 when assembled). When more than one projection 114 is employed, and particularly, when two opposing projections 114 are employed, the projections 114 can be inverted mirror images of one another (see FIG. 6), such that the firing pin 110 does not have mirror symmetry about a central longitudinal axis, but does have rotational symmetry (e.g., if rotated 180 degrees about its central longitudinal axis). As shown in FIGS. 8-9, the projection 114 can be configured to correspond with and to cam along the guideway 121.

The projection 114 can be dimensioned to be received in the guideway 121 in such a way that the projection 114 is movable in the guideway 121, and such that the projection 114 and the guideway 121 are movable with respect to one another between a first (e.g., primed) position (see FIG. 8) that corresponds to the first position of the plunger 103 and a second (e.g., fired) position (see FIG. 9) that corresponds to the second position of the plunger 103. As a result, the projection 114 is configured to cam along the guideway 121 when driven by, and in response to, the stored energy being released from the stored energy device 109 to cause the plunger 103 to move (i.e., to translate axially) between its first position and its second position (i.e., as the projection 114 travels in the guideway 121, and particularly, as the projection 114 travels in the second portion 127 of the guideway 121).

In some embodiments, the rotary arm module 102, the firing pin 110, the convex circular spacer 105, and latch 106 can be formed of steel. In some embodiments, the preferred method of manufacturing such steel parts is by metal injection molding. In some embodiments, the plunger 103 can be formed of a suitable plastic material. However, it will be obvious to one skilled in the art that other suitable materials and methods of manufacturing can be used.

As shown by a combination of FIGS. 3, 8-10 and 13, when the firing system 101 is assembled, the base 49 of the canister 51 is received in the first recess 111 of the plunger 103; the firing pin 110 is located within the tubular channel 123 of the shaft 120 of the rotary arm module 102; the projection 114 is positioned in the guideway 121; the shaft 120 of the rotary arm module 102, the firing pin 110, and the stored energy device 109 are received in the second recess 124 of the plunger 103 (particularly, the stored energy device 109 of the illustrated embodiment is located between an outer surface of the shaft 120 of the rotary arm module 102 and an inner surface of the second recess 124 of the plunger 103); the convex circular spacer 105 is positioned in the orifice 119 of the rotary arm module 102; and the inter-engaging features 116 of the firing pin 110 and the plunger 103 are inter-engaged to fixedly couple, i.e., secure, the firing pin 110 (and the projection 114) to the plunger 103.

The firing system 101 exists in three states: primed ('cocked'), fired and returned. FIG. 10 illustrates the firing system 101 in its primed state in contact with the canister 51, with the stem portion 58 of the pMDI canister valve 54 seated in the stem socket 59, comprising the spray orifice 60, of the inhaler housing 55. In the primed state, the stored energy device 109, and particularly in embodiments in which the stored energy device 109 includes a biasing element, can be compressed between the rotary arm module 102 (e.g., the flanged end 118 thereof) and the plunger 103 (e.g., the base of the second recess 124 thereof). Extending internally from the top of the inhaler housing 55 is a column 43 that has a convex end (e.g., formed by a rounded surface, one or more angled surfaces, or a combination thereof) that is in contact over a small area with the convex circular spacer 105. The column 43 can provide a reaction surface for the stored energy device 109. That is, the force of the stored energy device 109, e.g., when including a biasing element, is resisted by the column 43, which presses against the convex circular spacer 105. The contact between the two convex surfaces is arranged to provide low friction, and hence minimal loss of energy due to friction, when the rotary arm module 102 rotates during actuation.

In the primed state, the firing pin 110 is generally enveloped by the rotary arm module 102. FIGS. 8 and 11 illustrate the relative positions between the guideway 121 and the projection 114 in the primed state. By way of example only, FIG. 12 shows that the rotary arm module 102 is in a 9 o'clock position in the primed state, locked in place by the latch 106. As shown in FIGS. 1-3, 12 and 15, the firing system 101 can further include a return biasing element 129 located underneath the latch 106, which can be used to return the latch 106 to its first position, i.e., from its second position, as described in greater detail below. In some embodiments, the return biasing element 129 can include a spring, and particularly, a compression spring (e.g. with a compressed force of 2 N). The biasing element 129 can also ensure that the latch 106 remains engaged until it is desired to move the latch 106 from its first position to its second position (e.g., even if the firing system 101, or the inhaler 100, is shaken).

As mentioned earlier, the latch 106 can be movable between (i) a first (i.e., latched) position (see FIGS. 10 and 12) in which the latch 106 is coupled to at least one of the guideway 121 and the projection 114 (e.g., in the illustrated embodiment, the latch 106 is indirectly coupled to the guideway 121 via the arm 117 of the rotary arm module 102) to inhibit the guideway 121 and the projection 114 from moving relative to one another, the stored energy in the stored energy device 109 is held from being released, and the firing system 101 is in the primed state, and (ii) a second (i.e., unlatched) position (see FIGS. 13 and 15) in which the latch 106 is decoupled (i.e., released) from the guideway 121 and the projection 114 (e.g., in the illustrated embodiment, the latch 106 is released from the arm 117 of the rotary arm module 102), such that the guideway 121 and the projection 114 are free to move relative to one another, the stored energy of the stored energy device 109 is released, and the firing system 101 is free to change to the fired state. The stored energy device 109 can be configured and positioned, such that the stored energy is released in response to the latch 106 being moved from its first position to its second position.

That is, the latch 106 can be configured to: (i) maintain the firing system 101 in the primed state, wherein the guideway 121 and the projection 114 are stationary with respect to one another and the stored energy of the stored energy device 109 is not released, and (ii) release the firing system 101 from the primed state to allow the guideway 121 and the projection 114 to move relative to one another and to allow the stored energy of the stored energy device 109 to be released to drive the firing system 101 toward the fired state.

By way of example only, as shown in the illustrated embodiment, the latch 106 can be configured to be pivotally movable about a latch axis L (see FIG. 2) between the first position and the second position. In some embodiments, the latch axis L can be oriented substantially perpendicularly with respect to the axis A of the firing system 101. The trigger 130 can be configured such that when the trigger 130 is actuated, as described in greater detail below, the trigger 130 can cause the latch 106 to move from its first position to its second position. For example, as shown in the illustrated embodiment, the trigger 130 can be actuated to cause the latch 106 to pivot on the pin 107 (e.g., about the latch axis L), thereby causing compression of the return biasing element 129.

In its second position, the latch 106 is no longer in contact with the rotary arm module 102, thus freeing the rotary arm module 102 to move, and also releasing the energy from the stored energy device 109. Particularly, in the illustrated embodiment, the stored energy device 109 is freed by release of the arm 117 of the rotary arm module 102. The release of the stored energy can thus begin to exert force on the rotary arm module 102. Release of the stored energy from the stored energy device 109 further drives the guideway 121 and the projection 114 to move relative to one another. As shown in FIG. 15, this is enabled by anti-clockwise rotation of the rotary arm module 102 through approximately 45° (as evident by comparing the position of the arm 117 in FIGS. 12 and 15).

Particularly, as shown in FIGS. 8 and 11, due to the configuration of the guideway 121 and the interaction between the guideway 121 and the projection 114, the guideway 121 and the projection 114 (e.g., when the projection 114 is received in the first portion 125 of the guideway 121), begin to rotate relative to one another. In embodiments in which the stored energy device 109 includes a spring, this allows the spring to uncompress. As shown in FIGS. 9 and 14, as the projection 114 and the guideway 121 continue to move relative to one another (i.e., from a primed position to a fired position), driven by the stored energy device 109, the projection 114 moves into the second portion 127 of the guideway 121, where the second helix angle is less than that of the first portion 125, such that the guideway 121 and the projection 114 can additionally or alternatively further translate relative to one another (e.g., in a direction oriented more axially with respect to the axis A).

The relative movement of the projection 114 and the guideway 121, shown by comparing FIGS. 8 and 11 with FIGS. 9 and 14, causes the plunger 103 to move (e.g., axially) from its first position to its second position, correlating with a dose release firing. In embodiments in which the inhaler 100 is a pMDI (as shown in FIG. 1), the plunger 103 moves from its first position to its second position to cause the canister 51 to move, thus reaching its fired state, as shown in FIG. 13, where the metering valve 54 releases a dose. This is allowed as each projection 114 progresses in a guideway 121 from its first position (see FIG. 11) to its second position (see FIG. 14) with respect to the guideway 121.

As described above, rotation of the plunger 103 can be inhibited during firing due to the inter-engaging features between the plunger 103 and the housing 55 of the inhaler 100 (e.g., due to the ribs 136 of the plunger 103 being seated in the recesses 47 of the housing 55), forcing the plunger 103 to translate in the housing 55, i.e., to travel axially with respect to the axis A of the firing system 101.

Return of the firing system 101 to its primed state can be achieved by a reset (or "priming" or "cocking") mechanism 160 that can be coupled to the inhaler 100 and/or the firing system 101, as shown in FIGS. 10 and 13. Referring to FIG. 10, in some embodiments, reset can be achieved via one or more cams 162 (e.g., 'egg' shaped cams or eccentric cams) and a handle (or "lever," or "cocking lever") 164. As shown in FIG. 13, when the firing system 101 is in its fired state, the plunger 103 is coupled to (e.g., in contact with) the cam(s) 162. Application of a pulling force (e.g., an upward pulling force) on the handle 164 results in rotation of the cam(s) 162. The rotation of the cam(s) 162 therefore drives the plunger 103 upwards from its second position to its first position. In the illustrated embodiment, this motion applies a force in a direction opposite to the spring force of the stored energy device 109, developing a load, or stored energy, in the stored energy device 109.

Movement of the plunger 103 from its second position to its first position further causes each projection 114 to travel back up the corresponding guideway 121 (e.g., compressing the spring of the stored energy device 109, when employed), and further causes the rotary arm module 102 to return to its 9-o'clock position shown in FIG. 12. When the triggering force (e.g., by the trigger 130) is no longer being applied to the latch 106, the return biasing element 129 applies a small force to the latch 106, causing the latch 106 to move from its second position to its first position, thus ensuring that it returns to full latching engagement with the rotary arm module 102 (e.g., with the arm 117 thereof). The user can then return the handle 164 to its starting position, which rotates the cam(s) 162 in the opposite direction, causing the cam(s) 162 to become decoupled from the plunger 103. The reset mechanism 160 is shown by way of example as including two cams 162, and particularly, two diametrically opposed cams 162, but this need not be the case. As few as one cam 162 and as many as structurally necessary can be employed to reset the firing system 101.

The above described reset mechanism 160 is shown and illustrated in FIGS. 10 and 13 by way of example only. However, it should be understood that other reset mechanisms can be employed to return all of the elements of the firing system 101 to their respective first positions and to return the firing system 101 to a starting or primed state. For example, in some embodiments, arrangements other than the handle 164 (e.g., a pivoting mouthpiece cover) can be used to re-prime the firing system 101.

The configuration of the firing pin 110 and rotary arm module 102 providing the projection 114 and the guideway 121, respectively, can offer benefits of compactness and manufacturing ease. However, it will be obvious to one skilled in the art that other arrangements are possible. For example, as mentioned above, in some embodiments, the guideway 121 may not be formed through the thickness of the wall 122 of the shaft 120. In some embodiments, the wall thickness of the shaft 120 can be greater, thereby allowing the one or more guideways 121 to be formed entirely within the thickness of the wall 122 of the shaft 120, creating an unbroken outer surface to the shaft 120. Such an embodiment can confer additional strength to the rotary arm module 102, but generally requires a more sophisticated manufacturing method (e.g., injection moulding using collapsing cores, additive manufacturing technology, other suitable methods, or a combination thereof).

In some embodiments, the one or more guideways 121 can include a larger helical portion, where one or more guideways 121 include at least one 360 degree portion about the circumference of the shaft 120. In such embodiments, a rotating molding tool core can be used to injection mold such a part.

In some embodiments, one or more projections 114 can be located on the rotary arm module 102 (e.g., extending outwardly from an outer surface of the shaft 120 thereof), which can be located within a hollow firing pin 110 (i.e., the reverse of the illustrated embodiment). Such projection(s) 114 could extend through a wall thickness of the firing pin shaft 113, or they could be shorter and engage in a guideway 121 formed within the inner part of the firing pin 110 (e.g., within the inner portion of a thick hollow firing pin shaft wall), allowing the outside of the firing pin shaft wall to be unbroken and continuous, e.g., for reasons of strength.

The number, configuration, and sizes of the projections 114 and guideways 121 of the firing systems 101 of the present disclosure may be chosen to suit a particular application, these details being capable of determination by one skilled in the art. Furthermore, in some embodiments, the angle of the projection(s) 114 (e.g., with respect to the axis A) and shape/angles of the guideway(s) 121 may be chosen to customize a firing system for a particular application, e.g., for pMDI canister valves with differing properties, if required.

As described earlier, the trigger 130 can be used to apply a triggering force to the latch 106 to move the latch 106 from its first position to its second position to allow release of the firing system 101 from its primed state. That is, the trigger 130 can be operatively coupled to the latch 106 and configured to change between a first state and a second state to move the latch between the first position and the second position, respectively (i.e., to allow the firing mechanism 101 to be fired). In some embodiments, the trigger 130 can be breath-actuated. In some embodiments, the trigger 130 can be configured to change between its first state and its second state in response to non-mechanical energy (e.g., an electrical signal); and in some embodiments, the trigger 130 can be configured to change between its first state and its second state in response to mechanical energy.

Various embodiments of triggers of the present disclosure will now be described in greater detail with respect to FIGS. 1 and 16-20. For simplicity, the remainder of the firing system components of exemplary FIGS. 16-20 are the same as those of the firing system 101 described above.

As shown in FIG. 1, the inhaler 100 includes a trigger 130 according to one embodiment of the present disclosure. By way of example only, the trigger 130 includes a shape memory material, e.g., a shape memory alloy (SMA) wire 131, coupled to the latch 106 and positioned to provide force to the latch 106 to move the latch 106 from its first position to its second position. Particularly, a first portion of the SMA wire 131 can be coupled to (e.g., looped over and/or tied to) an end of the latch 106 that is on the opposite side of the pin 107 from an end of the latch 106 that is configured to retain the rotary arm module 102 (e.g., the arm 117 thereof), and a second portion of the SMA wire 131 can be secured in a fixed location in the housing 55, e.g., by one or more crimps 133. The crimps 133 can be coupled to, or in communication with, the controller 151. The SMA wire 127 can be powered using an appropriate power source (not shown), such as a cell or a battery of cells.

Actuation, or firing, of the firing system 101 can occur when the appropriate signal is received by the controller 151, which can be in the form of an electrical signal from a user-operated switch (not shown) on the inhaler housing 55, e.g., in a form of a "press and breath" arrangement, or in the form of one or more signals from one or more sensing elements present in the inhaler 100, such as those of the inspiratory air flow detection system 150, i.e., in a breath-actuated arrangement.

Upon receiving the appropriate signal(s), the controller 151 sends an electrical current, or other form of non-mechanical energy, to the SMA wire 131 (e.g., for approximately 0.2 s), causing the SMA wire 131 to heat up due to its resistance and therefore causing it to contract as a result of the solid state microstructural transformation that such materials exhibit when appropriately heated. In some embodiments, the transformation temperature of the SMA wire 131 can be about 90° C., and the controller 151 can be configured to create an electrical current to heat the SMA wire 131 to a temperature of around 90° C. Contraction of the SMA wire 131 results in a pulling force being applied to the latch 106 to move the latch 106 from its first position to its second position, and particularly, causing it to pivot on its pin 107 to release the rotary arm module 102 (e.g., the arm 117 thereof), allowing the stored energy device 109 to be released to drive the plunger 103 to move from its first position to its second position to cause valve actuation (i.e., actuation of the valve 54 to dispense a dose of medicament from the spray orifice 60).

Upon cessation of the heating current from the controller 151, loss of heat from the SMA wire 131 allows it to return to its original state, the SMA wire 131 thereby lengthening again (e.g., under the action of the return biasing element 129). In some embodiments, cooling of the SMA wire 131 can take about 1 s to reach room temperature (e.g., 20-25° C.). After firing, the firing system 101 can be re-primed as described previously.

In some embodiments, the SMA wire 131 can be a nickel-titanium alloy comprising 50% nickel and 50% titanium, the diameter of the SMA wire 131 can be about 75 μm and it can have a length of about 60 mm. Using an SMA wire 131 with the described properties and a 1.5 V lithium ion cell, the contraction of the SMA wire 131 can take about 0.2 s, and the SMA wire 131 can transition to its second, contracted, state between 70-90° C. After approximately 0.2 s the controller 151 can be programmed to stop the electrical current, allowing the SMA wire 131 to return to its first state. In some embodiments, multiple loops or lengths of the SMA wire 131 can be employed. In some embodiments, an SMA comprising a different compositional makeup (e.g., different percentages of nickel and titanium, and/or comprising an alloy of different metals) can be employed. In addition, in some embodiments, different means for coupling the SMA wire 131 to the controller 151 can be employed, and the one or more crimps 133 are shown by way of example only.

Additional exemplary embodiments of triggers of the present disclosure will now be described with respect to FIGS. 16-20, wherein like numerals reference like elements. Reference is made to the description above accompanying FIG. 1 for a more complete description of the features and elements (and alternatives to such features and elements) of the inhaler 100 and the firing system 101. The dedicated air flow path 146, the flow governor 140, and the inspiratory air flow detection system 150 have been removed from FIGS. 16-20 for simplicity and clarity. However, it should be understood that any of the features described above with respect to FIGS. 1-15 can be applied to the embodiments of FIGS. 16-20, and vice versa. Alternatively, an air inlet for the inhaler can be formed in or provided by another region of the inhaler of FIGS. 16-20.

Figure 16:
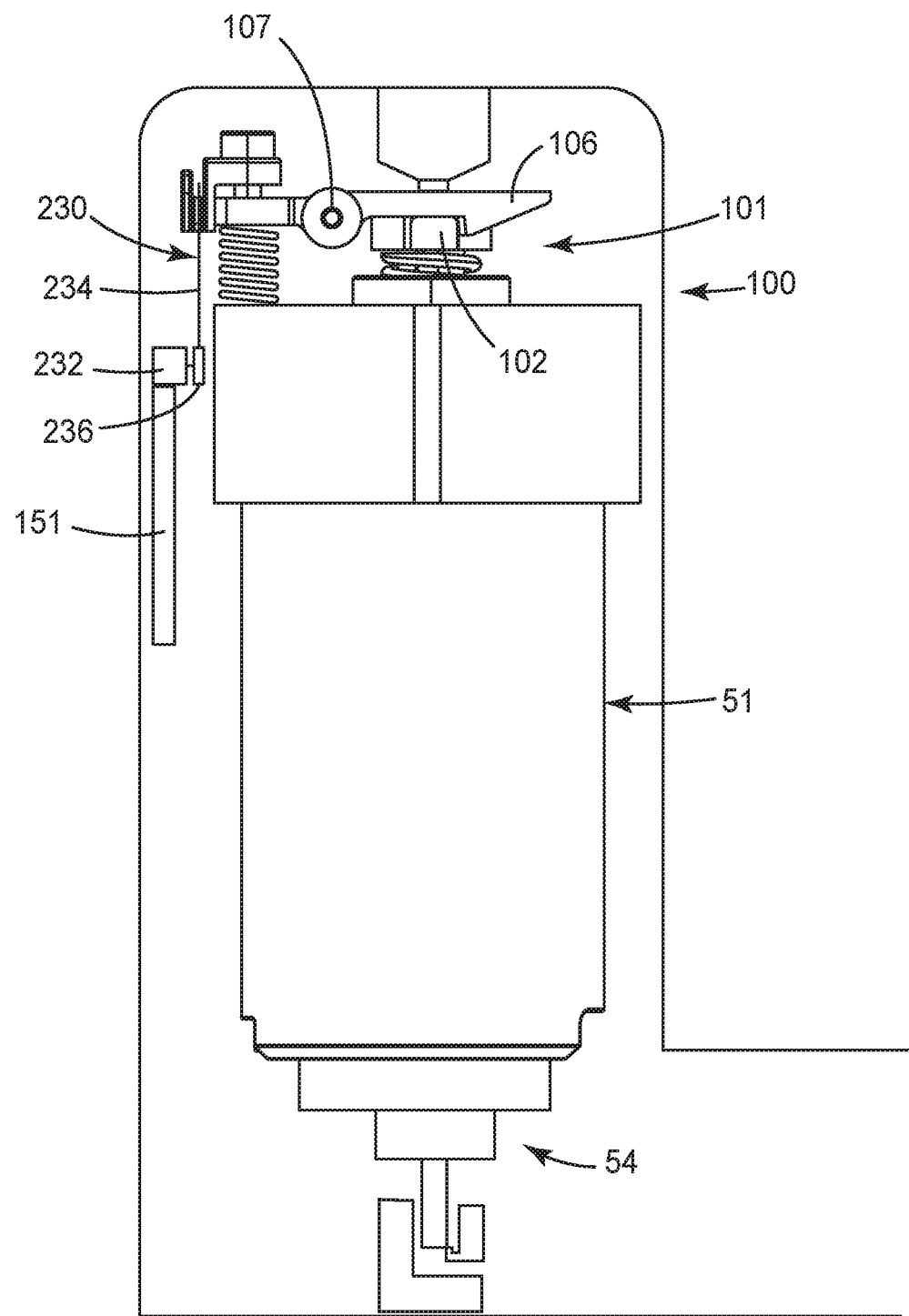
FIG. 16 is a cutaway side elevational view of the medicinal inhaler of FIG. 1, with portions removed for clarity, comprising a trigger according to another embodiment of the present disclosure that includes a digital motor.

FIG. 16 illustrates a trigger 230 according to another embodiment of the present disclosure, the trigger 230 being shown in combination with the firing system 101 and other elements of the inhaler 100 of FIGS. 1-15. The trigger 230 includes a digital motor 232 to provide force to the latch 106 to move the latch 106 from its first position to its second position. The trigger 230 of FIG. 16 further includes a length of filament 234 (e.g., nylon or other suitable thread-like material) positioned to couple the latch 106 to a spool 236 attached to the digital motor 232 in communication with the controller 151. The digital motor and the controller 151 can be powered using an appropriate power source (not shown), such as a battery.

Actuation of the firing system occurs when the appropriate signal(s) is/are received by the controller 151, as described previously. Upon receiving the appropriate signal(s), the controller 151 sends an electrical current to the digital motor 232 causing the filament 234 to be taken up by the spool 236 (i.e., wound around the spool 236). This results in shortening of the extended length of the filament 234, which causes the end of the latch 106 opposite the end retaining the rotary arm module 102 to pivot on its pin 107 and release the rotary arm module 102, thereby releasing the firing system 101 to fire, allowing actuation of the metering dose valve 54 of the pMDI canister 51. As will be appreciated by a person of ordinary skill in the art, the controller 151 can cause the current to be switched off (i.e., after firing), disabling the trigger and allowing the system 101 to be re-primed. The firing system 101 can be re-primed as described above.

Figure 17:
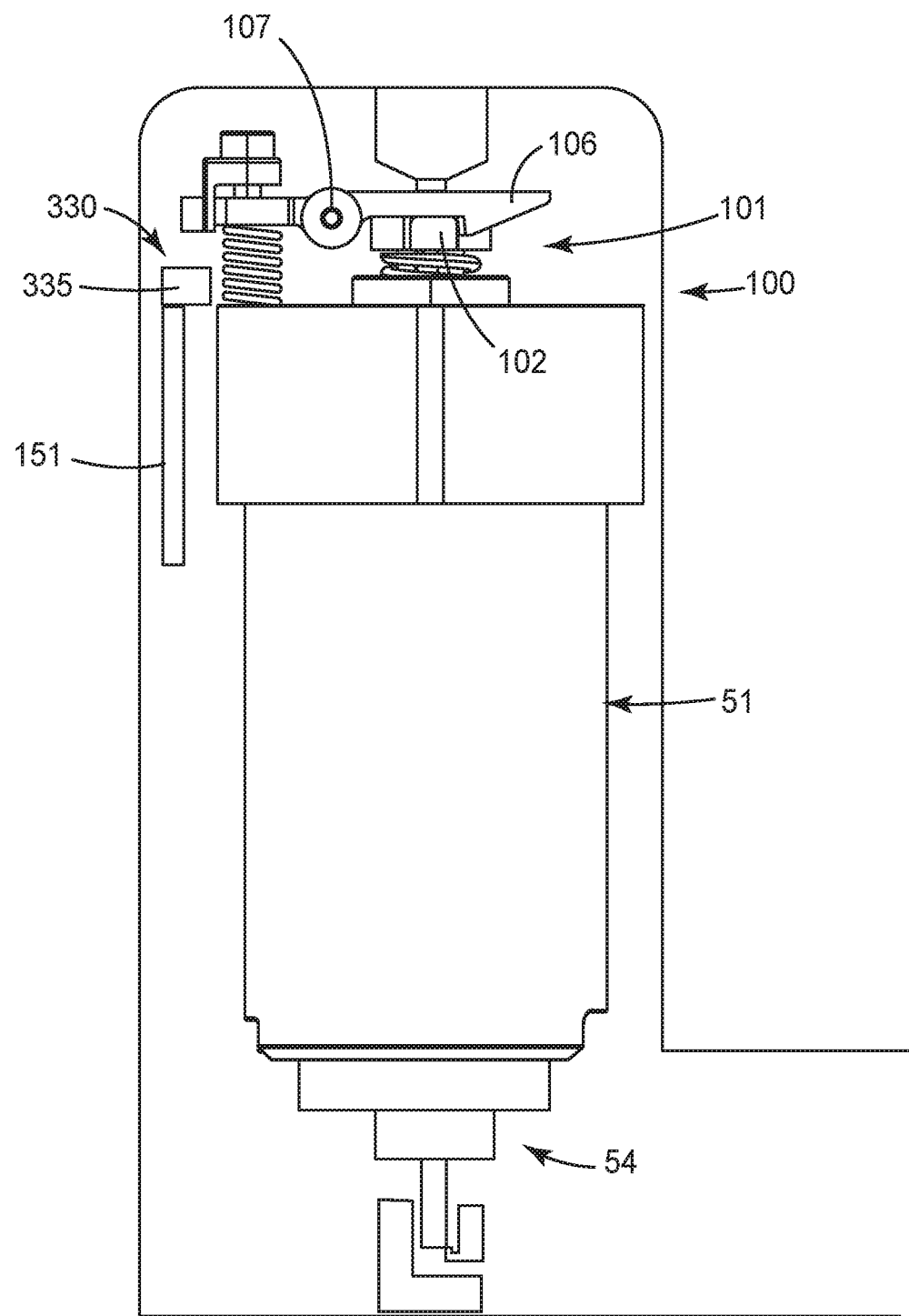
FIG. 17 is a cutaway side elevational view of the medicinal inhaler of FIG. 1, with portions removed for clarity, comprising a trigger according to another embodiment of the present disclosure that includes an electromagnet.

FIG. 17 illustrates a trigger 330 according to another embodiment of the present disclosure, the trigger 330 being shown in combination with the firing system 101 and other elements of the inhaler 100 of FIGS. 1-15. The trigger 330 includes an electromagnet 335 to provide force to the latch 106 to move the latch 106 from its first position to its second position. The electromagnet 335 is in communication with (i.e., is electrically connected to) the controller 151. The electromagnet 335 and the controller 151 can be powered using an appropriate power source (not shown), such as a battery.

Actuation of the firing system occurs when the appropriate signal(s) is/are received by the controller 151, as described previously. Upon receiving the appropriate signal(s), the controller 151 sends an electrical current to the electromagnet 335. The resultant magnetic force can be configured to attract the end of the latch 106 opposite the end retaining the rotary arm module 102 to cause the latch 106 to pivot on its pin 107 and release the rotary arm module 102, thereby releasing the firing system 101 to fire, allowing actuation of the metering dose valve of the pMDI canister 51. The firing system 101 can be re-primed as described above.

Figure 18:
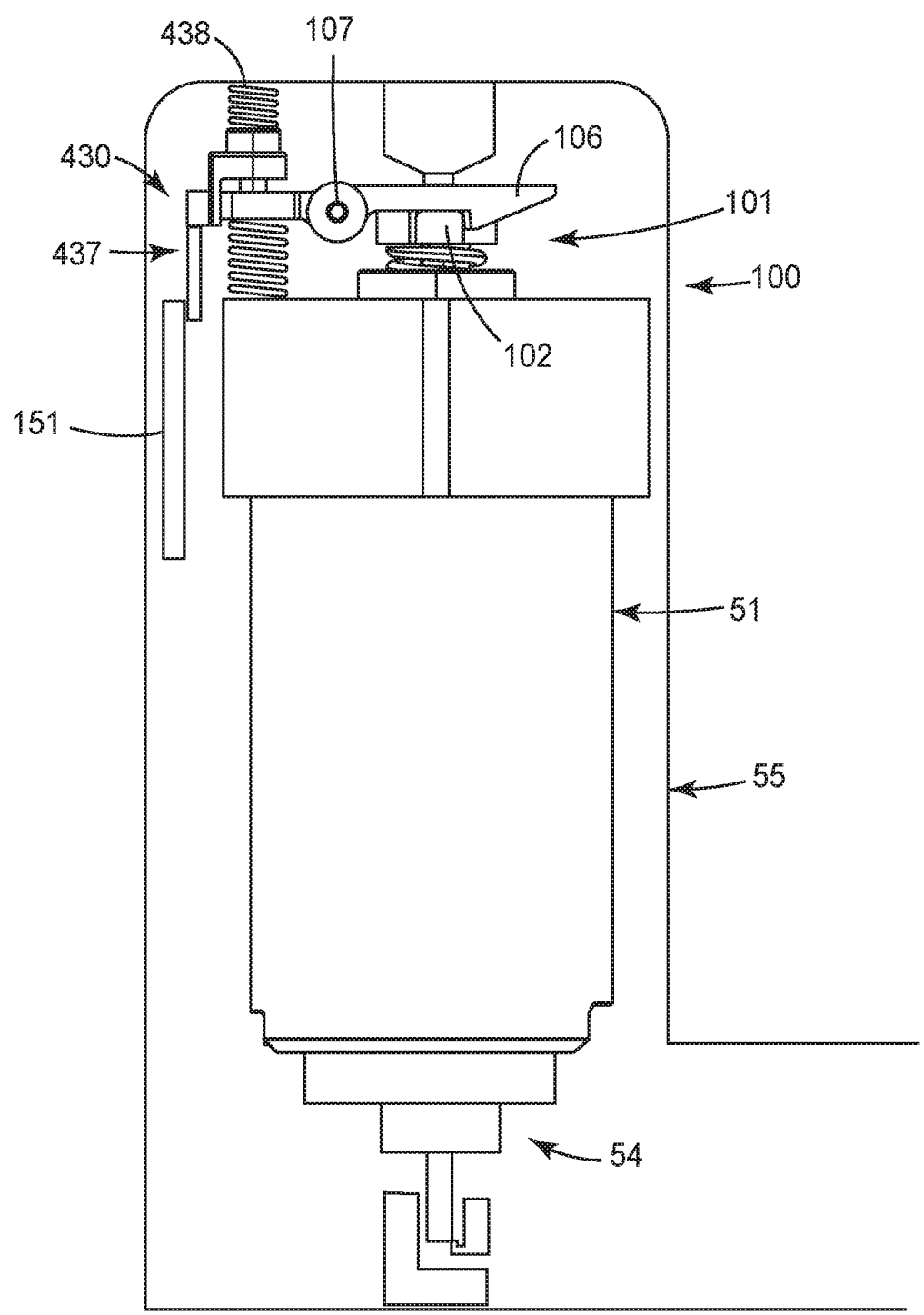
FIG. 18 is a cutaway side elevational view of the medicinal inhaler of FIG. 1, with portions removed for clarity, comprising a trigger according to another embodiment of the present disclosure that includes a solenoid.

FIG. 18 illustrates a trigger 430 according to another embodiment of the present disclosure, the trigger 430 being shown in combination with the firing system 101 and other elements of the inhaler 100 of FIGS. 1-15. The trigger 430 includes a solenoid 437 to provide force to the latch 106 to move the latch 106 from its first position to its second position. The solenoid 437 is in communication with (i.e., is electrically connected to) the controller 151. The solenoid 437 and/or the controller 151 can be powered using an appropriate power source (not shown), such as a battery. The trigger 430 can further include a biasing element 438 (e.g., a spring), under compression, located, for example, between the latch 106 and a portion of the housing 55. The biasing element 438 can provide an opposing biasing force to the solenoid 437. That is, the solenoid 437 and the biasing element 438 can oppose one another, such that the solenoid 437 opposes the forces exerted by the biasing element 438.

Actuation of the firing system occurs when the appropriate signal(s) is/are received by the controller 151, as described previously. Upon receiving the appropriate signal(s), the controller 151 sends an electrical current to the solenoid 437, causing it to actuate. This allows the biasing element 438 to exert its force on the end of the latch 106 opposite the end retaining the rotary arm module 102 to cause the latch 106 to pivot on its pin 107 and release the rotary arm module 102, thereby releasing the firing system 101 to fire, allowing actuation of the metering dose valve of the pMDI canister 51. The firing system 101 can be re-primed as described above.

A further advantage with using an electronic mechanism to release the latch 106 of the firing system 101 is that the controller 151 can be designed to communicate with a memory device incorporated into the inhaler 100. The electronic circuitry involved can be configured to allow each firing system triggering event to be counted and recorded, and can be used to also provide a dose count, e.g., for display to the patient on the inhaler 100 of the theoretical number of doses thus still remaining.

In embodiments in which one or more pressure sensors (see, e.g., the pressure sensors 152a and 152b of FIG. 1) are used to detect and measure the patient's inspiratory efforts, not only can the calculated air flow rate data be used to trigger dose release firing via a firing system of the present disclosure (e.g., the firing system 101), but incorporation of an appropriate electronic memory device can also allow the capture, storage and/or retrieval of the patient's inhalation profile (flow rates, pressure drops, etc.) corresponding to each time the inhaler was used. This information can be displayed for the user to see or a means to transmit these data, via a cable or using wireless technology, to a secondary device (e.g., to a computer or a 'smart' phone), can be included for future data retrieval to allow analysis and interpretation of the frequency and times of doses. These data could be made available to the patient's physician or others, in order to allow them to monitor the patient's ability to use the inhaler successfully and to allow appropriate and timely health care advice to be provided based on analysis and interpretation of the retrieved information.

Figure 19:
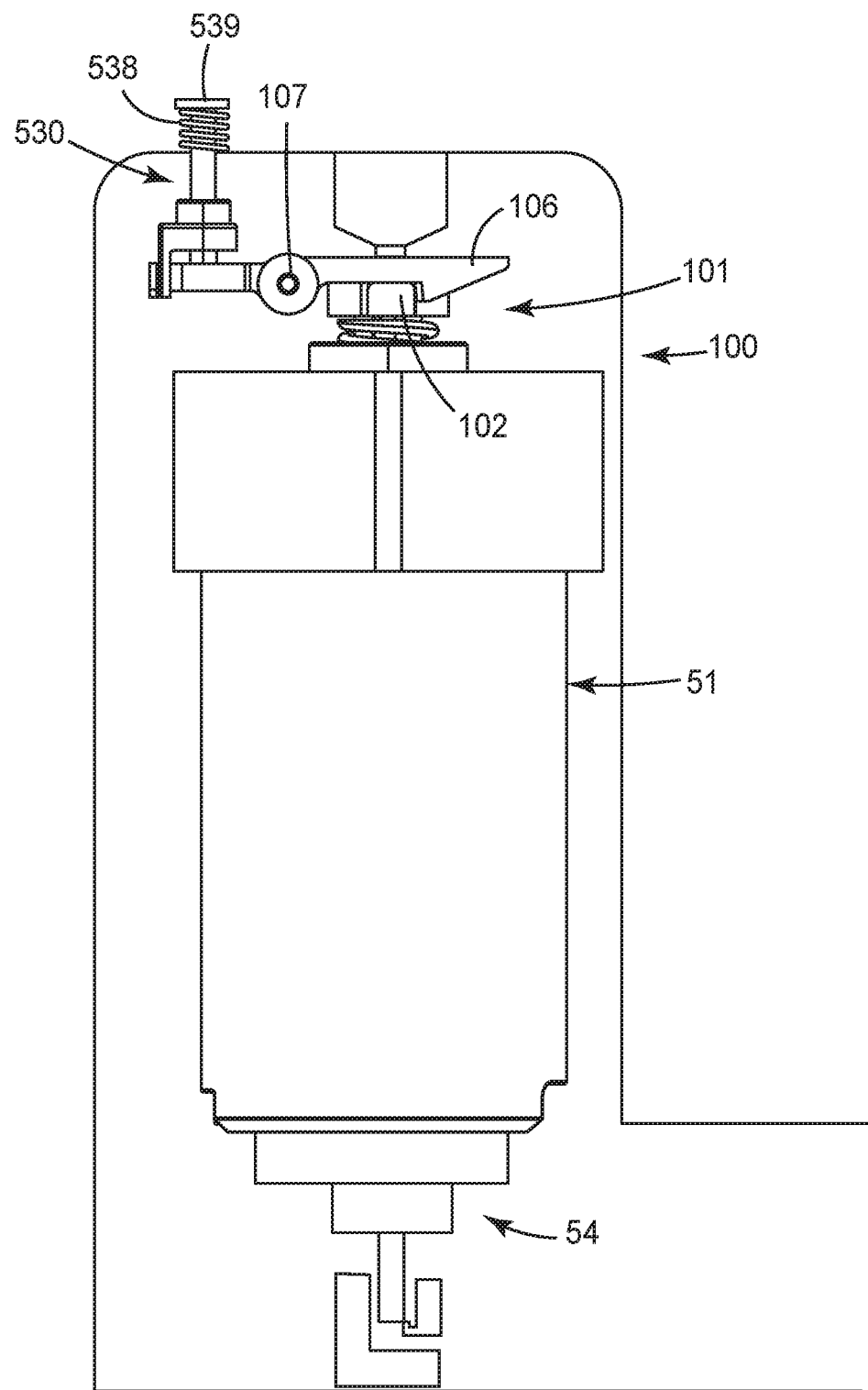
FIG. 19 is a cutaway side elevational view of the medicinal inhaler of FIG. 1, with portions removed for clarity, comprising a trigger according to another embodiment of the present disclosure that includes a mechanical actuator.
Figure 20:
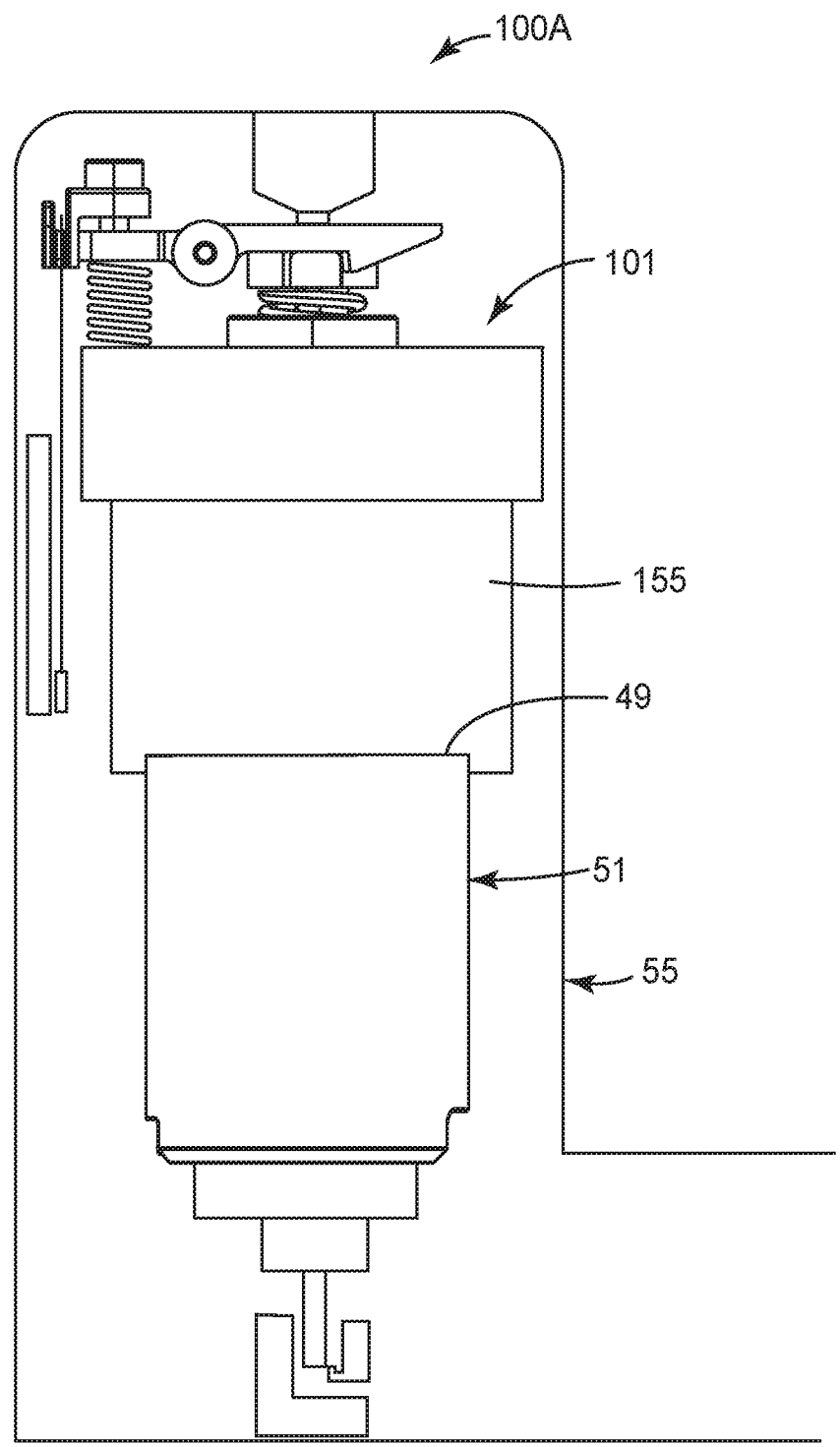
FIG. 20 is a cutaway side elevational view of a medicinal inhaler according to another embodiment of the present disclosure, the inhaler comprising the firing system of FIGS. 1-3, 10, 12-13 and 15 and an adapter located between the firing system and the medicament canister.

FIG. 19 illustrates a trigger 530 according to another embodiment of the present disclosure, the trigger 530 being shown in combination with the firing system 101 and other elements of the inhaler 100 of FIGS. 1-15. The trigger 530 includes a mechanical actuator 539 configured to cooperate with the latch 106 to provide force to the latch 106 to move the latch 106 from its first position to its second position. As shown in FIG. 19, in some embodiments, the mechanical actuator 539 can be in the form of a push button, and can further include a return biasing element 538 shown in the form of a spring.

When mechanical energy is applied to the mechanical actuator 539 (e.g., when the push button is pressed), the biasing element 538 is compressed and the mechanical force from the mechanical actuator 539 is applied to the latch 106, and particularly to the end of the latch 106 opposite the end retaining the rotary arm module 102, to cause the latch 106 to pivot on its pin 107 and release the rotary arm module 102, thereby releasing the firing system 101 to fire, allowing actuation of the metering dose valve of the pMDI canister 51. The firing system 101 can be re-primed as described above.

In some embodiments, the mechanical actuator 539 can be incorporated on its own to release the latch 106, or with an electronic mechanism such as one of those described above. Such an embodiment can provide a 'fail safe' arrangement for instances in which the electronic system fails.

In the previously described embodiments, the firing system 101 is configured to interact directly with the canister 51, and particularly, with the base 49 of the canister 51. However, in some embodiments, the length of the inhaler housing 55 may be greater, allowing one or more additional components to be included between the firing system 101 and the canister 51, and if required allowing differing profiles to be chosen for the plunger 103 of different inhalers. FIG. 20 illustrates an inhaler 100A that is substantially the same as the inhaler 100, except that the inhaler 100A includes an adapter (or spacer) 155 located between the firing system 101 and the base 49 of the canister 51 that is configured to accommodate the canister 51 (e.g., includes a recess dimensioned to receive at least a portion of the base 49 of the canister 51). An example of such an additional component could be a simple spacer element. Differently configured (i.e., sized and/or shaped) adapters 155 can be employed to enable various shapes and sizes of canisters to be accommodated without the need to substantially alter the firing system 101.

Flow governors and flow governor assemblies of the present disclosure will now be described in greater detail.

Figure 21:
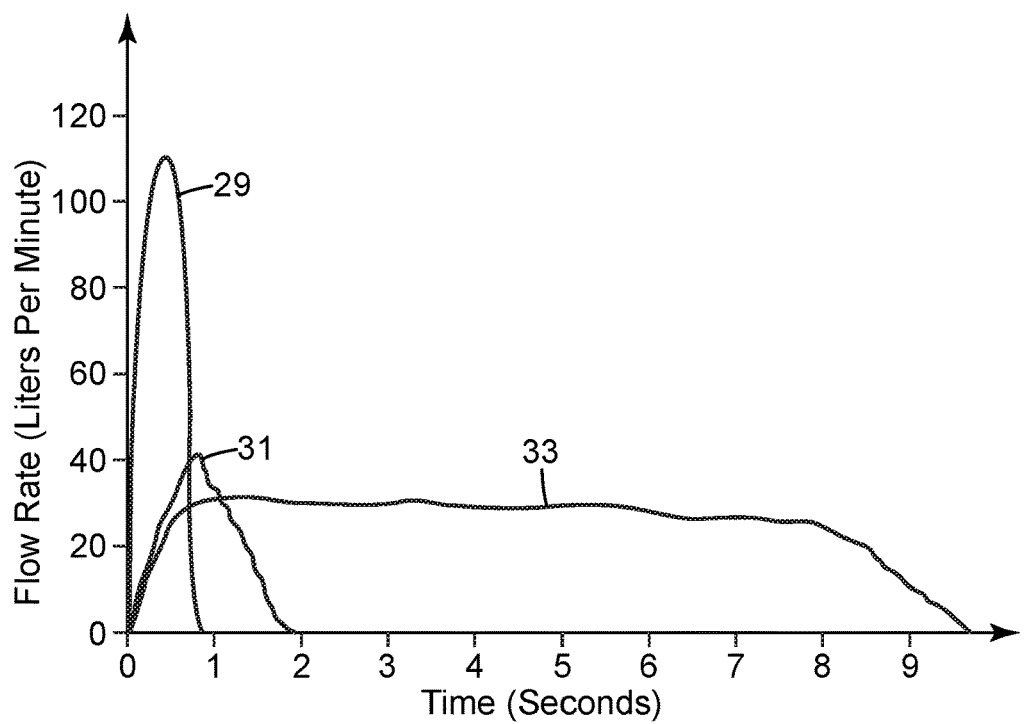
FIG. 21 is a graph schematically illustrating flow rate (L/min.) versus time (seconds) of inhalation flow profiles of COPD patients using conventional medicinal inhalers and using medicinal inhalers comprising a flow governor of the present disclosure.

FIG. 21 shows, schematically, some fairly typical chronic obstructive pulmonary disease (COPD) patient inspiratory flow rate (L/min.) versus time (seconds) profiles. In the absence of significant inhalation device resistance to air flow, some profiles 29 are characterised by a short, relatively rapid intake of breath. Other patients, e.g. with weaker lungs, are unable to either sustain long inhalations or to achieve adequate flow rates. Their profiles 31 are short and weak. Using an inhaler that comprises a flow governor of the present disclosure, however, can provide patient inspiratory profiles that are more like that denoted as 33: a longer, sustained, steady inspiratory flow rate (e.g., of around 30 L/min.) can be obtained.

COPD patients have a wide range of inhalation breathing capability and this can be represented as a distribution between 0.5 and 4 kPa pressure drop. In some embodiments, the static resistance of an inhaler of the present disclosure prior to any governing of flow by the flow governor of the present disclosure (i.e., prior to any collapse of the tubular element) can be approximately 0.8 $Pa^{0.5}$ min./L. This can be considered to be a medium resistance. In some embodiments of the present disclosure, the target governing flow rate can be 30 L/min. In some embodiments, the target breath-actuation triggering flow rate can be 15 L/min. With such a system, there is very low probability of a COPD patient not being able to reach the triggering flow rate, either through lack of inhalation effort or because any individual flow governor limits the air flow rate to less than its breath-actuation triggering flow rate. Such an inhalation device is therefore suitable for a very high proportion of COPD patients. That is, at low flow rates, the inhaler will operate like a medium resistance device, and every patient will be able to inhale up to 20 L/min. quite easily. At a somewhat greater flow rate, the flow governor's tubular element will collapse onto the internal support structure, and the inhaler will become a high resistance device. The patient will then not be able to inhale at a higher flow rate. In general, patients are likely to learn to automatically compensate their inhalation effort and will continue to inhale at a flow rate that is comfortable to them. For some patients, that will involve a pressure drop of only 0.5 kPa, but for others it will be 4 kPa or above depending upon their lung strength and capacity and upon the training the patient has previously had.

If a higher flow governor flow rate were selected (e.g., greater than 30 L/min.), then some patients would not be able to achieve the air flow rate required for the inhaler to be governed, and the variability in patient inhalation would not be minimized. If, alternatively, the inhaler were to have a higher resistance, then again some patients would not be able to achieve the governed flowrate and the variability in patient inhalation flowrate would not be minimized. With the parameters described above, however, an inhaler incorporating a flow governor of the present disclosure has the potential to:

Improve coordination of drug release with the start of inspiratory flow;

Maintain the inspiratory air flow rate to within a range of approximately 25 to 35 L/min.; and Reduce variability both in dose consistency and the location of drug deposition in the lung.

For a nominal target governing flow rate of 30 L/min., there will be a range of actual values due to manufacturing tolerances and environmental factors such as temperature and atmospheric pressure. In an embodiment where the inhaler's total static resistance is 0.83 $Pa^{0.5}$ ($minl^{-1}$), and the flow governor has a nominal governing flow of 30 L/min., any patient inhaling at a pressure drop between 0.5 kPa and 4 kPa would be expected to generate an air flow of between about 25 and 35 L/min.

In some embodiments of the present disclosure, the governing flow rate can be nominally 40 L/min. In this case, patients who can only produce a low inhalation pressure drop (e.g. about 0.5 kPa) and who typically inhale at less than 40 L/min. will not benefit from the flow governor, and their inhalation will be equivalent to inhaling through a medium resistance inhaler. Other patients who naturally inhale more strongly (i.e. at a higher pressure drop) are likely to benefit from the flow governor, and their flow rate will be restricted by the flow governor to the governing flow rate.

In some embodiments of the present disclosure, the governing flow rate can be nominally 50 L/min. In this case, only patients who inhale at a pressure drop of greater than approximately 1.5 kPa will experience flow governing. Because the governing flow rate is higher, there will be a larger spread in the Peak Inhalation Flow rates (PIF) obtained between patients: some will be able to inhale at only around 27 L/min. because this is the fastest that they can inhale through a medium resistance device, whereas others who inhale at 4 kPa could pull as much as 55 L/min. through the system.

Additional illustrations of the effects of flow governors are detailed below in the Examples section.

Figure 32:
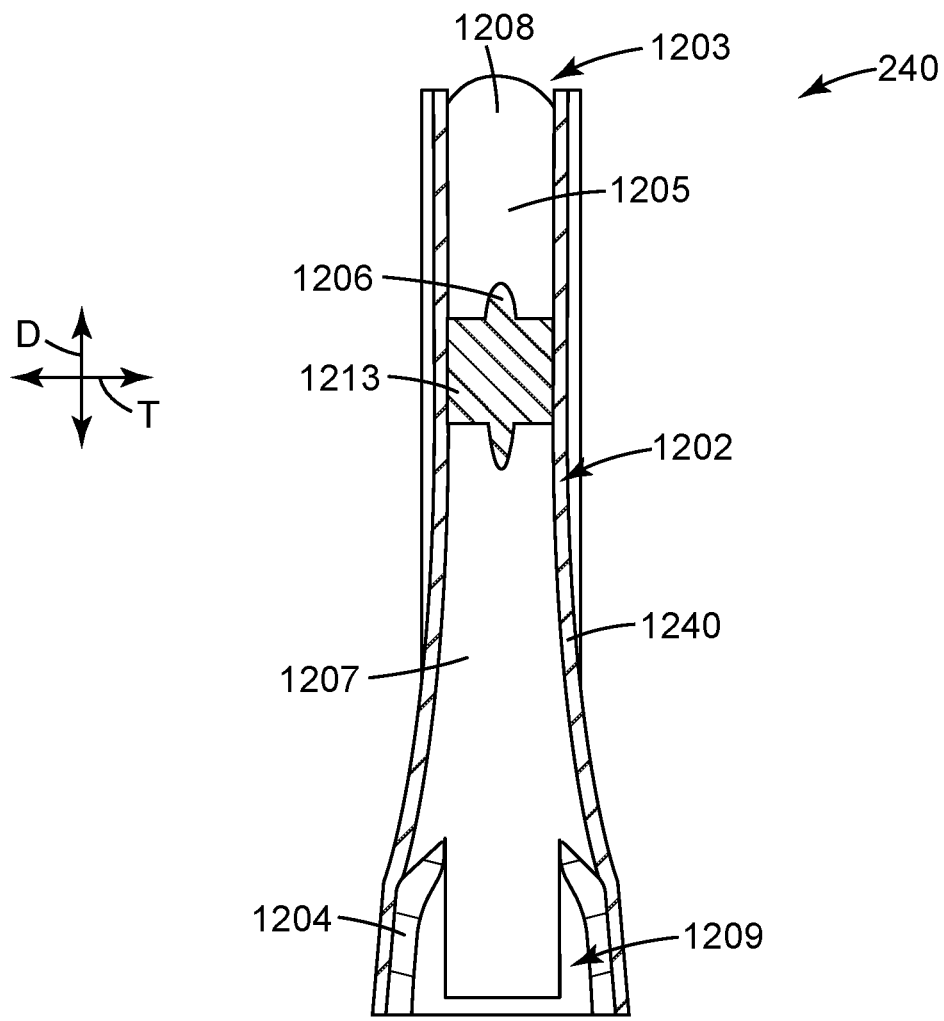
FIG. 32 is a side longitudinal cross-sectional view of the flow governor of FIGS. 28-31, shown in operation.
Figure 33:
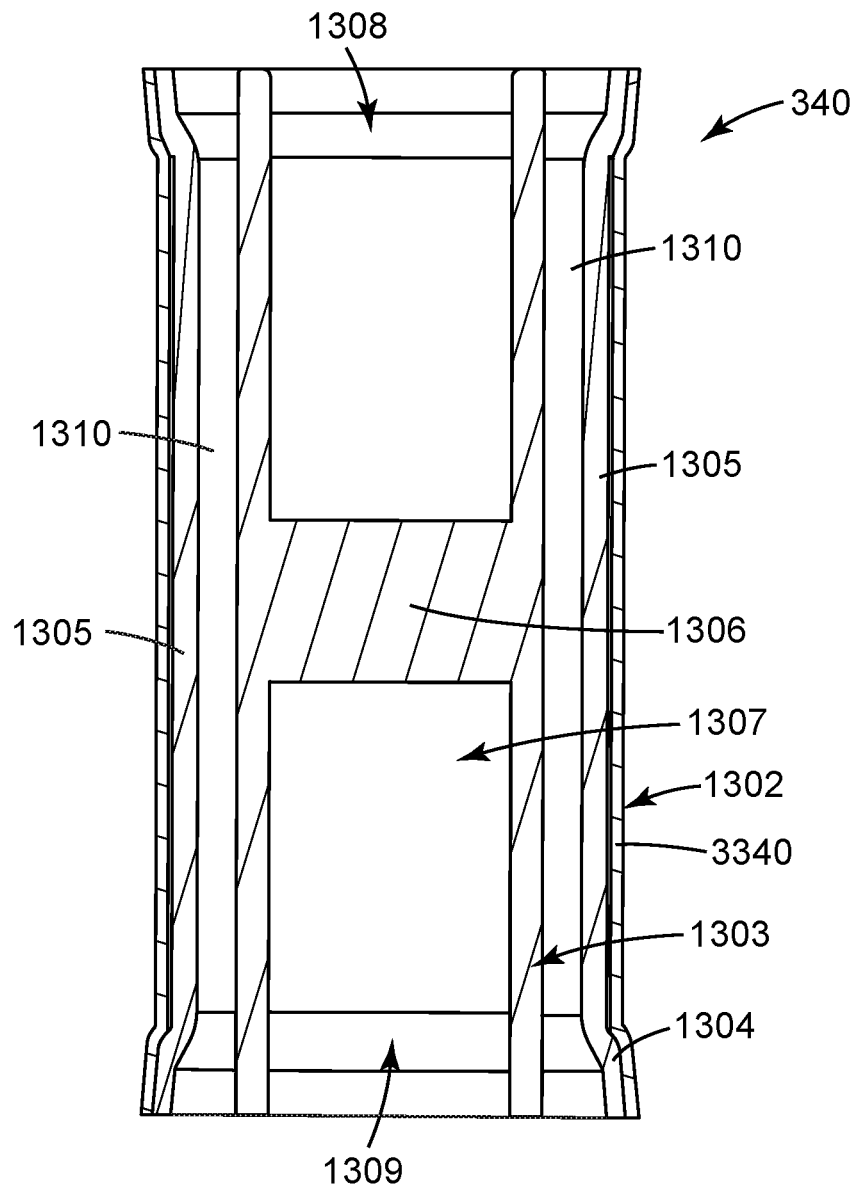
FIG. 33 is a front longitudinal cross-sectional view of a flow governor according to another embodiment of the present disclosure.
Figure 34:
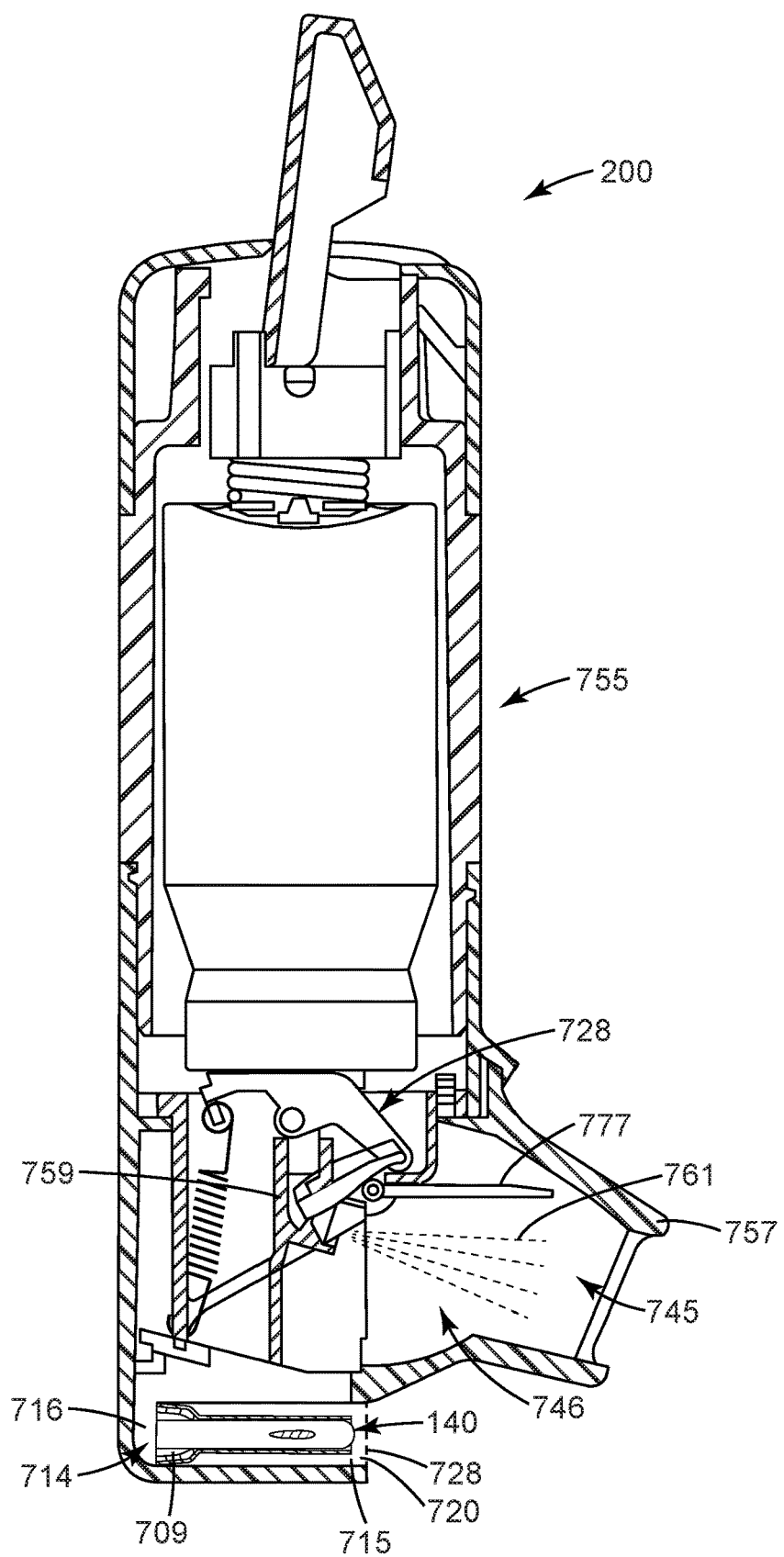
FIG. 34 is a side cross-sectional view of a breath-actuated medicinal inhaler according to one embodiment of the present disclosure, comprising the flow governor of FIGS. 22-27 located in a dedicated air flow path.

FIGS. 22-33 illustrate various embodiments of flow governors of the present disclosure. FIG. 34 illustrates an embodiment of a medicinal inhaler of the present disclosure that comprises a flow governor of the present disclosure. FIGS. 35-38 illustrate various embodiments of flow governor assemblies comprising flow governors that can be employed in medicinal inhalers of the present disclosure.

Flow Governors

Figure 24:
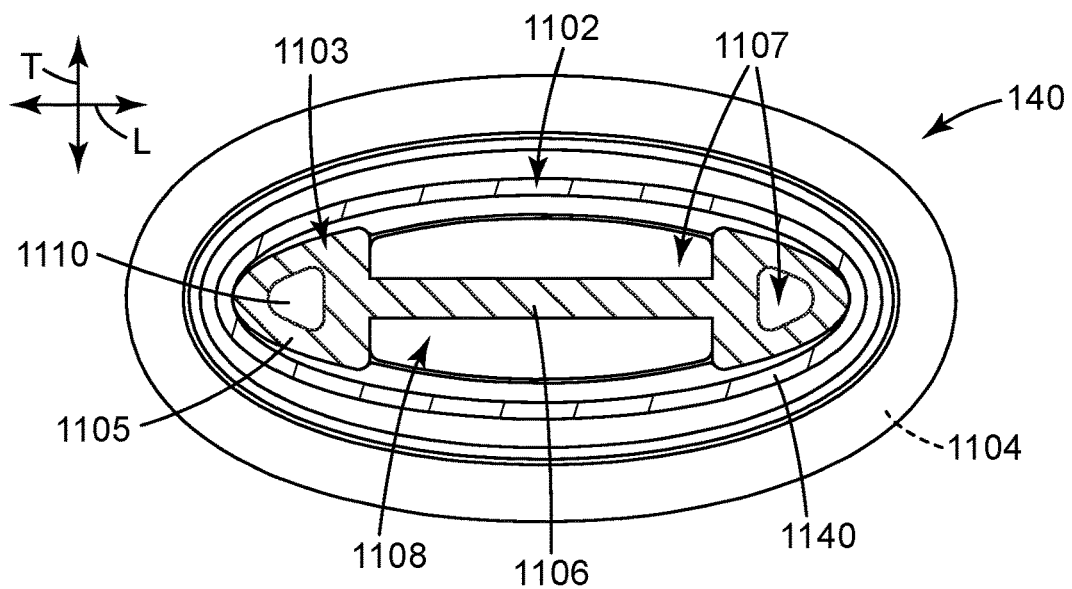
FIG. 24 is a transverse cross-sectional view of the flow governor of FIGS. 22 and 23, taken alone line 24-24 of FIG. 22, shown at rest.
Figure 25:
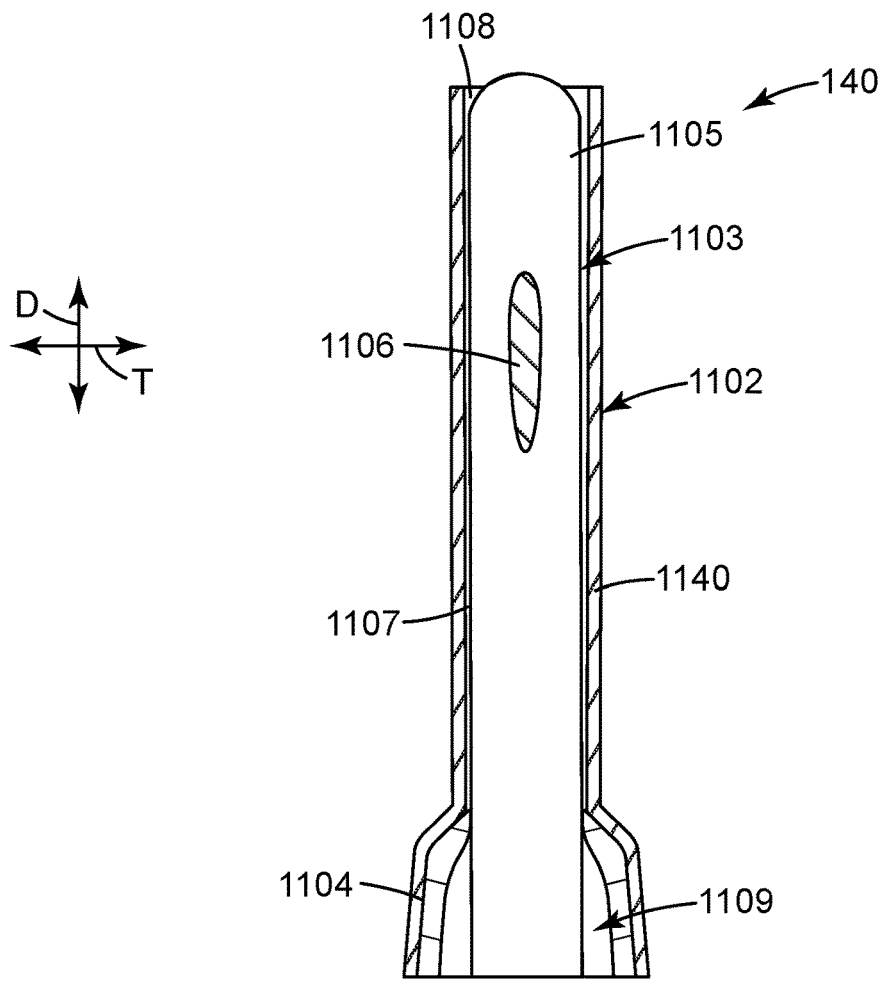
FIG. 25 is a side longitudinal cross-sectional view of the flow governor of FIGS. 22-24, taken along line 25-25 of FIG. 22, shown at rest.
Figure 26:
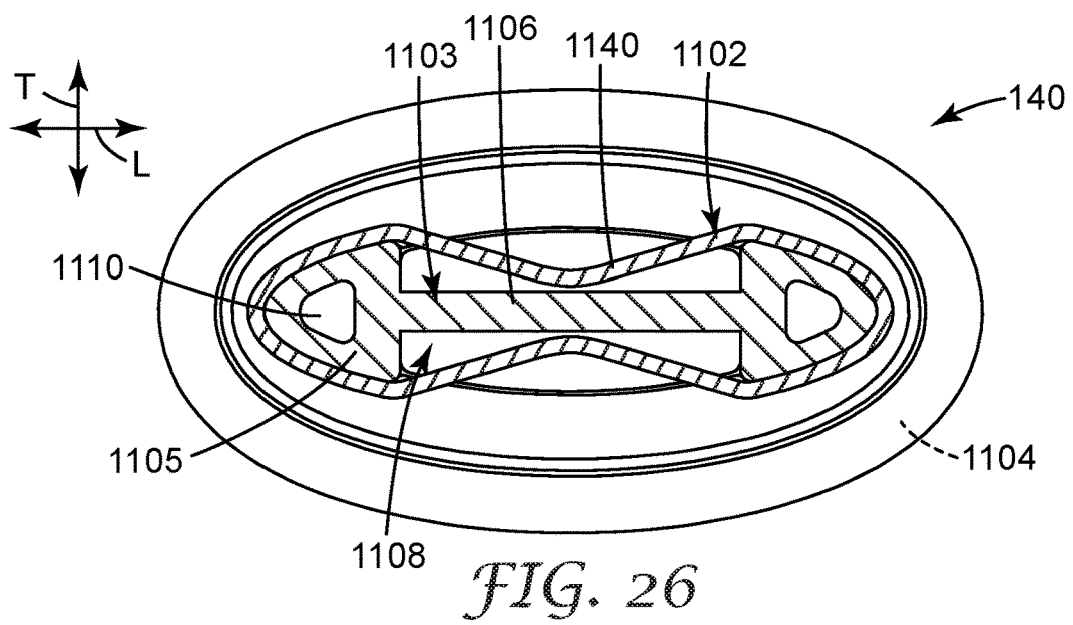
FIG. 26 is a transverse cross-sectional view of the flow governor of FIGS. 22-25, taken alone line 26-26 of FIG. 22, shown in operation.
Figure 27:
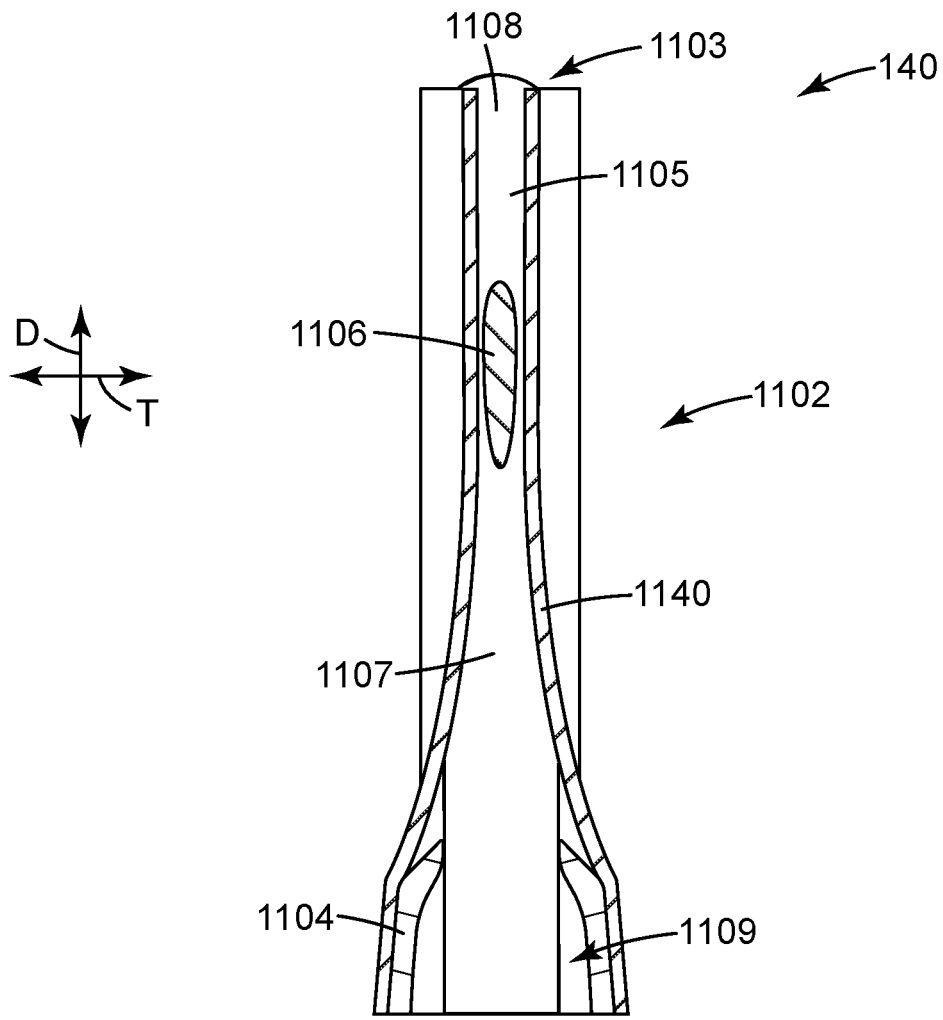
FIG. 27 is a side longitudinal cross-sectional view of the flow governor of FIGS. 22-26, taken along like 25-25 of FIG. 22, shown in operation.

FIGS. 22-27 illustrate a flow governor 1101 according to one embodiment of the present disclosure. FIGS. 22-25 show the flow governor 140 at rest, and FIGS. 26-27 show the flow governor 140 in operation.

As shown, the flow governor 140 includes an outer flexible tubular element (or "tube") 1102 comprising at least one flexible wall 1140, and an internal support structure 1103 that is dimensioned to be received within the tubular element 1102 (i.e., within the at least one flexible wall 1140). In the embodiment of FIGS. 22-27, the internal support structure 1103 includes a hollow base 1104, two hollow (e.g., tubular) pillars 1105 and a cross member (or "cross-beam") 1106.

The outer diameter of the hollow base 1104 of the illustrated embodiment is greater than an initial inner diameter of the tubular element 1102, and assembly of the two components can be achieved by stretching the tubular element 1102 over an outer portion (e.g., an outer wall) of the hollow base 1104. This positioning results in the originally circular cross-section of the tubular element 1102 being deformed into an approximately elliptical (or oblong) cross-sectional (i.e., in transverse cross-section) shape. In some embodiments, such an elliptically-shaped tubular element 1102 can have a major axis (externally) of approximately 12 mm and a minor axis (externally) of approximately 4 mm.

Other formation and/or assembly means are alternatively possible, however, as will be apparent to a person of ordinary skill in the art. For example, the tubular element 1102 could instead be over-molded onto an outer surface of the hollow base 1104 of the internal support structure 1103, or it could be stretched and then coupled to the outer surface of the base 1104 by a variety of coupling means, including, but not limited to, one or more of adhesives, cohesives, welding (e.g., sonic [e.g., ultrasonic] welding), any thermal bonding or heat sealing technique (e.g., heat and/or pressure applied to one or both of the components to be coupled), other suitable coupling means, or combinations thereof.

In some embodiments, the internal support structure 1103 can be coupled to or integrally formed with a portion of a housing that forms an air flow path or an inhaler of the present disclosure. For example, in some embodiments, the internal support structure 1103 can be provided by (e.g., integrally formed with) the housing that forms at least a portion of an inhaler housing.

As shown in FIGS. 22-25, the flow governor 140, and the tubular element 1102, can be substantially linear. Furthermore, the flow governor 140 can have an air flow path 1107 including an air inlet 1108 located at a first (longitudinal) end and an air outlet 1109 located at a second (longitudinal) end that generally define an air flow direction that is generally oriented along a longitudinal direction D. The tubular element 1102 can be elongated in the longitudinal direction D. The at least one flexible wall 1140 of the tubular element 1102 can be oriented substantially parallel to the longitudinal direction D; the hollow pillars 1105 can be oriented substantially parallel to the longitudinal direction D; and the cross member 1106 can be oriented at a non-zero angle (e.g., substantially perpendicularly) with respect to the longitudinal direction D, i.e., substantially parallel with respect to a lateral direction L (which can represent a side-to-side direction of the flow governor 140). A third transverse direction T is oriented substantially perpendicularly with respect to the longitudinal direction D and the lateral direction L, and can represent a front-to-back direction of the flow governor 140.

The tubular element 1102 (i.e., the at least one flexible wall 1140) can be formed of a variety of materials, including, but not limited to, one or more of silicone rubber, other thermoplastic elastomers, or combinations thereof. In addition to its flexibility, the tubular element 1102 can be formed of a material that is resilient, in order that it returns to its rest shape and position when air flow through it ceases, i.e., the tubular element 1102 can deform elastically and spring back ready for its next cycle of use. The material may be chosen according to specific property needs, e.g. if it is to be over-molded, glued or ultrasonically welded to the hollow base 1104 of the internal support structure 1103. It will be obvious to one skilled in the art that the chosen tubular element material should have good long term physical and chemical stability.

While the tubular element 1102 can suitably have a relaxed transverse cross-sectional shape that is substantially circular (and which can be stretched to an elliptical cross-sectional shape over the base 1104 of the internal support structure 1103), other cross-sectional shapes are possible, such as those described above in the definition of "tubular." It should also be noted that the base 1104 can be elliptical in its transverse cross-sectional shape or can be another shape. In some embodiments, the base 1104 is elliptical, the ellipse having the special case shape of a circle. In some embodiments employing a transverse cross-sectional shape of the base 1104 that is circular, or is close to circular, can assist in ensuring that the tubular element 1102 can be assembled onto it without imposing significant residual torsional strains into it. Furthermore, in some embodiments, the tubular element 1102 can be formed of more than one material, or can have different sections (e.g., sequentially along its longitudinal direction) with different wall thicknesses and/or diameters, such that certain sections of the tubular element 1102 are more flexible than others and can preferentially collapse.

In some embodiments, the tubular element 1012 can be formed of a silicone rubber tube of approximately 0.3 mm wall thickness, 8.0 mm initial inside diameter, 20 mm length and 60 OO Shore hardness.

Figure 23:
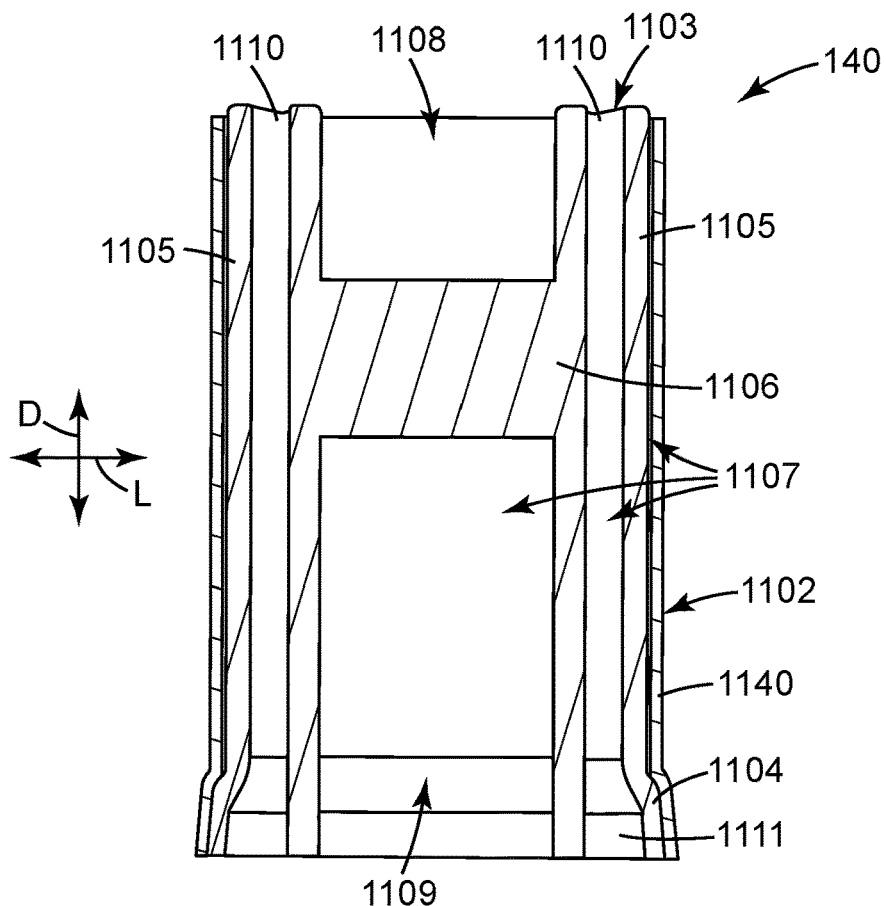
FIG. 23 is a front longitudinal cross-sectional view of the flow governor of FIG. 22, taken along line 23-23 of FIG. 22, shown at rest.

In some embodiments, the internal support structure 1103 can have an "H" shaped longitudinal cross-sectional shape (i.e., taken along the longitudinal direction D), as shown in FIG. 23. However, as shown in FIG. 23, in some embodiments, the cross member 1106 may not be longitudinally centered with respect to the overall dimension (e.g., height) of the internal support structure 1103 in the longitudinal direction D, but rather, the cross member 1106 may be located toward the air inlet end (e.g., an upstream end) of the internal support structure 1103.

Additionally, or alternatively, in some embodiments, the internal support structure 1103 can have a generally "H" shaped (i.e., generally similar to a capital English letter H) transverse cross-sectional shape (i.e., taken substantially orthogonally with respect to the longitudinal direction D, e.g., in the lateral direction L or the transverse direction T), as shown in FIG. 24. Furthermore, in some embodiments, the internal support structure 1103 can be formed of an injection molded plastic, such as polypropylene, acetal, ABS (acrylonitrile butadiene styrene), polycarbonate or polyethylene, or can be made from a metal or metal alloy (e.g., machined, stamped/pressed or metal injection molded) or from a ceramic material (e.g. ceramic injection molded). In some embodiments, the internal support structure 1103 can be formed as a single integral component, i.e., formed from one part.

As shown in FIG. 24, in some embodiments, the cross member 1106 of the internal support structure 1103 can be substantially centered with respect to the pillars 1105 in the transverse direction T, which gives the generally "H" shaped transverse cross-sectional shape. In addition, by way of example, the illustrated internal support structure 1103 of FIGS. 22-27 has lateral symmetry about a central longitudinal axis (i.e., about a central transverse-longitudinal plane), as well as transverse symmetry (e.g., front-to-back) about the central longitudinal axis (i.e., about a central lateral-longitudinal plane). Said another way, the internal support structure 1103 is symmetrical about a central longitudinal axis in the lateral direction D and the transverse direction T.

As will be described in greater detail below, only the air outlet end of the tubular element 1102 is fixed and supported (i.e., by the base 1104 of the internal support structure 1103), whereas the air inlet end of the tubular element 1102 is freestanding and able to collapse onto the internal support structure 1103.

The assembly of the tubular element 1102 and the internal support structure 1103 forms the air flow path 1107, including the air inlet 1108 and the air outlet 1109. FIG. 24 shows a transverse cross-section of the flow governor 140, which illustrates that the tubular element 1102 has an approximately elliptical cross-section once stretched onto the base 1104 of the internal support structure 1103, and also shows two lumens 1110, located within the two hollow pillars 1105, which act as residual air flow channels, i.e., function as a portion of the air flow path 1107 through the flow governor 140. By way of example only, the lumens 1110 are shown as having an approximately triangular shape in the transverse cross-section. In some embodiments, each of the two lumens 1110 can have an open cross-sectional area of approximately 1 mm$^2$.

FIG. 25 shows a side longitudinal cross-section of the flow governor 140, which illustrates that the tubular element 1102 runs substantially parallel to the hollow pillars 1105, but is not in contact with them. At the air inlet 1108, the hollow pillars 1105 can protrude from the tubular element 1102. With reference to FIG. 23, it may be noted that air flow entering the pillar lumens 1110 will exit at a bypass outlet 111 of each pillar 1105, prior to passing through the hollow base 1104.

One primary function of the flow governors of the present disclosure is to govern air flow when the patient inhales through a medicinal inhaler, limiting the patient's inspiratory flow rate to a narrow and controlled range in order to avoid excessively fast inhalation and consequently excessive mouth and throat drug deposition. The flow governors of present disclosure are thus able to aid in the attainment of increased deep lung drug penetration and deposition.

Use of such a flow governor allows patients with poor lung function (e.g. particularly poorly COPD patients) to experience a relatively low inhaler air flow resistance (allowing them to inhale sufficient air in a reasonable degree of comfort) while giving patients with stronger lungs a transiently higher air flow resistance to inhale against (thereby allowing them to inhale for longer and more deeply, while at the same time limiting their inhalation air flow rate to a level very similar to that of weaker patients). In other words, the inspiratory air flow rate can be kept much more consistent between patients and between inhalations. Medication delivery is thus much more predictable, allowing physicians to prescribe treatment regimes with an improved level of confidence.

While FIGS. 22-25 illustrate the flow governor 140 at rest (i.e., with the tubular element 1102 in an uncollapsed state); FIGS. 26 and 27 show the flow governor 140 in an operative state (i.e. with the patient's inspiratory air flow substantially passing through it and with the tubular element 1102 in a collapsed state). When air is sucked towards the air outlet 1109, it flows via the air inlet 1108 into the air flow path 1107, around the pillars 1105 and cross member 1106 (i.e., through any gap still present between the pillars 1105 and the tubular element 1102 and between the cross member 1106 and the tubular element 1102), and through the pillar lumens 1110. The speed of the passing air flow through the air flow path 1107 creates a reduction in air pressure in the air flow path 1107 (i.e., according to the Bernoulli Effect). In the embodiment illustrated in FIGS. 22-27, the reduced pressure in the air flow path 1107 causes a reduction in the diameter along the minor axis of the elliptical cross-sectioned tubular element 1102 (i.e., in the transverse direction T) resulting in inward bending, as shown in FIGS. 26 and 27. Because the tubular element 1102 is supported at one end (i.e., its outlet end, toward the air outlet 1109) by the hollow base 1104, the inward bending occurs predominantly at the end of the tubular element 1102 that is towards the air inlet 1108, the inward bending restricting the cross-sectional area of the air flow path 1107.

To an extent, the greater the reduction in pressure in the air flow path 1107, the greater the inward bending of the tubular element 1102. The resultant reduction in the cross-sectional area of the air flow path 1107 leads to an increased resistance to air flow rate. However, because the air flow path 1107 of the flow governor 140 is only one part of the total overall resistance to air flow of the medicinal inhaler in which the flow governor 140 is employed (e.g. it might be around 50% or less of the total inhaler air flow resistance if the inhaler has a moderate static resistance to air flow), then the mass flow rate of air through the flow governor 140 does not fall in proportion to its reduced residual cross-sectional area. This means that the velocity of air through the residual air flow path 1107 within the collapsed tubular element 1102 rises as the tubular element 1102 collapses, further increasing the Bernoulli forces upon it. This effect tends to lead to substantial bistability in the operation of the flow governor 140. That is, the initiation of collapse leads to "positive feedback" which reinforces the inwards collapse-driving Bernoulli forces until they are eventually balanced by the resistive stiffness forces of the material of the tubular element 1102. In other words, in some embodiments, the flow governor 140 can be substantially bistable, where it tends to be in one of two states at any time: either it is in a substantially 'open' or 'uncollapsed' state, or it is in a substantially 'collapsed' state.

Complete collapse of the elliptical cross-section tubular element 1102 is prevented by the hollow pillars 1105. These pillars 1105, together with the cross member 1106, provide structural support that prevents significant reduction in the diameter along the major axis of the elliptical cross-section tubular element 1102 (i.e., in the lateral direction L). The air flow bypasses provided by the lumens 1110 allow a base level of residual air flow to continue to flow. In addition, the finite stiffness of the tubular element 1102 means that small additional gaps are left around the corners of the internal support structure 1103 where the tubular element 1102 cannot bend sufficiently to close off all the small residual air passageways or gaps between the internal support structure 1103 and the tubular element 1102 (see, e.g., FIG. 26). Thus, at least a minimum, or residual, air flow can always continue to flow. That is, the reduced pressure can never reach a value sufficient for the tubular element 1102 to collapse completely and to seal off all air flow through the flow governor 140.

The point at which the tubular element 1102 collapses and the flow rate at which the flow governor governs are dependent on the geometry of the internal support structure 1103 (and particularly, on the cross-sectional area of the pillar lumens 1110), and the properties of the tubular element 1102, in particular its wall thickness, air inlet cross sectional area, width, length and Shore hardness. For the tubular element 1102, material that has a low adhesive characteristic can also be preferable, to ensure a smooth transition from the collapsed to the open state by prevention of adhesion to a housing wall of an inhaler in which the flow governor 140 is positioned and/or to the internal support structure 1103.

As described in greater detail in the Examples section, mathematical modeling of flow governors of the type shown in FIGS. 22-27 has demonstrated that the flow governors of one embodiment of the present invention are capable of governing at an air flow of 30 L/min. with a repeatability and consistency of ±5 L/min. over a wide range of patient pressure drops. Almost all patients, even those with very weak lungs, should be capable of achieving such air flow rates, yet because of the operation of the flow governor, no patients are likely to be able to exceed such air flow rates, even with very excessive effort.

Other arrangements of the embodiment described, such as the shape, size, number and location of elements belonging to the internal support structure, will be apparent to one skilled in the art.

Other designs or configurations of the internal support structure may be used instead of the hollow pillar and cross member arrangement of FIGS. 22-27. For example, FIGS. 28-33 illustrate various flow governors of the present disclosure, wherein like numerals represent like elements. FIGS. 28-32 illustrate a flow governor 240 according to another embodiment of the present disclosure that employs a different internal support structure; and FIG. 33 illustrates a flow governor 340 according to yet another embodiment of the present disclosure. The flow governors of FIGS. 28-33 share many of the same elements, features, and functions as the flow governor 140 of FIGS. 22-27. Reference is made to the description above accompanying FIGS. 22-27 for a more complete description of the features and elements (and alternatives to such features and elements) of the embodiments illustrated in FIGS. 28-33. Any of the features described above with respect to FIGS. 22-27 can be applied to the embodiments of FIGS. 28-33, and vice versa.

Figure 28:
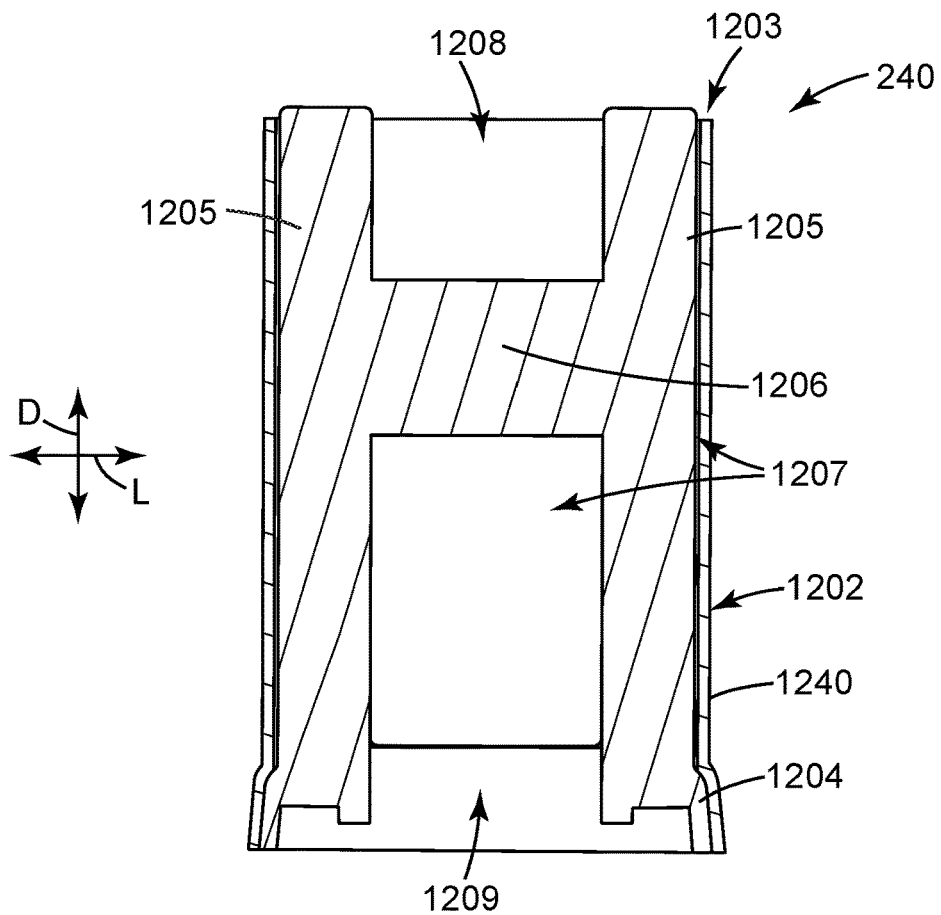
FIG. 28 is a front longitudinal cross-sectional view of a flow governor according to another embodiment of the present disclosure, shown at rest.
Figure 29:
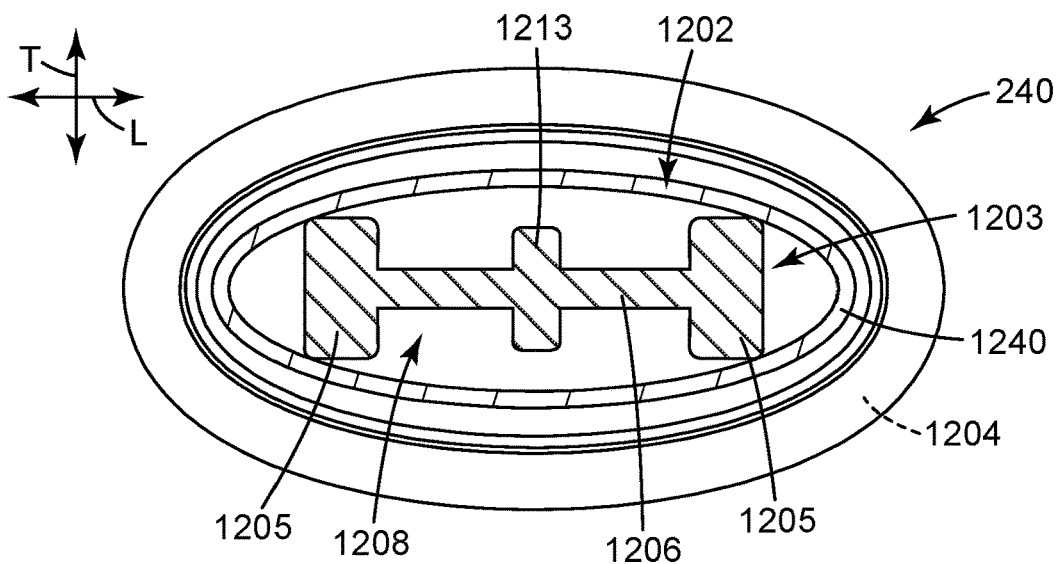
FIG. 29 is a transverse cross-sectional view of the flow governor of FIG. 28, shown at rest.

With reference to FIGS. 28-32, the flow governor 240 includes a tubular element 1202 comprising at least one flexible wall 1240, and an internal support structure 1203. In this embodiment, the internal support structure 1203 includes a hollow base 1204, solid pillars 1205 (i.e., with no lumens), a cross member 1206, and one or more splines (or transverse protrusions or transverse splines) 1213 (see FIGS. 29 and 31) protruding from the cross member 1206 (e.g., protruding transversely from the laterally oriented cross member 1206). In some embodiments, as shown, the one or more transverse protrusions 1213 can be located laterally centrally with respect to the internal support structure 1203 and protruding forwardly and rearwardly with respect to the cross member 1206 (i.e., when viewed in transverse cross-section, as shown in FIG. 29). In some embodiments, the one or more transverse protrusions 1213 can protrude from the internal support structure 1203 substantially orthogonally with respect to the at least one flexible wall 1240 of the tubular element 1202.

Figure 31:
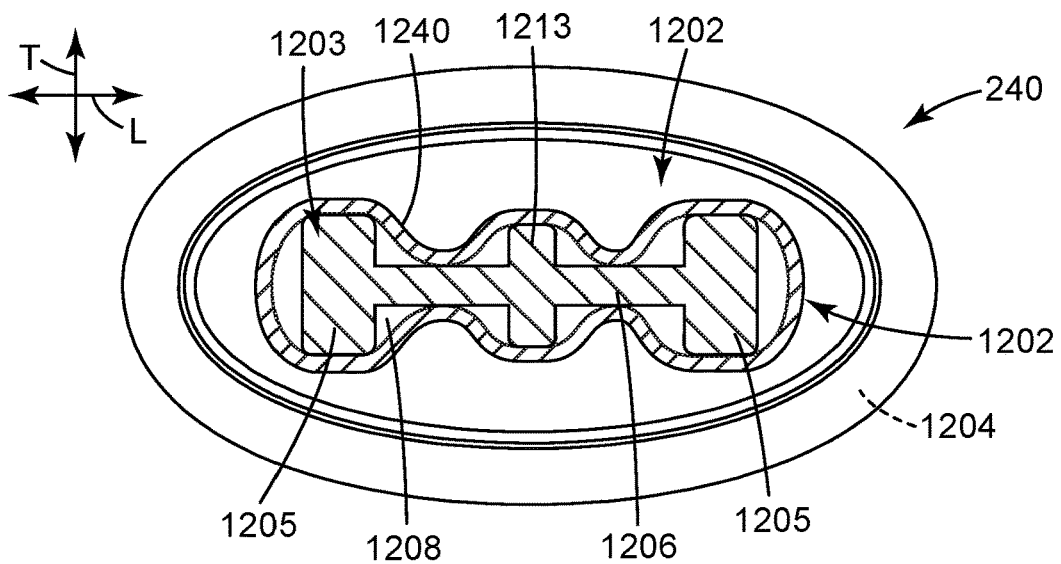
FIG. 31 is a transverse cross-sectional view of the flow governor of FIGS. 28-30, shown in operation.

By way of example only, the internal support structure 1203 has an "H" shaped longitudinal cross-sectional shape (i.e., taken along the longitudinal direction D), as shown in FIG. 28 and a generally "H" shaped transverse cross-sectional shape (i.e., taken substantially orthogonally with respect to the longitudinal direction D, e.g., in a lateral-transverse plane), as shown in FIGS. 29 and 31.

Furthermore, in embodiments employing at least one transverse protrusion 1213, the internal support structure 1203 can further include a transverse cross-sectional shape including at least one capital English letter "E." Particularly, in embodiments employing two laterally-centered transverse protrusions 1213, as shown in FIGS. 29 and 31, the internal support structure 1203 can have a transverse cross-sectional shape including two capital letter "E"s, merged back-to-back and oriented with the long side of the "E" in the lateral direction L. Unlike the hollow pillars 1105 of FIGS. 22-27, the solid pillars 1205 lack any internal lumen with long aspect ratios, and therefore have a geometry that may be more desirable for ease of manufacture. Other arrangements, not necessarily "H"-shaped in longitudinal or transverse cross-section, will also be apparent to one skilled in the art. Examples include flow governors having one or more internal support structures having transverse cross-sectional shapes including, or similar to, any of the letters selected from the English capital letters of B, C, D, E, H, M, N, O, S, V, W, X and Z. Other shapes will also be apparent to one of ordinary skill in the art.

Figure 30:
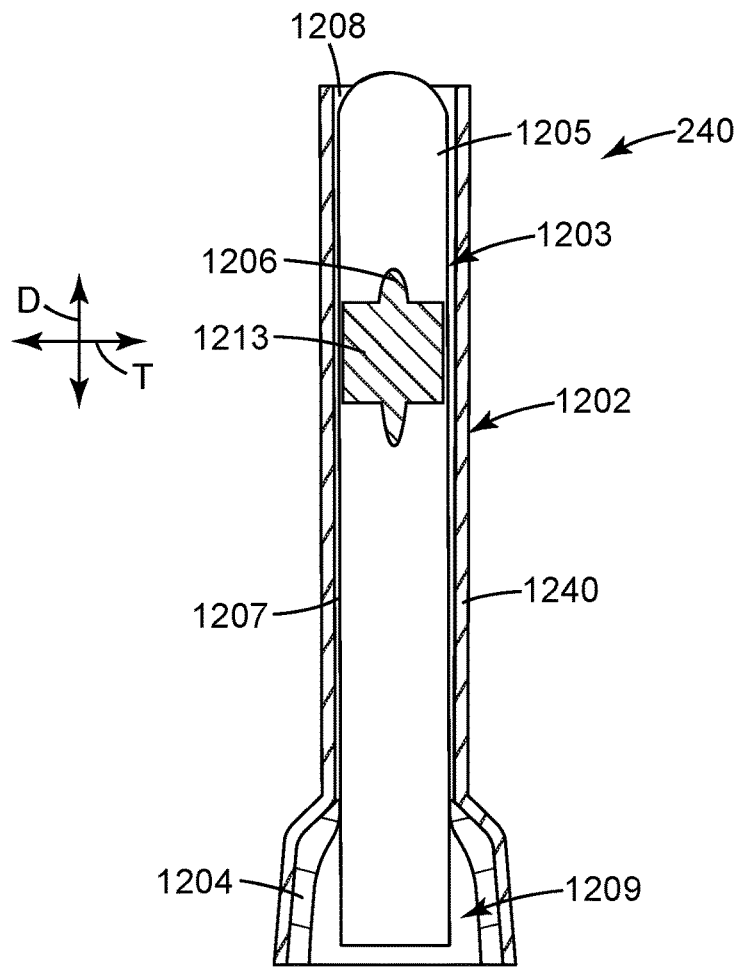
FIG. 30 is a side longitudinal cross-sectional view of the flow governor of FIGS. 28-29, shown at rest.

FIGS. 28-30 illustrate the flow governor 240 at rest (i.e., with the tubular element 1202 in an uncollapsed state), and FIGS. 31-32 illustrate the flow governor 240 in an operative state (i.e., with the tubular element 1202 in a collapsed state).

The flow governor 240 includes an air flow path 1207 formed between the internal support structure 1203 and the tubular element 1202, the air flow path 1207 including an air inlet 1208 and air outlet 1209. FIG. 29 shows a transverse cross-section of the flow governor 240, taken generally perpendicularly with respect to the general direction of air flow, which illustrates that the tubular element 1202 has an approximately elliptical transverse cross-sectional shape at rest. In some embodiments, as shown, the splines 1213 protrude outwardly from the cross member 1206 (e.g., in the transverse direction T) less than the solid pillars 1205 do. In alternative embodiments, the splines can be dimensioned to protrude an equal distance from the cross member 1206 as the solid pillars 1205, or alternatively, can protrude further. Alternatively, each solid pillar 1205 can have a transverse cross-sectional shape in the form of a cross rather than an approximate rectangle. Many more variants to the cross-sectional shape and dimensions of the internal support structure 1203 are possible, as will be apparent from these examples. Each variant will have its own air flow characteristics as a function of pressure drop and air flow rate, in combination with the characteristics of the form and material of the tubular element 1202.

FIG. 30 illustrates that the tubular element 1202 and the solid pillars 1205 are oriented generally parallel to the longitudinal direction D, and that the tubular element 1202 is not in contact with the solid pillars 1205 at rest, and that the pillars protrude from the tubular element 1202 at the air inlet 1208 (i.e. protrude from an upstream end of the tubular element 1202.

FIGS. 31 and 32 illustrate the flow governor 240 in an operative state. When air is sucked through the air outlet 1209, it flows into the air flow path 1207 via the air inlet 1208. As shown, the reduced air pressure created by the patient's inhalation causes a reduction in diameter along the minor axis of the elliptically sectioned tubular element 1202 resulting in inward bending as shown in FIG. 31. As the tubular element 1202 is supported at the downstream end by the hollow base 1204, inward bending occurs predominantly at the end of the tubular element 1202 that is nearer to the air inlet 1208, the inward bending restricting the cross-sectional area of the air flow path 1207. The lower the air pressure in the air flow channel 1207, the greater the inward deformation of the tubular element 1202 and hence, the greater the reduction in the cross-sectional area of the air flow path 1207 and the greater the resistance to air flow.

Complete collapse of the elliptical cross-sectioned tubular element 1202 is prevented by the solid pillars 1205. These structures, along with the cross member 1206, provide structural support that prevents significant reduction in the diameter along the major axis of the elliptically sectioned tubular element 1202. The splines 1213 additionally provide support along the minor axis, preventing the tubular element 1202 (and particularly, the at least one flexible wall 1240) from collapsing too tightly onto the cross member 1206. Residual air flow is thus always possible via the residual air flow channel gaps, no matter how great the patient's inspiratory pressure drop.

FIG. 33 illustrates a flow governor 340 according to another embodiment of the present disclosure. The flow governor 340 includes a tubular element (or "tube") 1302 comprising at least one flexible wall 1340, and an internal support structure 1303 that is dimensioned to be received within the tubular element 1302 (i.e., within the at least one flexible wall 1340). The tubular element 1302 surrounds and envelopes the internal support structure 1303. The internal support structure 1303 consists of a hollow base 1304, two hollow pillars 1305 (each comprising a lumen 1310), and a cross member 1306. As shown in FIG. 33, in some embodiments, the tubular element 1302 can be anchored or otherwise attached (e.g., to the internal support structure 1303) at both ends, rather than being free at the air inlet end. As shown in FIG. 33, in some embodiments, the cross member 1306 can be located longitudinally centrally with respect to the pillars 1305. As a result, in addition to the lateral and transverse symmetries of previous embodiments, the internal support structure 1303 (and the flow governor 340) can also have longitudinal symmetry (e.g., about a central lateral-transverse plane).

As with previous embodiments, the outer diameter of the hollow base 1304 is larger than the inner diameter of the flexible tubular element 1302, and assembly of the two components is achieved by stretching the tubular element 1302 over the outer surface of the hollow base 1304. The tubular element 1302 and the internal support structure 1303 together define an air flow path 1307 therebetween that includes an air inlet 1308 and an air outlet 1309. The air flow path 1307 also includes the lumens 1310 through the pillars 1305. When air is sucked towards the air outlet 1309, it flows into the air flow path 1307 and through (i.e., via) the lumens 1310 and around the pillars 1305 via the air inlet 1308, creating a reduction in air pressure in the air flow path 1307 by the Bernoulli Effect. The reduced pressure in the air flow path 1307 causes a reduction in the diameter along the minor axis of the elliptical cross-section of the tubular element 1302 centered at approximately the midpoint of the air flow path 1307.

One possible advantage of having the tubular element 1302 secured at both ends is that the tubular element 1302 can be of greater thickness for a given flow governing performance, thereby offering a manufacturing advantage with regard to the dimensional specification range of the tubular element 1302. Another possible advantage of having the tubular element 1302 secured at both ends is that the use of a symmetrical arrangement (e.g., symmetrical longitudinally, laterally and transversely) can offer a manufacturing benefit, as it does not require a consistent and specified end-to-end orientation during assembly.

FIG. 34 illustrates an inhaler 200 according to another embodiment of the present disclosure that employs a flow governor 140 of the present disclosure and a mechanically-triggered breath-actuated firing system. By way of example only, the medicinal inhaler 200 is shown in FIG. 34 as including the flow governor 140 of FIGS. 22-27; however, it should be understood that any flow governor of the present disclosure can be employed in the inhaler 200. By way of example, the inhaler 200 is illustrated as being a variant of an inhaler available under the trade designation AUTOHALER™ from 3M Company, St. Paul, MN Additional details regarding the inhaler 200 can be found in U.S. Pat. No. 7,296,567, which is incorporated herein by reference in its entirety.

As shown in FIG. 34, the flow governor 140 is positioned in a dedicated air flow path 714 located in a bottom portion of a housing 755 of the inhaler 200, which is integrally formed with the housing 755. The dedicated air flow path 714 includes an air inlet 715 (e.g., defined by an auxiliary open end 720) open to ambience and an air outlet 716 in fluid communication with an air flow path 746 of the inhaler 200. Particularly, the dedicated air flow path 714 is arranged substantially horizontally, such that the air inlet 715 is located generally below the mouthpiece 757. Sealing means (not shown) are provided to ensure that there are no significant air leak inlets elsewhere in the inhaler 200, in order that substantially all the air flow through the inhaler 200 passes through the dedicated air flow path 714.

In this embodiment, the inspiratory air flow is drawn via the air inlet 715 (e.g., via an inlet grill, screen or grate 728) into the flow governor 140 and thence into the region around a stem socket 759. When the patient inhales on the mouthpiece 757 of the inhaler 200 (which defines an inspiration orifice 745), a vane 777 lifts in the inspiratory air flow, that lifting triggering a mechanical dose release mechanism 728. The emerging medicament formulation spray 761 is entrained in the air flow from the air outlet 709 of the flow governor 140 and the air outlet 716 of the dedicated air flow path 714 and emerges with the air flow via the mouthpiece 757. It will be noted by one skilled in the art that flow governors of the present invention may be positioned in multiple locations in such an inhaler, e.g. at the rear of the inhaler, at the front, on the top, to one side, etc. Additionally, it will be apparent that the outer form of the inhaler can be shaped and styled independently of the internal air flow surfaces.

Again, incorporation of an appropriate electronic memory device could allow capture, storage and retrieval of the patient's inhalation profile (flow rates, pressure drops, etc.) corresponding to each time the inhaler was used. Inclusion of a means to transmit the data, e.g. via a cable or using wireless technology, to a secondary device, e.g. a computer or 'smart' phone, could make these data readily available to the patient's physician or others, in order to allow them to monitor the patient's ability to use the inhaler successfully and to allow appropriate and timely health care advice to be provided based on analysis and interpretation of the retrieved information.

In alternative embodiments, the breath-actuated inhaler can include both a reusable and a replaceable part. For example, a reusable part containing the complex and relatively expensive electronics could be paired in turn with a series of replaceable medicament containing cartridges. In such embodiments, the flow governor can be associated with the replaceable cartridge or, alternatively and preferably, with the reusable unit. In either case, the air flow path of the inhaler can be configured to pass through either the reusable part, the replaceable refill part, or both.

In yet another embodiment, two or more flow governors with differing resistances and/or collapse characteristics can be incorporated into a medicinal inhaler of the present disclosure, or an air flow path of the present disclosure for use with a medicinal inhaler, for example, in a parallel flow path configuration. In a still further embodiment, two or more flow governors with differing resistances and/or collapse characteristics can be incorporated into a medicinal inhaler or air flow path of the present disclosure in a series flow path arrangement. Such embodiments can provide a greater ability to adjust the flow rate versus pressure drop characteristics of medicinal inhalers.

Flow Governor Assemblies

Figure 35:
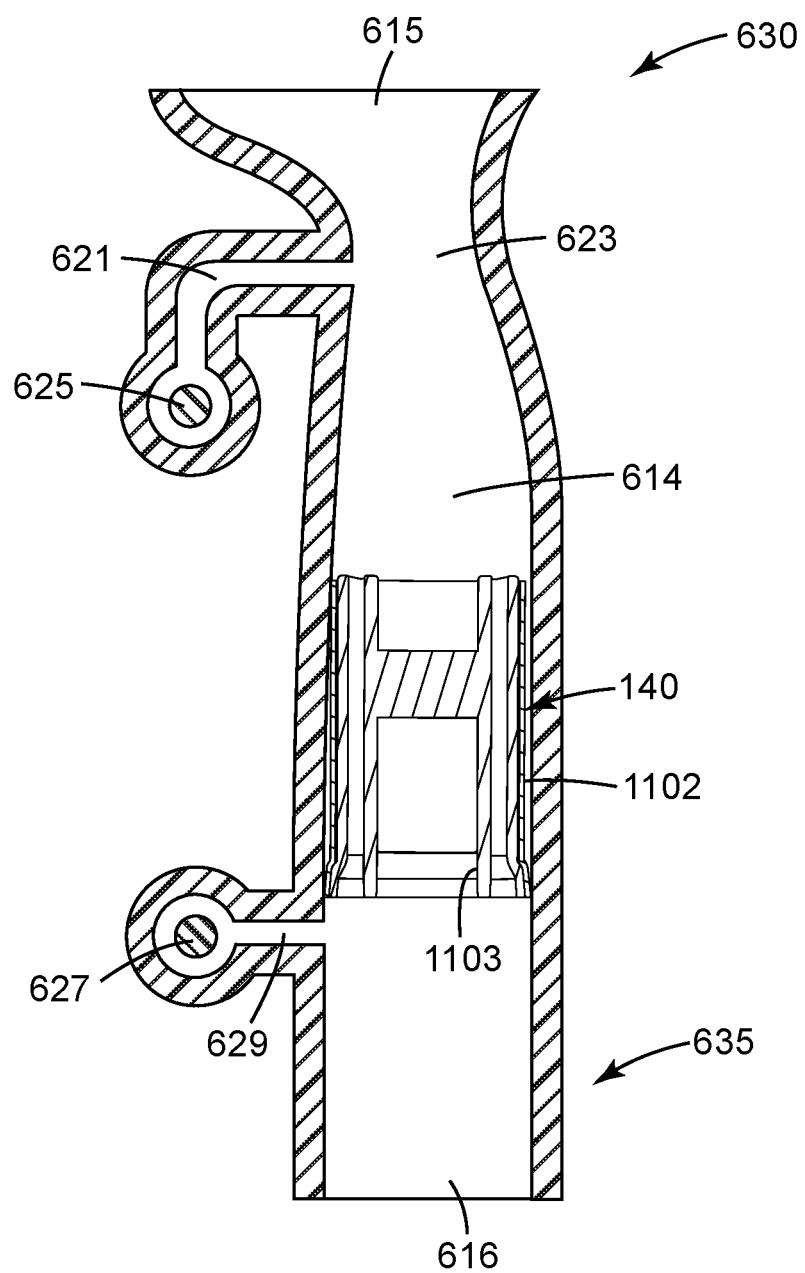
FIG. 35 is a front longitudinal cross-sectional view of a flow governor assembly of a medicinal inhaler according to one embodiment of the present disclosure, comprising the flow governor of FIGS. 22-27, an upstream venturi, and one or more pressure sensors positioned in fluid communication with the flow governor.

FIG. 35 illustrates a flow governor assembly (or "air flow path" or "air flow path assembly") 630 according to one embodiment of the present disclosure. The flow governor assembly 630 can be separately formed and put in fluid communication with or otherwise incorporated into an inhaler, or can form a portion of an inhaler of the present disclosure. As shown in FIG. 35, the flow governor assembly 630 can include a housing 635 that defines an air flow path 614 comprising an air inlet 615 and an air outlet 616; a flow governor 140 positioned in an air flow path 614; and a constriction 623 in the air flow path 614. The housing 635 is shown in greater detail in FIG. 36 and described in greater detail below.

The flow governor 140 can be configured to provide a variable (dynamic) resistance to air flow in an air flow path 614; and the constriction 623 can be configured to provide a fixed (static) resistance to air flow in the air flow path 614. The constriction 623 can include one or more of a venturi section (as shown), a narrow passageway (e.g., a narrow passageway, relative to adjacent regions/portions of the air flow path 614), a tortuous path, and a combination thereof. A tortuous path can include one or more twists, bends or turns (e.g., a sharp turn of at least 60 degrees).

In addition, in some embodiments, the flow governor assembly 630 can further include a first (air inlet) pressure sensor 625, and a second (air outlet) pressure sensor 627. The flow governor assembly 630 can be of dimensions (e.g., a length) appropriate to the physical dimensions of an associated inhaler.

In some embodiments, the housing 635 can be a separate element that can be positioned within, positioned in fluid communication with, and/or coupled to a housing of an inhaler. Additionally, or alternatively, in some embodiments, the housing 635 can refer to a portion of a housing of an inhaler, such that the housing 635 is integrally formed with a housing of an inhaler.

The air flow path 614, and particularly, the air inlet 615 can be shaped to improve the sensitivity of at least the first pressure sensor 625. The first pressure sensor 625 is connected to the air flow path 614 by a first conduit 621. The dimensions of this conduit (e.g., its cross-sectional area) can be chosen to ensure an appropriate balance between having a desirably low pressure drop along its length versus avoiding it being open enough to significantly affect the air flow in the main air flow path 614. In some embodiments, this conduit can be round in cross-section, with an internal diameter of approximately 2 mm and a total internal length of approximately 15 mm.

As mentioned above, the air flow path 614 can further include a fixed or static resistance, particularly, in the form of a constriction (or "venturi constriction") 623 located between the air inlet 615 and the air outlet 616 that particularly forms a venturi tube (or venturi section) that effectively amplifies the local air flow induced pressure drop at the first pressure sensor 625. Particularly, the constriction 623 can be located upstream of the flow governor 140. Such an amplification can enable the use of a less sensitive pressure sensor to measure the air flow rate with a given accuracy. This helps to constrain the manufacturing cost of the inhaler into which the assembly 630 is incorporated.

Addition of the second pressure sensor 627 connected by a second conduit 629 (e.g., in some embodiments, having an internal diameter of approximately 2 mm and an internal length of approximately 9 mm), to the air flow path 614 at a position downstream of, and away from, the venturi section constriction 623 can assist in determining the air flow direction (i.e., to distinguish inhalation from exhalation). This allows a linked breath-actuation triggering mechanism (e.g., mechanical or electronic) to be arranged not to operate if the patient breathes out into the inhaler, rather than in through it, the two breathing modes being easily differentiated by the different relative pressure drop relationships detected by the first and second sensors 625 and 627.

In some embodiments, the first conduit 621 can have a first cross-sectional area (e.g., an average cross-sectional area, or a cross-sectional area in a region of the first conduit located adjacent the first pressure sensor); the second conduit 629 can have a second cross-sectional area (e.g., an average cross-sectional area, or a cross-sectional area in a region of the first conduit located adjacent the first pressure sensor); and the air flow path 614 can have a third cross-sectional area (e.g., an average cross-sectional area, or a cross-sectional area in a region of the first conduit or the second conduit).

In some embodiments, the ratio of the first cross-sectional area to the third cross-sectional area and/or the ratio of the second cross-sectional area to the third cross-sectional area can be no greater than 0.3; in some embodiments, no greater than 0.25; in some embodiments, no greater than 0.2; in some embodiments, no greater than 0.18; in some embodiments, no greater than 0.16; in some embodiments, no greater than 0.15; in some embodiments, no greater than 0.1; in some embodiments, no greater than 0.08; in some embodiments, no greater than 0.07; and in some embodiments, no greater than 0.05.

The present inventors calculated that, in some embodiments, an inhaler comprising the flow governor assembly 630 of FIG. 35 can provide an overall resistance to air flow at 20 L/min. (below the collapse flow rate) of around 0.8 $Pa^{0.5}$ min./L. This is a desirable figure for an inhaler for the treatment of either COPD or asthma. Computational Fluid Dynamics (CFD) is a useful tool for use by one skilled in the art to develop appropriately modified and dimensioned alternative embodiments to those shown herein.

In some embodiments, where an inhaler incorporates one or more pressure sensors, the patient's inhalation profile can be recorded for each use of the inhaler. With inclusion of the appropriate electronic components, e.g. a memory device and data transmission means, each inhalation profile of the patient can be captured, stored and retrieved for future analysis and interpretation. This can allow the patient's physician and others to monitor the patient's ability to use the inhaler successfully and can allow appropriate and timely health care advice and/or interventions to be provided.

Furthermore, in some embodiments, air flow pressure drop measurements can be made to enable an inhaler to register both the fact that a dose was taken and to record the corresponding inhalation profile. This enables the patient's physician, or an authority or organization paying for the patient's health care provision, to know that the patient has actually taken the dose. Previous inhalers that have registered the release of a dose, even with a record of the date and time of that release, have not registered or recorded the corresponding inhalation profile, making them vulnerable to 'dose dumping', a practice in which patients can deceive their physicians and others into thinking that they are taking their prescribed doses even when in fact they are simply wasting them by spraying the doses into the surrounding air, etc. Such practices are well known as occurring where patients are embarrassed to tell their physician that they have not been following their prescribed treatment regime. The ability to detect such practices, via utilization of embodiments of the present disclosure, allows health care professionals the opportunity to understand what patients are actually doing, and allows them to advise and/or alter treatment regimes accordingly.

Figure 36:
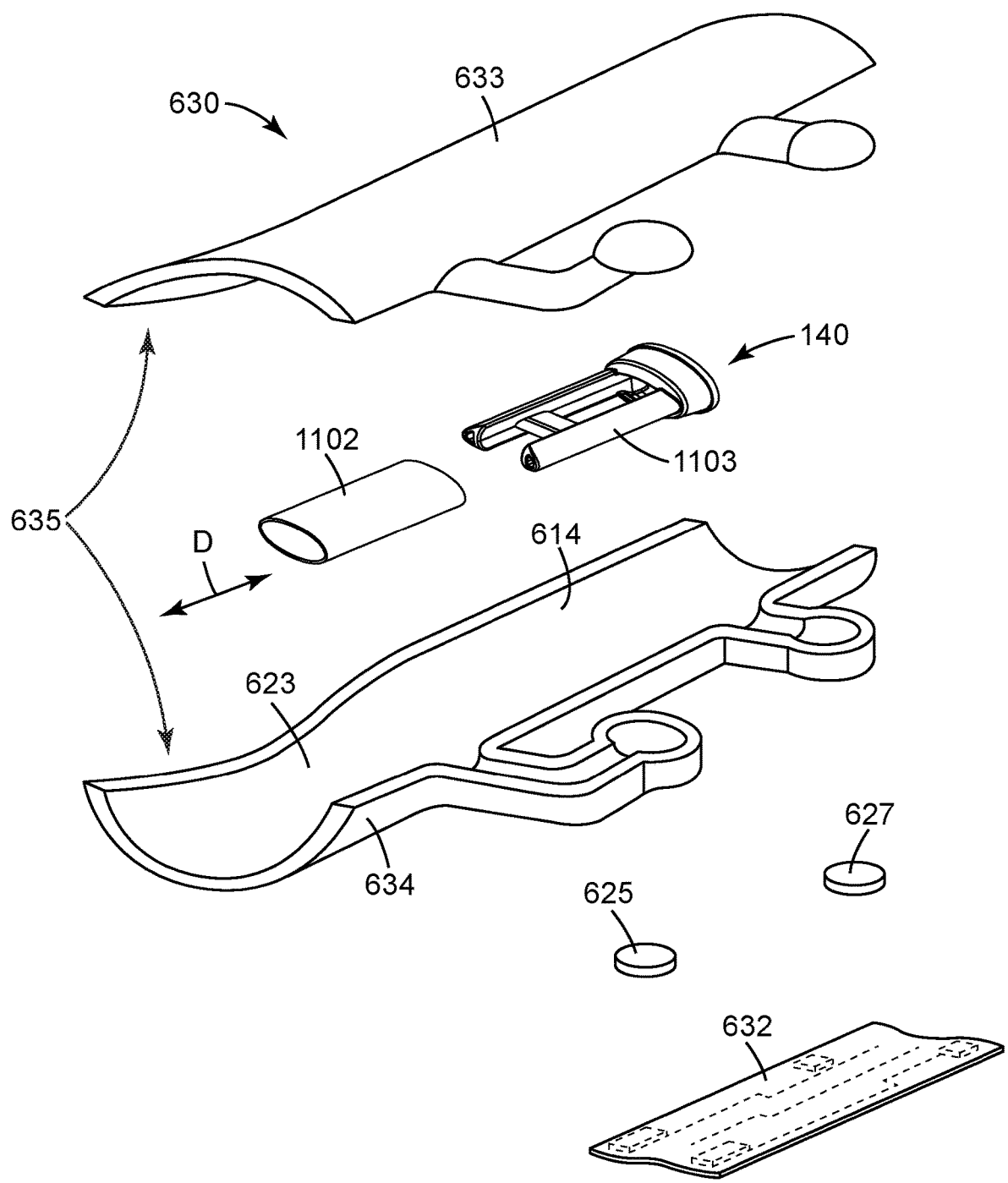
FIG. 36 is an exploded isometric view of the flow governor assembly of FIG. 35.

FIG. 36 illustrates one example of the elements or components that can be used to make the flow governor assembly 630 of FIG. 35. For example, in some embodiments, a controller 632 (e.g., a programmable circuit board (PCB)) can include the two pressure sensors 625, 627. As shown in FIGS. 35-36, the flow governor 140 comprises the tubular element 1102 and the internal support structure 1103. The air flow path 614 can be formed by a housing 635, which is shown as including a front housing 633 and a rear housing 634, e.g., for ease of plastic injection molding that can be coupled together (e.g., via any of the coupling means described above with respect to coupling the tubular element 1102 and the internal support structure 1103). In some embodiments, the housing 635 can be formed by two or more longitudinal portions (i.e., as shown in FIG. 36 by way of example), or additionally or alternatively, the housing 635 can be formed of two or more transverse portions that are joined transversely, relative to a longitudinal direction D, i.e., relative to the general air flow direction. The separate housing 635 is shown for simplicity and by way of example only; however, it should be understood that the assembly 630 and air flow path 614 can instead be formed (e.g., integrally formed) with a housing of a medicinal inhaler, and the inhaler can be modified to include all of the elements shown in FIGS. 35-36 of the assembly 630.

Various parameters affect the exact collapsing air flow rate and governing air flow rate for the flow governor 140 and the flow governor assembly 630. Examples of such parameters include the material forming the tubular element

1102; the diameter and thickness of the tubular element material; the shape and dimensions of the constriction 623 and of the internal support structure 1103; and environmental factors such as temperature and humidity (e.g., depending on the tubular element material). Based on the teachings of the present disclosure, a person of ordinary skill in the art will recognize how to test the effects of varying these different input parameters without departing from the spirit and scope of the present invention, in order to optimize an exact configuration of flow governor and air flow path for a particular application.

Figure 22:
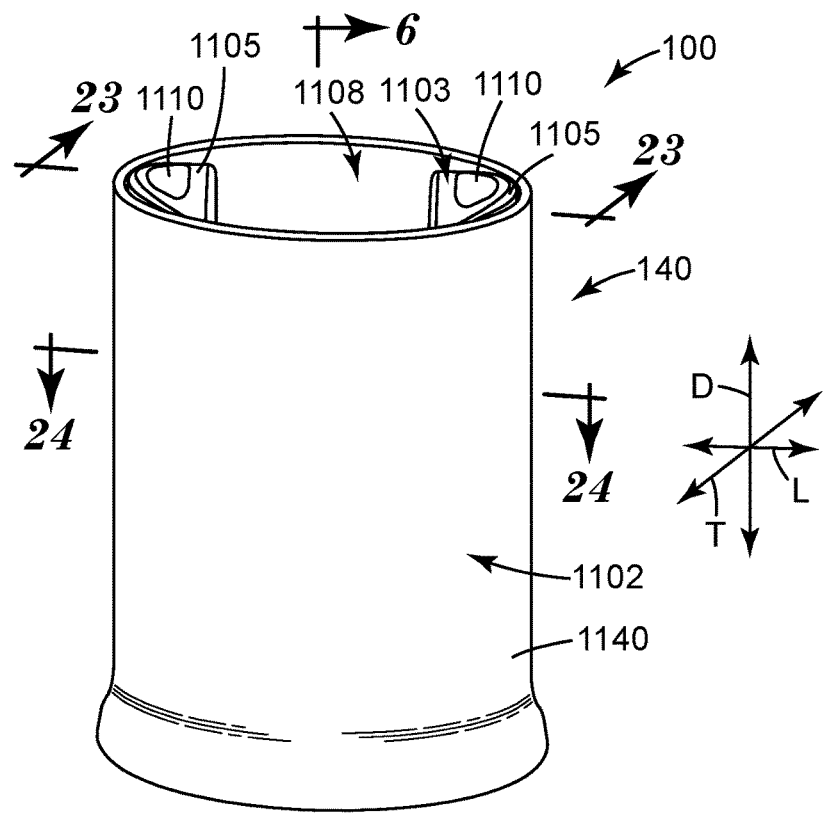
FIG. 22 is an isometric view of a flow governor according to one embodiment of the present disclosure, shown at rest.
Figure 37:
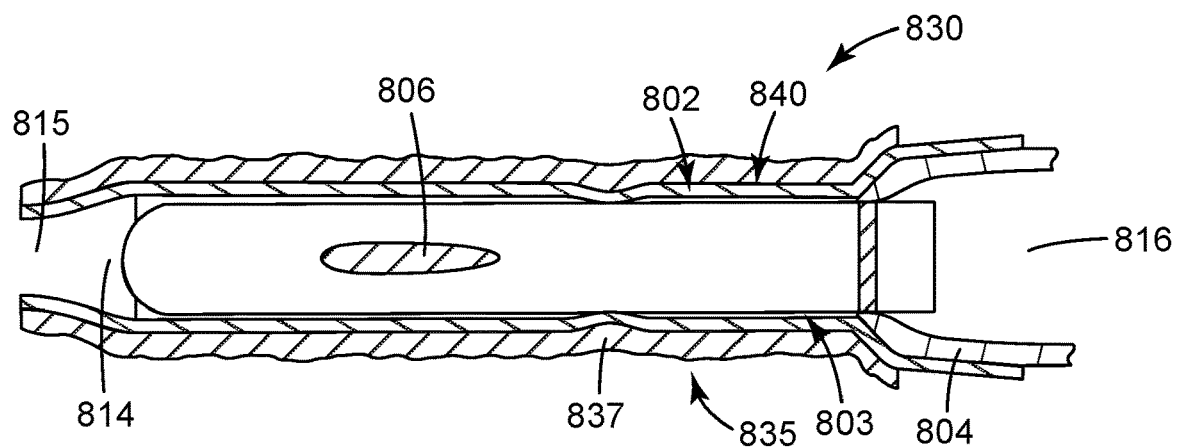
FIG. 37 is a side longitudinal cross-sectional view of a portion of a flow governor assembly of a medicinal inhaler according to another embodiment of the present disclosure, comprising a flow governor according to one embodiment of the present disclosure, shown at rest.

FIG. 37 illustrates a flow governor assembly 830 according to another embodiment of the present disclosure. The flow governor assembly 830 can be separately formed and put in fluid communication with or otherwise incorporated into an inhaler, or can form a portion of an inhaler of the present disclosure. As shown in FIG. 22, the flow governor assembly 830 can include a flow governor 840 positioned in an air flow path 814, the air flow path 814 including an air inlet 815 and an air outlet 816. The air flow path 814 can be formed by a housing 835. In some embodiments, the housing 835 can be a separate element that can be positioned within, positioned in fluid communication with, and/or coupled to a housing of an inhaler. Additionally, or alternatively, in some embodiments, the housing 835 can refer to a portion of a housing of an inhaler, such that the housing 835 is integrally formed with a housing of an inhaler.

The flow governor 840 includes a tubular element 802 and an internal support structure 803. As shown in FIG. 22 by way of example only, in some embodiments, the internal support structure 803 can include a hollow base 804 that can be at least partially formed by the housing 835, or a portion thereof, such that the tubular element 802 is stretched externally around one portion (e.g., an outer wall) of the housing 835 and is located internally with respect to another portion of the housing 835. In such embodiments, the entire internal support structure 803 can be integrally formed, or provided by, a portion of the housing 835, which, as described above, can also form at least a portion of an inhaler.

As further shown in FIG. 37, the air flow path 814 can include (e.g., the housing 835 can include) one or more inwardly-projecting protrusions or features 837 positioned at one or more desired longitudinal positions to encourage the tubular element 802 of the flow governor 840 to collapse at specific, pre-defined locations. In some embodiments, the one or inwardly-projecting protrusions 837 can be in the form of pinching splines, or in some embodiments, the protrusion(s) 837 can include an annular protrusion surrounding the tubular element 802. The protrusions(s) 837 can apply mechanical stress to the tubular element 802. By altering the size and/or number of the protrusion(s) 837, the flow rate at which the tubular element 802 collapses can be controlled. Additionally, or alternatively, in some embodiments, the tubular element material properties can be controlled to encourage precise collapse geometry and characteristics, e.g., by employing a particular Shore hardness at a specific section of the tubular element 802.

The protrusion(s) 837 can also reduce any tendency of the inwardly flexing regions of the tubular element 802 to stick to the housing 835, e.g. if the patient exhales moisture into the inhaler.

Furthermore, in some embodiments, the air flow path 814 can include a constriction, and particularly, a constriction located upstream of the flow governor 840, i.e., toward the air inlet 815, used as a venturi section to accelerate the local air velocity past an adjacent pressure sensor (not shown), as described above with respect to FIGS. 35 and 36. Such an arrangement can allow for more precise pressure measurements (and calculated air flow rate measurements) than would otherwise be achieved from a given pressure sensor.

Figure 38:
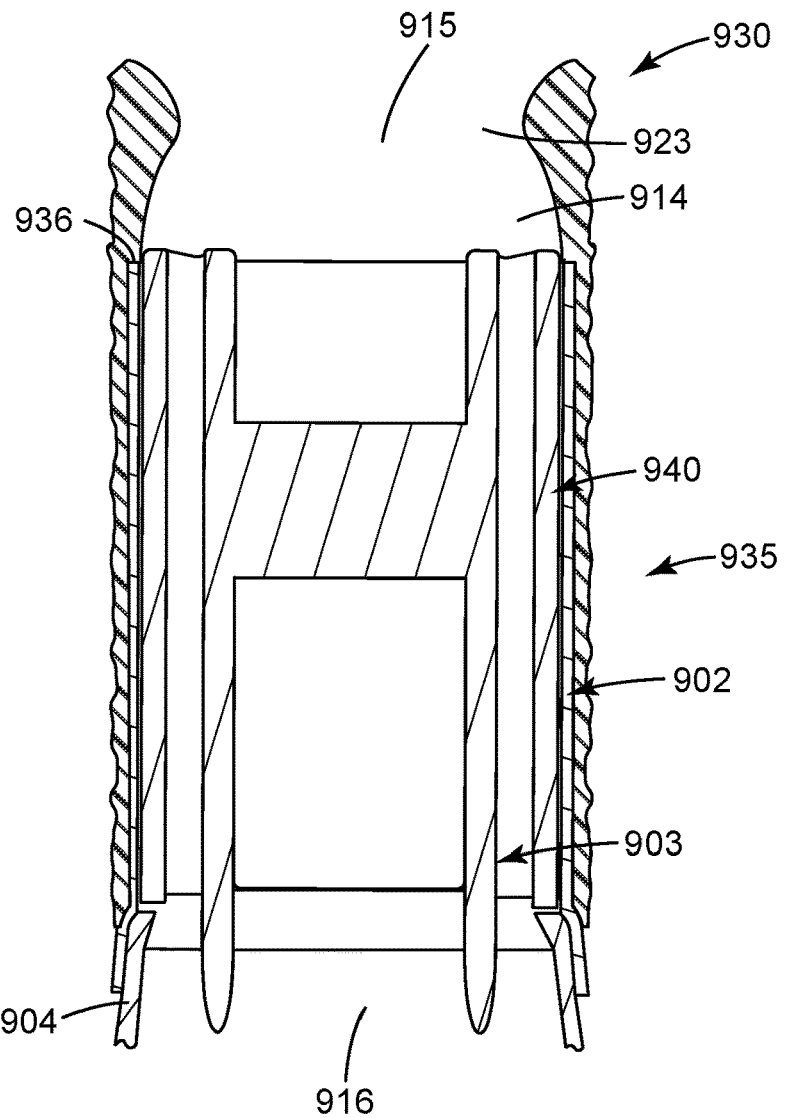
FIG. 38 is a front longitudinal cross-sectional view of a portion of a flow governor assembly of a medicinal inhaler according to another embodiment of the present disclosure, comprising a flow governor according to one embodiment of the present disclosure, shown at rest.

FIG. 38 illustrates a flow governor assembly 930 according to another embodiment of the present disclosure. The flow governor assembly 930 can be separately formed and put in fluid communication with or otherwise incorporated into an inhaler, or can form a portion of an inhaler of the present disclosure. As shown in FIG. 38, the flow governor assembly 930 can include a flow governor 940 positioned in an air flow path 914, the air flow path 914 including an air inlet 915 and an air outlet 916. The air flow path 914 can be formed by a housing 935. In some embodiments, the housing 935 can be a separate element that can be positioned within, positioned in fluid communication with, and/or coupled to a housing of an inhaler. Additionally, or alternatively, in some embodiments, the housing 935 can refer to a portion of a housing of an inhaler, such that the housing 935 is integrally formed with a housing of an inhaler.

The flow governor 940 includes a tubular element 902 and an internal support structure 903. As shown in FIG. 38 by way of example only, in some embodiments, the internal support structure 903 can include a hollow base 904 that can be at least partially formed by the housing 935, or a portion thereof, such that the tubular element 902 is stretched externally around one portion of the housing 935 and is located internally with respect to another portion of the housing 935. As shown, in some embodiments, the air flow path 914 can include a venturi constriction 923 upstream of the flow governor 940, which can be used to enhance the sensitivity of an adjacent pressure sensor (not shown) as has already been described.

In some embodiments, as shown in FIG. 38, the air flow path 914 can include one or more features that can be directly formed in the housing 935 into which the flow governor 940 sits to direct the flowing air into the flow governor 940. For example, as shown in FIG. 38, the air flow path 914 can include a channeling step 936 that directs the air flow into the flow governor 940 and prevents air flow to an outer, external, side of the tubular element 902, thus preventing pressure drop loss and keeping the air on the outer surface of the tubular element 902 stagnant.

Each embodiment shown in the figures is illustrated as a separate embodiment for clarity in illustrating a variety of features of the flow governors and medicinal inhalers of the present disclosure. However, it should be understood that any combination of elements and features of any of the embodiments illustrated in the figures and described herein can be employed in the flow governors and medicinal inhalers of the present disclosure. For example, any of the firing systems of FIGS. 1-15, 16, 17, 18, 19 and 20 can be employed in any medicinal inhaler of the present disclosure. In addition, any of the features of the flow governor assemblies of FIG. 35-38, or combinations thereof, or partial combinations thereof, can be incorporated into any of the medicinal inhalers of FIGS. 1, 16-20 and 34. Furthermore, any of the flow governor features of FIG. 22-33, or combinations thereof, or partial combinations thereof, can be incorporated into any of the flow governor assemblies or medicinal inhalers of the present disclosure.

The following embodiments are intended to be illustrative of the present disclosure and not limiting.

EMBODIMENTS

Medicinal Inhaler Embodiments

1. A medicinal inhaler comprising:
a housing;
an air flow path defined by at least partially the housing and including an air inlet and an air outlet;
a flow governor positioned in the air flow path (i.e., positioned in the housing) between the air inlet and the air outlet to govern air flow (e.g., substantially all of the air flow) in the air flow path to a governing volumetric flow rate (e.g., the flow governor configured to provide a variable resistance to air flow in the air flow path as a function of air pressure drop between an inlet and an outlet of the flow governor); and
a breath-actuated dose release firing system located in the housing, wherein the firing system is configured to release a dose of medicament at a firing volumetric flow rate less than the governing volumetric flow rate.

2. The inhaler of embodiment 1, wherein the medicinal inhaler includes a pressurized metered dose inhaler (pMDI).

3. The inhaler of embodiment 1 or 2, wherein the firing system is mechanically triggered.

4. The inhaler of any of embodiments 1-3, wherein the firing system is electronically triggered.

5. The inhaler of any of embodiments 1-4, wherein the firing system includes a plunger movable between a first position and a second position to actuate a dose release valve.

6. The inhaler of embodiment 5, wherein the plunger is configured to be operatively coupled to a medicament canister comprising the dose release valve.

7. The inhaler of embodiment 5 or 6, wherein the firing system further includes a stored energy device configured to drive the plunger from the first position to the second position when stored energy in the stored energy device is released.

8. The inhaler of any of embodiments 5-7, wherein the stored energy device includes a biasing element.

9. The inhaler of any of embodiments 5-8, wherein the stored energy is triggered to release by a trigger connected to an inspiratory air flow detection system, the inspiratory air flow detection system configured to detect an inspiratory air flow rate in the air flow path and to send an electrical signal to the trigger when the inspiratory air flow rate is equal to at least the firing volumetric flow rate.

10. The inhaler of any of embodiments 5-9, wherein the firing system further includes:
a guideway, wherein at least a portion of the guideway has a helical shape, the guideway having a first portion having a first helix angle with respect to the axis that is greater than zero, and a second portion having a second helix angle with respect to the axis, wherein the second helix angle is less than the first helix angle; and
a projection dimensioned to be received in the guideway, the projection being movable in the guideway, such that the projection and the guideway are movable with respect to one another between a first position corresponding to the first position of the plunger and a second position corresponding to the second position of the plunger, such that the projection is configured to be cammed along the guideway when the stored energy device drives the plunger to move between the first position and the second position;
wherein the guideway or the projection is fixedly coupled to the plunger.

11. The inhaler of any of embodiments 1-10, further comprising an inspiratory air flow detection system configured to detect an inspiratory air flow rate in the air flow path and to send an electrical signal to the firing system to fire when the inspiratory air flow rate is equal to at least the firing volumetric flow rate.

12. The inhaler of embodiment 11, wherein the inspiratory air flow detection system includes at least one pressure sensor located in the air flow path, and a controller connected to the at least one pressure sensor and the breath-actuated dose release firing system.

13. The inhaler of any of embodiments 1-12, further comprising a pressure sensor located in the air flow path upstream of the flow governor.

14. The inhaler of any of embodiments 1-13, further comprising a first pressure sensor located in the air flow path upstream of the flow governor and a second pressure sensor located in the air flow path downstream of the flow governor.

15. The inhaler of any of embodiments 1-14, further comprising a first pressure sensor located in a first conduit connected to the air flow path at a first location upstream of the flow governor and a second pressure sensor located in a second conduit connected to the air flow path at a second location downstream of the flow governor.

16. The inhaler of embodiment 15, wherein the first conduit has a first cross-sectional area, the second conduit has a second cross-sectional area, and the air flow path has a third cross-sectional area, and wherein the ratio of the first cross-sectional area to the third cross-sectional area and the ratio of the second cross-sectional area to the third cross-sectional area are each no greater than 0.2.

17. The inhaler of any of embodiments 1-16, wherein the flow governor includes:
a tubular element that defines at least a portion of an air flow path, the tubular element comprising at least one flexible wall configured to flex inwardly in response to an air flow in the air flow path; and
an internal support structure, located within the tubular element and configured to preserve at least a predetermined cross-sectional area of the air flow path within the tubular element when the at least one flexible wall of the tubular element flexes inwardly.

18. The inhaler of embodiment 17, wherein at least a portion of the internal support structure is formed by the housing.

19. The inhaler of embodiment 17 or 18, wherein the internal support structure is rigid relative to the tubular element, and the tubular element is flexible relative to the internal support structure.

20. The inhaler of any of embodiments 17-19, wherein the tubular element is substantially bistable between an uncollapsed state and a collapsed state.

21. The inhaler of any of embodiments 1-20, wherein the inhaler includes at least two flow governors positioned in the air flow path.

22. The inhaler of embodiment 21, wherein the at least two flow governors are arranged in parallel.

23. The inhaler of embodiment 21, wherein the at least two flow governors are arranged in series.

24. The inhaler of any of embodiments 1-23, wherein the governing volumetric flow rate is at least about 25 L/min.

25. The inhaler of any of embodiments 1-24, wherein the governing volumetric flow rate is no greater than about 35 L/min.

26. The inhaler of any of embodiments 1-25, wherein the air inlet of the air flow path includes an aspiration orifice of the medicinal inhaler, and wherein the air outlet of the air flow path includes an inhalation orifice of the medicinal inhaler.

Firing System Embodiments

1. A dose release firing system for use in a medicinal inhaler, the dose release firing system comprising:
an axis that defines an axial direction that extends along or substantially parallel to the axis;
a plunger movable in the axial direction between a first position and a second position;
a stored energy device configured to drive the plunger from the first position to the second position when stored energy in the stored energy device is released, wherein the firing system is in a primed state when the stored energy is not released, and wherein the firing system is in a fired state when the stored energy is released (i.e., after the stored energy has been released);
a guideway, wherein at least a portion of the guideway has a helical shape, the guideway having a first portion having a first helix angle with respect to the axis that is greater than zero, and a second portion having a second helix angle with respect to the axis, wherein the second helix angle is less than the first helix angle; and
a projection dimensioned to be received in the guideway, the projection being movable in the guideway, such that the projection and the guideway are movable with respect to one another between a first position corresponding to the first position of the plunger and a second position corresponding to the second position of the plunger, such that the projection is configured to be cammed along the guideway when the stored energy device drives the plunger to move from the first position to the second position;
wherein the guideway or the projection is fixedly coupled to the plunger.

2. The firing system of embodiment 1, wherein the stored energy device, the guideway and the projection are positioned such that the guideway and the projection move relative to one another in response to stored energy being released from the stored energy device.

3. The firing system of embodiment 1 or 2, wherein the first helix angle is at least 45 degrees.

4. The firing system of any of embodiments 1-3, wherein the second helix angle is less than 20 degrees.

5. The firing system of any of embodiments 1-4, wherein the first portion of the guideway is helical with respect to the axis and the second portion of the guideway is aligned with or substantially parallel to the axis.

6. The firing system of any of embodiments 1-5, wherein the stored energy device is configured to provide at least 40 N of force when the stored energy is released.

7. The firing system of any of embodiments 1-6, wherein:
the medicinal inhaler includes a medicament canister,
the axis is a longitudinal axis configured to be aligned with or parallel to a longitudinal axis of the medicament canister,
the plunger is configured to be operatively coupled to the medicament canister, and
the plunger is configured to move between the first position and the second position to actuate a dose release valve of the medicament canister.

8. The firing system of any of embodiments 1-7, wherein the plunger includes a recess dimensioned to receive at least a portion of a medicament canister.

9. The firing system of any of embodiments 1-8, wherein the plunger is rotationally fixed with respect to the axis.

10. The firing system of any of embodiments 1-9, wherein the guideway and the projection are rotatable with respect to one another about the axis.

11. The firing system of any of embodiments 1-10, wherein:
the guideway and the projection are rotatable with respect to one another about the axis, and
the plunger is rotationally fixed with respect to the axis.

12. The firing system of any of embodiments 1-11, wherein the guideway is rotatable about the axis with respect to the projection, wherein the projection is fixedly coupled to the plunger, and wherein the projection and the plunger are rotationally fixed with respect to the axis.

13. The firing system of any of embodiments 1-12, wherein the guideway is provided by a shaft having a shaft axis oriented along or parallel to the axis and comprising a wall, and wherein the guideway is formed in the wall of the shaft.

14. The firing system of embodiment 13, wherein the shaft is dimensioned to be received in a recess of the plunger.

15. The firing system of embodiment 13 or 14, wherein the shaft is rotatable about the axis.

16. The firing system of any of embodiments 1-15, wherein the guideway is provided by a rotary arm module, the rotary arm module comprising:
a shaft having a shaft axis oriented in the axial direction and comprising a wall, wherein the guideway is formed in the wall, the shaft including a flanged end, and
an arm extending radially outwardly from the flanged end of the shaft.

17. The firing system of embodiment 16, wherein the shaft is dimensioned to be received in a recess of the plunger.

18. The firing system of embodiment 16 or 17, wherein the rotary arm module is rotatable about the axis.

19. The firing system of any of embodiments 13-18, wherein the projection is provided by a firing pin, wherein the shaft is hollow and defines a tubular channel dimensioned to receive the firing pin, and wherein the projection extends radially outwardly from the firing pin to be received in the guideway of the shaft.

20. The firing system of embodiment 19, wherein the firing pin and the plunger are fixedly coupled together.

21. The firing system of embodiment 19 or 20, wherein the firing pin and the plunger include inter-engaging features to fixedly couple the firing pin and the projection to the plunger.

22. The firing system of any of embodiments 19-21, wherein the projection protrudes from a flat recessed area on an outer surface of the firing pin.

23. The firing system of any of embodiments 19-22, wherein the projection of the firing pin is one of two diametrically opposed radial projections, and wherein the guideway is one of two diametrically opposed guideways formed in the wall of the shaft.

24. The firing system of any of embodiments 19-23, wherein the guideway is configured to cause the firing pin and the plunger to move axially in response to release of the stored energy of the stored energy device.

25. The firing system of any of embodiments 13-24, wherein the stored energy device is located between an outer surface of the shaft and an inner surface of a recess of the plunger.

26. The firing system of embodiment 25, wherein the recess of the plunger is tubular in shape and dimensioned to receive the shaft.

27. The firing system of any of embodiments 16-26, wherein the shaft is hollow and defines a tubular channel, wherein the flanged end of the shaft includes an annular cylindrical flange that includes an orifice generally aligned with the tubular channel of the shaft.

28. The firing system of embodiment 27, wherein the annular cylindrical flange is dimensioned to provide a contact surface for the stored energy device.

29. The firing system of any of embodiments 1-28, further comprising a latch movable between (i) a first position in which the latch is coupled to at least one of the guideway and the projection to inhibit the guideway and the projection from moving relative to one another, and (ii) a second position in which the latch is decoupled from the guideway and the projection, such that the guideway and the projection are free to move relative to one another.

30. The firing system of embodiment 29, wherein the stored energy of the stored energy device is released in response to the latch being moved from its first position to its second position.

31. The firing system of embodiment 29 or 30, further comprising a trigger operatively coupled to the latch and configured to change between a first state and a second state to move the latch between the first position and the second position, respectively.

32. The firing system of embodiment 31, wherein the latch is pivotally movable about a latch axis between the first position and the second position, and wherein the trigger is configured to pivot the latch about the latch axis between the first position and the second position.

33. The firing system of embodiment 32, wherein the latch axis is oriented substantially orthogonally with respect to the axis.

34. The firing system of any of embodiments 31-33, wherein the trigger comprises a shape memory material.

35. The firing system of any of embodiments 31-34, wherein the trigger comprises a digital motor, a spool, and a filament.

36. The firing system of any of embodiments 31-35, wherein the trigger comprises an electromagnet.

37. The firing system of any of embodiments 31-36, wherein the trigger comprises a solenoid.

38. The firing system of any of embodiments 31-37, wherein the trigger comprises a mechanical actuator.

39. The firing system of any of embodiments 31-38, wherein the trigger is configured to change between the first state and the second state in response to non-mechanical energy.

40. The firing system of any of embodiments 31-38, wherein the trigger is configured to change between the first state and the second state in response to mechanical energy.

41. The firing system of any of embodiments 31-40, wherein the trigger is breath-actuated.

42. The firing system of any of embodiments 1-41, wherein the stored energy device includes a spring.

43. The firing system of any of embodiments 1-42, wherein the firing system is breath-actuated.

44. A medicinal inhaler comprising the dose release firing system of any of the preceding embodiments (e.g., positioned in a housing), wherein the medicinal inhaler is a pressurized metered dose inhaler (pMDI).

45. A medicinal inhaler comprising the dose release firing system of any of the preceding embodiments (e.g., positioned in a housing), wherein the medicinal inhaler is at least one of a breath-actuated inhaler, a pressurized metered dose inhaler (pMDI), a dry powder inhaler (DPI), a nebulizer, and a combination thereof.

46. A medicinal inhaler comprising:
a housing;
a canister comprising a medicament positioned in the housing; and
the dose release firing system of any of the preceding embodiments positioned in the housing, with the plunger operatively coupled to the canister.

47. The inhaler of embodiment 46, wherein the plunger is rotationally fixed with respect to the axis and the housing.

48. The inhaler of embodiment 46 or 47, wherein the plunger and the housing include inter-engaging features to inhibit relative rotational movement between the plunger and the housing.

49. A dose release firing system for use in a medicinal inhaler that comprises a medicament canister, the dose release firing system comprising:
a longitudinal axis configured to be aligned with or parallel to a longitudinal axis of the medicament canister;
a plunger configured to be operatively coupled to the medicament canister, the plunger movable along the longitudinal axis between a first position and a second position, wherein the plunger is configured to move the medicament canister between a first position in which a medicament dose is not released and a second position in which a medicament dose is released, respectively;
a stored energy device configured to drive the plunger to the second position when stored energy in the stored energy device is released, wherein the firing system is in a primed state when the stored energy is not released, and wherein the firing system is in a fired state when the stored energy is released;
a rotary arm module, the rotary arm module comprising:
a shaft having a shaft axis oriented along the longitudinal axis and comprising a wall, the shaft being hollow and defining a tubular channel, the shaft dimensioned to be received in a recess of the plunger, the shaft including a flanged end,
an arm extending radially outwardly from the flanged end of the shaft, and
a guideway formed in the wall of the shaft, wherein at least a portion of the guideway has a helical shape, the guideway having a first portion having a first helix angle with respect to the axis that is greater than zero, and a second portion having a second helix angle with respect to the axis, wherein the second helix angle is less than the first helix angle; and
a firing pin dimensioned to be received in the tubular channel of the shaft of the rotary arm module, the firing pin being fixedly coupled to the plunger and including a projection that is dimensioned to be received in the guideway, the projection being movable in the guideway between a first position corresponding to the first position of the plunger and a second position corresponding to the second position of the plunger, such that the projection is configured to cam along the guideway when driven by the stored energy device to cause the plunger to move between the first position and the second position.

50. The firing system of embodiment 49, wherein the rotary arm module is rotatable about the longitudinal axis.

51. The firing system of embodiment 49 and 50, wherein the plunger and the firing pin are rotationally fixed with respect to the longitudinal axis.

52. The firing system of any of embodiments 49-51, further comprising a latch movable between (i) a first position in which the latch is coupled to the arm of the rotary arm module and (ii) a second position in which the latch is decoupled from the arm.

Flow Governor Embodiments

1. A flow governor for use in a medicinal inhaler, the flow governor comprising:
a tubular element that defines at least a portion of an air flow path, the tubular element comprising at least one flexible wall configured to flex inwardly in response to an air flow in the air flow path; and
an internal support structure, located within the tubular element and configured to preserve at least a predetermined cross-sectional area of the air flow path within the tubular element when the at least one flexible wall of the tubular element flexes inwardly.

2. The flow governor of embodiment 1, wherein the flow governor is substantially linear.

3. The flow governor of embodiment 1 or 2, wherein the tubular element is substantially bistable between an uncollapsed state and a collapsed state.

4. The flow governor of any of embodiments 1-3, wherein the internal support structure is rigid relative to the tubular element, and the tubular element is flexible relative to the internal support structure.

5. The flow governor of any of embodiments 1-4, further comprising a longitudinal direction, wherein the at least one flexible wall of the tubular element is oriented substantially parallel to the longitudinal direction.

6. The flow governor of embodiment 5, wherein the tubular element is elongated along in the longitudinal direction.

7. The flow governor of any of embodiments 1-6, further comprising:
an air inlet located at a first end of the tubular element; and
an air outlet located at a second end, opposite the first end, of the tubular element.

8. The flow governor of any of embodiments 1-7, wherein the flow governor has an elliptical transverse cross-sectional shape.

9. The flow governor of any of embodiments 1-8, wherein the tubular element has an elliptical transverse cross-sectional shape.

10. The flow governor of any of embodiments 1-9, wherein the internal support structure has a base having an outer wall, and wherein an end of the tubular element is stretched over the outer wall of the base of the internal support structure.

11. The flow governor of embodiment 10, wherein the outer wall of the base of the internal support structure has an elliptical transverse cross-sectional shape.

12. The flow governor of embodiment 10 or 11, wherein the outer wall of the base of the internal support structure has a circular transverse cross-sectional shape.

13. The flow governor of any of embodiments 1-12, wherein the internal support structure includes at least one hollow pillar, and wherein the air flow path through the flow governor includes a space between an outer wall of the internal support structure and the tubular element, and a space within the at least one hollow pillar.

14. The flow governor of any of embodiments 1-13, wherein the internal support structure has a generally H-shaped transverse cross-sectional shape.

15. The flow governor of any of embodiments 1-14, wherein the internal support structure has a generally H-shaped longitudinal cross-sectional shape.

16. The flow governor of any of embodiments 1-15, wherein the internal support structure includes a transverse cross-sectional shape comprising at least one capital English letter "E".

17. The flow governor of any of embodiments 1-16, wherein the internal support structure includes a transverse cross-sectional shape comprising at least one of the capital English letters selected from B, C, D, E, H, M, N, O, S, V, W, X and Z.

18. The flow governor of any of embodiments 1-17, wherein the internal support structure includes at least one pillar oriented substantially along a longitudinal direction of the tubular element and protruding from an inlet end of the tubular element.

19. The flow governor of any of embodiments 1-18, wherein the internal support structure includes at least one hollow pillar defining a lumen therein.

20. The flow governor of any of embodiments 1-19, wherein the internal support structure includes at least one solid pillar.

21. The flow governor of any of embodiments 1-20, wherein the internal support structure includes two pillars oriented substantially parallel to a longitudinal direction of the tubular element, and a cross member positioned to couple the two pillars, the cross member oriented at a non-zero angle with respect to the longitudinal direction.

22. The flow governor of any of embodiments 1-21, wherein the internal support structure includes two hollow pillars oriented substantially parallel to a longitudinal direction of the tubular element, each pillar defining a lumen therein, and a solid cross member positioned to couple the two hollow pillars, the cross member oriented at a non-zero angle with respect to the longitudinal direction.

23. The flow governor of any of embodiments 1-21, wherein the internal support structure includes two solid pillars oriented substantially parallel to a longitudinal direction of the tubular element, and a solid cross member positioned to couple the two solid pillars, the cross member oriented at a non-zero angle with respect to the longitudinal direction.

24. The flow governor of any of embodiments 21, 22 and 23, wherein the internal support structure includes at least one transverse protrusion extending from the cross member.

25. The flow governor of any of embodiments 21-24, wherein the cross member is oriented substantially perpendicularly with respect to the longitudinal direction.

26. The flow governor of any of embodiments 1-25, wherein the internal support structure includes at least one rib that protrudes substantially orthogonally with respect to the at least one flexible wall of the tubular element.

27. A medicinal inhaler comprising at least one flow governor of any of the preceding embodiments positioned in fluid communication with an air flow path of the medicinal inhaler.

28. The medicinal inhaler of embodiment 27, wherein the medicinal inhaler includes at least two flow governors arranged in parallel.

29. The medicinal inhaler of embodiment 27 or 28, wherein the medicinal inhaler includes at least two flow governors arranged in series.

30. A medicinal inhaler comprising:
a housing comprising
a tubular sleeve portion dimensioned to receive a canister comprising a medicament, and
a patient port;
an air flow path including an air inlet and an air outlet, wherein the air outlet is defined by the patient port; and the flow governor of any of embodiments 1-26 positioned in the air flow path.

31. The medicinal inhaler of any of embodiments 27-30, wherein the medicinal inhaler is a pressurized metered dose inhaler (pMDI).

32. The medicinal inhaler of any of embodiments 27-30, wherein the medicinal inhaler is at least one of a breath-actuated inhaler, a pressurized metered dose inhaler (pMDI), a dry powder inhaler (DPI), a nebulizer, and a combination thereof.

33. The medicinal inhaler of any of embodiments 30-32, wherein the tubular sleeve portion of the housing includes a first open end, and wherein the housing further includes a second open end dimensioned to receive the flow governor.

34. The medicinal inhaler of embodiment 33, wherein the housing further includes a cover or a seal positioned to seal the first open end from ambience.

35. The medicinal inhaler of any of embodiments 27-34, wherein the flow governor is positioned in a dedicated air flow path, wherein the dedicated air flow path includes an air inlet open to ambience and an air outlet in fluid communication with the air flow path of the inhaler, and wherein the flow governor is positioned between the air inlet and the air outlet of the dedicated air flow path.

36. The medicinal inhaler of embodiment 35, wherein the dedicated air flow path is integrally formed with the housing.

37. The medicinal inhaler of embodiment 35, or 36, wherein the dedicated air flow path is formed in a rear portion of the housing, opposite the patient port.

38. The medicinal inhaler of embodiment 35 or 36, wherein the dedicated air flow path is formed in a bottom portion of the housing.

39. The medicinal inhaler of embodiment 38, wherein the air inlet of the dedicated air flow path is located below the patient port.

40. The medicinal inhaler of any of embodiments 30-39, further comprising a cover positioned over the tubular sleeve portion of the housing to seal the open end from ambience, such that any air taken into the inhaler is moved through the flow governor.

41. The medicinal inhaler of any of embodiments 30-40, further comprising a skirt seal located between an outer surface of the canister and an inner surface of the housing.

42. The medicinal inhaler of any of embodiments 30-41, further comprising a cap configured to be coupled to the tubular sleeve portion of the housing to seal the tubular sleeve portion, the cap defining the air inlet and including the flow governor.

43. The medicinal inhaler of any of embodiments 27-42, further comprising a pressure sensor located in the air flow path upstream of the flow governor.

44. The medicinal inhaler of any of embodiments 27-43, further comprising a first pressure sensor located in the air flow path upstream of the flow governor and a second pressure sensor located in the air flow path downstream of the flow governor.

45. A flow governor assembly for use in a medicinal inhaler, the flow governor assembly comprising:
 a housing;
 an air flow path defined by the housing and including an air inlet and an air outlet; and
 the flow governor of any of embodiments 1-26, the flow governor being positioned in the air flow path between the air inlet and the air outlet.

46. The flow governor assembly of embodiment 45, further comprising a first pressure sensor positioned in fluid communication with the air flow path upstream of the flow governor and a second pressure sensor positioned in fluid communication with the air flow path downstream of the flow governor.

47. The flow governor assembly of embodiment 45 or 46, further comprising a first pressure sensor located in a first conduit connected to the air flow path upstream of the flow governor and a second pressure sensor located in a second conduit connected to the air flow path downstream of the flow governor.

48. The air flow path of embodiment 47, further comprising a constriction located in the air flow path adjacent where the first conduit connects to the air flow path.

49. The air flow path of any of embodiments 45-48, further comprising a constriction located between the air inlet and the flow governor.

50. A method of using a medicinal inhaler, the method comprising:
 providing a medicinal inhaler comprising a flow governor according to any of embodiments 1-26; and
 varying an air flow resistance of the inhaler in response to air flow in the air flow path of the flow governor.

51. The method of embodiment 50, further comprising inserting a patient port of the medicinal inhaler into a body cavity of a patient; and inhaling through the patient port to cause air flow in the air flow path of the flow governor.

52. The method of embodiment 50 or 51, wherein varying the air flow resistance of the inhaler includes flexing the at least one tubular wall inwardly toward the internal support structure.

Some embodiments of the present disclosure provide a medicinal inhaler comprising a triggering system for the mechanical actuation of an aerosol dose dispenser,
 the triggering system being operable to release a supply of stored energy to operate the aerosol dose dispenser to dispense a dose of aerosolised medicament; and
 the medicinal inhaler comprising a system to generate an electrical impulse signal in response to a detected inspiratory air flow through the inhaler; wherein
 the triggering system comprises a Shape Memory Alloy wire that is heated by said electrical impulse signal, the heating causing the wire to shorten and thereby to pull on a movable trigger, movement of the trigger causing movement and release of a latch retaining the supply of stored energy.

Some embodiments of the present disclosure provide a medicinal inhaler comprising a triggering system for the mechanical actuation of an aerosol dose dispenser,
 the medicinal inhaler comprising an inspiratory air flow detection system, an electrical signal generation system and a flow governor,
 the electrical signal generation system generating an electrical impulse signal in response to a detected inspiratory air flow through the inhaler;
 wherein the triggering system is operable to release a supply of stored energy to operate the aerosol dose dispenser to dispense a dose of aerosolised medicament, the triggering system comprising a Shape Memory Alloy wire that is heated by said electrical signal, the heating causing the wire to shorten and thereby to pull on a movable trigger, movement of the trigger causing movement and release of a latch retaining the supply of stored energy.

It is to be understood that the invention is not limited in its application to the details of construction and the arrangement of components set forth in the above description or illustrated in the accompanying drawings. The invention is capable of other embodiments and of being practiced or of being carried out in various ways. Also, it is to be understood that the phraseology and terminology used herein is for the purpose of description and should not be regarded as limiting. It is to be further understood that other embodiments may be utilized, and structural or logical changes may be made without departing from the scope of the present disclosure.

The following prophetic examples are intended to be illustrative of the present disclosure and not limiting.

EXAMPLES

Example 1—Governing Flow Rate

Figure 39:
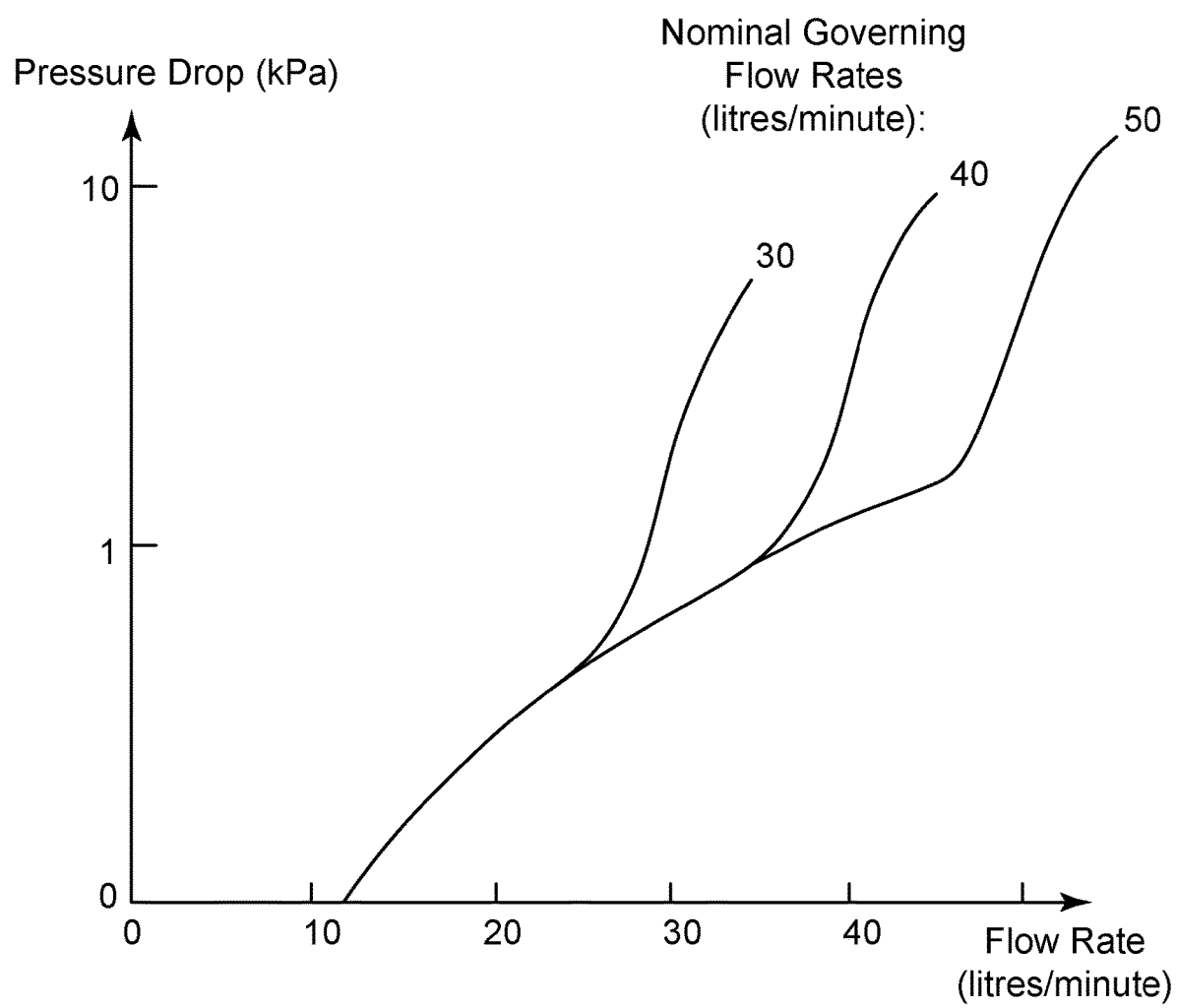
FIG. 39 is a graph of inhalation pressure drop (kPa) versus inhalation flow rate (L/min.) for three different embodiments of flow governors of the present disclosure.

FIG. 39 and Table 1 show the calculated range of flowrates that patients will inhale through flow governor assemblies having the configuration of the flow governor assembly 630 of FIGS. 35 and 36, comprising the flow governor 140 of FIGS. 22-27, with nominal flow governing values of 30, 40 and 50 L/min., respectively. It is clear from FIG. 39 and Table 1 that the spread in flow rates is greater for the higher flow governor nominal governing flow rates.

For modeling purposes, a normal distribution of governing flowrates has been taken around each target governing volumetric flow rate (i.e., 30 L/min., 40 L/min. and 50 L/min.), and the below spreads of data represent the distributions of flow rates at which the flow governors will operate within a population of flow governor assemblies. For example, for the case of a target governing volumetric flow rate of 30 L/min., a small number of flow governors will collapse at around 25 L/min, whereas most would be expected to govern at a flow rate close to the target of 30 L/min, and a small number will govern at a flow rate close to 35 L/min. It is assumed that if a flow governor collapses, then the resistance to flow will increase significantly and the pressure drop will be dominated by the dynamic, or variable, resistance.

The below data were calculated by modeling the pressure drop at various flow rates using the following equation:

$$\text{Pressure drop } (Pa) = ((R^2 + D^2) \times F^2)/1000$$

where:
R=Static resistance, $Pa^{0.5}$ (min./L)
D=Dynamic resistance, $Pa^{0.5}$ (min./L)
F=Flow rate, L/min The static resistance of the flow governor assembly 630 was estimated to be 0.83 $Pa^{0.5}$ (min./L), based on a combination of the resistance from the inlet losses, venturi resistance, the resistance of the flow governor, and the outlet losses.

TABLE 1

Ranges of flowrates with governing flow rates of 30, 40 and 50 L/min.

| Nominal governing flow rate | Flow rate when inhaling at 0.5 kPa | Flow rate when inhaling at 4 kPa |
|---|---|---|
| 30 L/min. | 25 L/min. | 35 L/min. |
| 40 L/min. | 27 L/min. | 45 L/min. |
| 50 L/min. | 27 L/min. | 55 L/min. |

The inventors have found particular advantages with flow governors of this configuration having a nominal governing flow rate of 30 L/min.

Example 2—Air Flow Resistance

Another important parameter that can be optimized is the static air flow resistance of the assembly.

A flow governor assembly having the configuration of the flow governor assembly 630 of FIGS. 35-36, comprising the flow governor 140 of FIGS. 22-27 was formed having a static resistance of 0.83 $Pa^{0.5}$ (min./L) and a nominal governing flow rate of 30 L/min. The performance of such a flow governor assembly is illustrated by the solid trace in FIG. 40, derived from data calculated using the equation described above in Example 1. As shown, this design of flow governor assembly will allow a patient who inhales with a pressure drop of only 0.5 kPa to inhale through the assembly at 25 L/min. The other extreme is a patient who creates a pressure drop of 4 kPa, and in this circumstance the inhalation flow rate will be governed according to the tolerance of the flow governor to between approximately 25 and 35 L/min. As is clear from the solid trace, this design ensures that all medications will be delivered within this flow rate range of approximately 25 to 35 L/min., independent of patient lung capacity. This will substantially improve dose consistency for patients (e.g., COPD patients), both inter-patient and intra-patient. All patients will thus benefit from such a flow governor assembly.

Figure 40:
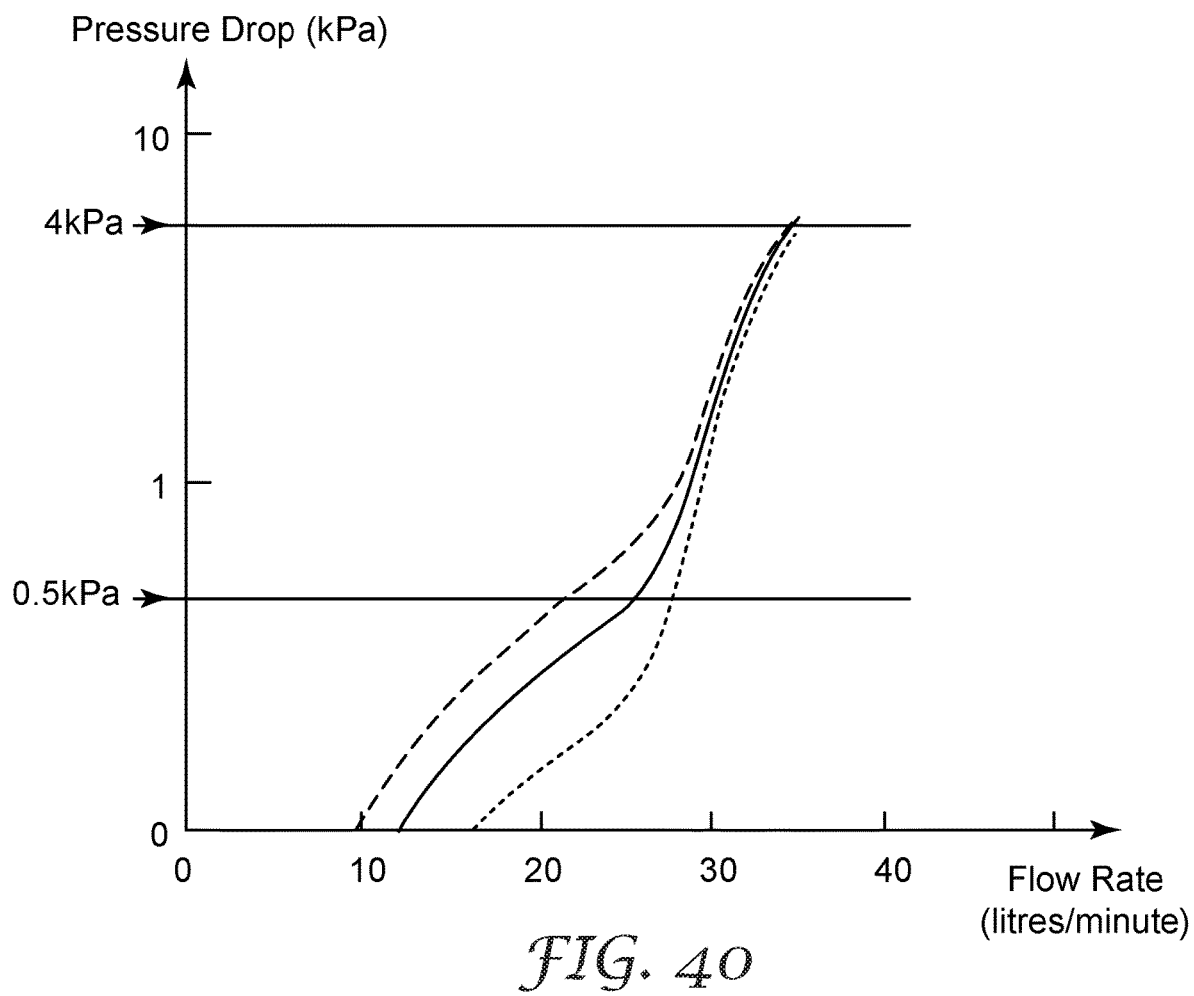
FIG. 40 is a graph of inhalation pressure drop (kPa) versus inhalation flow rate (L/min.) for three further embodiments of flow governors of the present disclosure.

The dashed trace in FIG. 40 shows the effect of a higher static resistance for the assembly, of 1.0 $Pa^{0.5}$ min./L. Some patients, particularly those who inhale with a pressure drop of only around 0.5 kPa, will not achieve the flow rate required for the flow governor to operate. These patients will not benefit directly from the flow governor.

The dotted trace in FIG. 40 shows the effect of a lower static resistance for the flow governor assembly, of 0.6 $Pa^{0.5}$ min./L. All patients will find it easier to inhale through the assembly and some weaker patients will find it easier to obtain a flow rate close to the governing flow rate. However, too low a static resistance can lead to increased drug deposition in the mouth and the throat, which is undesirable, so it is also preferable to avoid the static resistance being too low.

TABLE 2

| Characteristics | Flow rate when inhaling at 0.5 kPa | Flow rate when inhaling at 4 kPa |
|---|---|---|
| 30 L/min. flow governor; 0.6 $Pa^{0.5}$ min./L static resistance | 28 L/min. | 35 L/min. |
| 30 L/min. flow governor; 0.8 $Pa^{0.5}$ min./L static resistance | 25 L/min. | 35 L/min. |
| 30 L/min. flow governor; 1.0 $Pa^{0.5}$ min./L static resistance | 22 L/min. | 34 L/min. |

On the basis of these calculations and these considerations, the ideal static resistance for the flow governor assembly of FIGS. 35-36 comprising the flow governor of FIGS. 22-27 with a governing flow rate of 30 L/min. is considered to be around 0.8 $Pa^{0.5}$ min./L. At this resistance, practically all COPD and asthma patients would be expected to inhale at a flowrate above about 30 L/min. A higher resistance (e.g. 1.0-1.1 $Pa^{0.5}$ min./L) assembly, would result in some COPD patients not being able to reach an inhalation rate of 30 L/min.

Typically, only 95% of COPD patients produce an inhalation pressure drop of greater than 0.6 kPa. As a result, provision of flow governor assemblies (and/or inhalers) comprising the flow governors of the present disclosure caters satisfactorily for the vast majority of asthma and COPD patients, who can produce an inhalation pressure drop of between 0.5 and 4.0 kPa.

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure.

All references and publications cited herein are expressly incorporated herein by reference in their entirety into this disclosure.

Various features and aspects of the present disclosure are set forth in the following claims.

What is claimed is:

1. A medicinal inhaler comprising:
    a housing;
    an air flow path defined by at least partially the housing and including an air inlet and an air outlet;
    a flow governor positioned in the air flow path between the air inlet and the air outlet to govern air flow in the air flow path to a governing volumetric flow rate;
    a breath-actuated dose release firing system located in the housing, wherein the firing system is configured to release a dose of medicament at a firing volumetric flow rate less than the governing volumetric flow rate; and
    an inspiratory air flow detection system configured to detect an inspiratory air flow rate in the air flow path and to send an electrical signal to the firing system to fire when the inspiratory air flow rate is equal to at least the firing volumetric flow rate, wherein the inspiratory air flow detection system comprises a pressure sensor located in the air flow path upstream of the flow governor and downstream of the air inlet, and wherein the inspiratory air flow detection system further comprises a controller connected to the pressure sensor and the breath-actuated dose release firing system.

2. The inhaler of claim 1, wherein the medicinal inhaler includes a pressurized metered dose inhaler (pMDI).

3. The inhaler of claim 1, wherein the firing system includes a plunger movable between a first position and a second position to actuate a dose release valve.

4. The inhaler of claim 3, wherein the plunger is configured to be operatively coupled to a medicament canister comprising the dose release valve.

5. The inhaler of claim 3, wherein the firing system further includes a stored energy device configured to drive the plunger from the first position to the second position when stored energy in the stored energy device is released.

6. The inhaler of claim 3, wherein the stored energy device includes a biasing element.

7. The inhaler of claim 3, wherein the stored energy is triggered to release by a trigger connected to the inspiratory air flow detection system.

8. The inhaler of claim 3, wherein the firing system further includes:
    a guideway, wherein at least a portion of the guideway has a helical shape, the guideway having a first portion having a first helix angle with respect to the axis that is greater than zero, and a second portion having a second helix angle with respect to the axis, wherein the second helix angle is less than the first helix angle; and
    a projection dimensioned to be received in the guideway, the projection being movable in the guideway, such that the projection and the guideway are movable with respect to one another between a first position corresponding to the first position of the plunger and a second position corresponding to the second position of the plunger, such that the projection is configured to be cammed along the guideway when the stored energy device drives the plunger to move between the first position and the second position;
    wherein the guideway or the projection is fixedly coupled to the plunger.

9. The inhaler of claim 1, further comprising a second pressure sensor located in the air flow path downstream of the flow governor.

10. The inhaler of claim 9, wherein the pressure sensor upstream of the flow governor is located in a first conduit connected to the air flow path at a first location and the second pressure sensor is located in a second conduit connected to the air flow path at a second location downstream of the flow governor.

11. The inhaler of claim 10, wherein the first conduit has a first cross-sectional area, the second conduit has a second cross-sectional area, and the air flow path has a third cross-sectional area, and wherein the ratio of the first cross-sectional area to the third cross-sectional area and the ratio of the second cross-sectional area to the third cross-sectional area are each no greater than 0.2.

12. The inhaler of claim 1, wherein the flow governor includes:
    a tubular element that defines at least a portion of an air flow path, the tubular element comprising at least one flexible wall configured to flex inwardly in response to an air flow in the air flow path; and
    an internal support structure, located within the tubular element and configured to preserve at least a predetermined cross-sectional area of the air flow path within the tubular element when the at least one flexible wall of the tubular element flexes inwardly.

13. The inhaler of claim 12, wherein at least a portion of the internal support structure is formed by the housing.

* * * * *